US010858630B2

(12) United States Patent
Ho et al.

(10) Patent No.: US 10,858,630 B2
(45) Date of Patent: Dec. 8, 2020

(54) MODIFICATION OF N-TERMINAL REGION OF CAPSID PROTEINS FOR ENHANCED PROPERTIES OF ADENO-ASSOCIATED VIRUSES

(71) Applicant: WILLIAM MARSH RICE UNIVERSITY, Houston, TX (US)

(72) Inventors: Michelle Ho, Los Altos, CA (US); Junghae Suh, Houston, TX (US); Momona Yamagami, Seattle, WA (US); Veronica Gough, Durham, NC (US); Byunguk Kang, Gwangju Seo-gu (KR)

(73) Assignee: William Marsh Rice University, Houston, TX (US)

( * ) Notice: Subject to any disclaimer, the term of this patent is extended or adjusted under 35 U.S.C. 154(b) by 35 days.

(21) Appl. No.: 15/954,508

(22) Filed: Apr. 16, 2018

(65) Prior Publication Data
US 2018/0230440 A1    Aug. 16, 2018

Related U.S. Application Data

(63) Continuation of application No. PCT/US2016/057349, filed on Oct. 17, 2016.

(60) Provisional application No. 62/242,378, filed on Oct. 16, 2015.

(51) Int. Cl.
*C12N 7/00* (2006.01)
*C12N 15/86* (2006.01)
*C07K 14/005* (2006.01)

(52) U.S. Cl.
CPC .............. *C12N 7/00* (2013.01); *C07K 14/005* (2013.01); *C12N 15/86* (2013.01); *C12N 2750/14122* (2013.01); *C12N 2750/14143* (2013.01); *C12N 2810/6027* (2013.01)

(58) Field of Classification Search
CPC ....................................................... C12N 7/00
See application file for complete search history.

(56) References Cited

U.S. PATENT DOCUMENTS

| 2007/0036760 A1 | 2/2007 | Wilson et al. |
| 2013/0310443 A1 | 11/2013 | Srivastava et al. |
| 2015/0176027 A1 | 6/2015 | Gao et al. |

OTHER PUBLICATIONS

Bartel et al. (2011, Frontiers in Microbiology, vol. 2, pp. 1-10 (Year: 2011).*
A. Karsies et al., Degradation signals within both terminal domains of the cauliflower mosaic virus capsid protein precursor, The Plant Journal, 27(4):335-343 (2001).
Lawson et al., Identification and Characterization of a Protein Destruction Signal in the Encephalomyocarditis Virus 3C Protease, The Journal of Biological Chemistry, 274(14):9871-9980 (1999).
K.D. Foust et al., Entravascular AAV9 preferentially targets neonatal neurons and adult astrocytes, Nature Biotechnology, 27:59-65 (2009).
S. Duque et al., Intravenous Administration of Self-complementary AAV9 Enables Transgene Delivery to Adult Motor Neurons, Molecular Therapy, 17(7):1187-1196 (2009).
K. Inagaki et al., Robust Systemic Transduction with AAV9 Vectors in Mice: Efficient Global Cardiac Gene Transfer Superior to That of AAV8, Molecular Therapy, 14:45-53 (2006).
International Search Report and Written Opinion of the International Searching Authority, United States Patent Office, PCT/US16/57349, dated Apr. 6, 2017.
Grieger et al., "Separate basic region motifs within the adeno-associated virus capsid proteins are essential for infectivity and assembly", J Virol, (Jun. 1, 2006), vol. 80, pp. 5199-5210.
Popa-Wagner et al., "Impact of VP1-specific protein sequence motifs on adeno-associated virus type 2 intracellular trafficking and nuclear entry", J Virol., (Jun. 13, 2012), vol. 86, pp. 9163-9174.
Wu et al., "Mutational analysis of the adeno-associated virus type 2 (AAV2) capsid gene and construction of AAV2 vectors with altered tropism", J Virol., (Sep. 2000), vol. 74, pp. 8635-8647.

* cited by examiner

*Primary Examiner* — Thaian N. Ton
*Assistant Examiner* — David A. Montanari
(74) *Attorney, Agent, or Firm* — Robert R. Riddle; Reed Smith LLP

(57) ABSTRACT

The present disclosure provide viral compositions and methods for modulating adeno-associated virus properties including transduction efficiency, virus capsid assembly, viral genome packaging, capsid stability and intracellular processing. Engineered adeno-associated viruses with modifications in the N-terminal region of the capsid proteins VP1 or VP2 are provided which have varying effects on viral properties including transduction efficiency. Corresponding nucleic acids and amino acids are provided.

15 Claims, 14 Drawing Sheets
(6 of 14 Drawing Sheet(s) Filed in Color)
Specification includes a Sequence Listing.

Fig. 6

| Mutant | 155 | 156 | 157 |
|---|---|---|---|
| WT AAV2 | S | S | S |
| S155A | A | S | S |
| S156A | S | A | S |
| S157A | S | S | A |
| S156-7A | S | A | A |
| S155-7A | A | A | A |

Fig. 11A

|      | 154 | 155 | 156 | 157 | 158 |
|------|-----|-----|-----|-----|-----|
| AAV2 | D | S | S | S | G |
| AAV11| D | S | S | S | G |
| AAV4 | D | S | S | T | G |
| AAV1 | D | S | S | S | G |
| AAV6 | D | S | S | S | G |
| AAV8 | D | S | S | T | G |
| AAV10| D | S | S | T | G |
| AAV7 | D | S | S | T | G |
| AAV9 | D | S | S | A | G |

Fig. 11B

| Mutant | 155 | 156 | 157 |
|---|---|---|---|
| S155A | A | S | A |
| S155A_A157S | A | S | S |
| A157S | S | S | S |
| A157T | S | S | T |

MODIFICATION OF N-TERMINAL REGION OF CAPSID PROTEINS FOR ENHANCED PROPERTIES OF ADENO-ASSOCIATED VIRUSES

CROSS-REFERENCE TO RELATED APPLICATIONS

The present application is a continuation application of International Application No. PCT/US16/57349, filed Oct. 17, 2016, which claims priority to U.S. Provisional Application No. 62/242,378, filed on Oct. 16, 2015, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 14, 2016, is named 15-21019-WO_SL.txt and is 210,966 bytes in size.

BACKGROUND

A general strategy for gene therapy is shown in FIG. 1 which shows the insertion of a gene of interest into a plasmid which can then be delivered to the nucleus of a target cell resulting in expression of the desired gene product, e.g. a desired protein.

AAV is a 25 nm, non-enveloped virus. The intact AAV virus capsid, which contains the 4.7 kB genome of AAV which includes the rep and cap genes is comprised of VP1, VP2 and VP3 which are variants produced from the same cap ORF. These three viral proteins—VP1, VP2 and V3—assemble together in a 1:1:10 ratio to form a 60-mer shell, or capsid, of AAV. The single-stranded DNA genome of AAV is carried within the capsid lumen. As shown in FIG. 2, in wild-type AAV, the capsid subunits (VP1, VP2 and VP3) are produced from the same cap ORF by alternate mRNA splicing and alternative translation start codon usage. Because the VP1, VP2 and VP3 subunits of AAV can self-assemble, in a ratio of 1:1:10 respectively, to form the viral capsid, the addition of a transgene of interest or other genetic material permits the inclusion of the transgene or other genetic material inside the capsid structure upon self-assembly of the capsid subunits. AAV naturally infects human cells with a relatively high efficiency with an absence of pathological effects associated with its infection, which has led to its widespread testing for gene delivery applications. AAV can infect both dividing and non-dividing cells and persist in an extrachromosomal state without integrating into the genome of the host cell.

In the case of AAV, a nucleic acid molecule of interest can be packaged with the AAV capsid which then provides a delivery mechanism for delivering the nucleic acid molecule to the nucleus of a target cell as shown in FIG. 3. According to FIG. 3, the AAV virus binds to a receptor on the surface of the cell 1 and is brought into the cell by endocytosis 2-3 and released into the cytoplasm 4 by release from the endosome. The virus can then be trafficked to and enter the nucleus 5, releasing the nucleic acid molecule 6 and allowing for transcription or replication of the nucleic acid molecule 7. The nucleic acid molecule can encode a desired peptide or nucleic acid which can have other functions such as gene silencing or a regulatory impact on gene expression. By way of example but not limitation, such nucleic acids can deliver genes, RNA interference (RNAi) or CRISPR/genome editing tools to a target cell.

There are 12 serotypes of AAV, designated AAV1, AAV2, AAV3, AAV4, AAV5, AAV6, AAV7, AAV8, AAV9, AAV10, AAV11, and AAV12. The different serotypes can vary in tissue tropism, transduction efficiency, and other properties. In both the research and clinical settings, there is a need to control and modulate transduction efficiency and other properties to provide more effective gene delivery vectors. The present disclosure provides engineered adeno-associated viruses and methods for modulating the transduction efficiency, virus capsid assembly, viral genome packaging, capsid stability, and intracellular processing in host cells of such viruses utilizing mutations affecting and effecting S/T-rich regions and PEST domains in the N-terminal region of VP1 or VP2. The present disclosure also provides proteins and nucleic acid sequences useful in producing the adeno-associated viruses and in the methods disclosed herein.

SUMMARY

The present disclosure is directed to viral compositions and methods for modulating viral assembly, packaging and transduction in adeno-associated viruses. The present disclosure also provides nucleic acids and amino acids useful in making and using such viruses.

In an embodiment, an engineered adeno-associated virus is provided comprising one or more non-naturally occurring amino acid substitutions, insertions, or deletions in the N-terminal region of the VP1 or VP2 capsid protein. In some embodiments, the N-terminal region is a region between amino acid position 130 and amino acid position 198 of VP1 or a corresponding region in VP2.

In some embodiments, an engineered adeno-associated virus includes a sequence of amino acids at positions 155, 156 and 157 of VP1 or at positions 18, 19 and 20 of VP2 that is N-S-S, S-X-S, S-S-Y, N-X-S, N-S-Y, S-X-Y and N-X-Y, where N, X and Y are independently non-serine amino acids and the engineered adeno-associated virus is AAV1, AAV2, AAV3, or AAV6. In some embodiments, an engineered adeno-associated virus includes a sequence of amino acids at positions 154, 155 and 156 of VP1 or at positions 17, 18 and 19 of VP2 that is N-S-S, S-X-S, S-S-Y, N-X-S, N-S-Y, S-X-Y and N-X-Y, where N, X and Y are independently non-serine amino acids and the engineered adeno-associated virus is AAV11.

In some embodiments, an engineered adeno-associated virus includes a substitution of an amino acid at positions 155, 156 or 157 of VP1 or at positions 18, 19 or 20 of VP2, where the engineered adeno-associated virus is AAV1, AAV2, AAV3, or AAV6. In some embodiments, an engineered adeno-associated virus includes a substitution of an amino acid at positions 154, 155 or 156 of VP1 or at positions 17, 18 or 19 of VP2, where the engineered adeno-associated virus is AAV11.

In some embodiments, an engineered adeno-associated virus includes a deletion of at least one amino acid at positions 155, 156 or 157 of VP1 or at positions 18, 19 or 20 of VP2, where the engineered adeno-associated virus is AAV1, AAV2, AAV3, or AAV6. In some embodiments, an engineered adeno-associated virus includes a deletion of at least one amino acid at positions 154, 155 or 156 of VP1 or at positions 17, 18 or 19 of VP2, where the engineered adeno-associated virus is AAV11.

In some embodiments, an engineered adeno-associated virus includes a sequence of amino acids at positions 156, 157 and 158 of VP1 or at positions 19, 20 and 21 of VP2 that is S-S-S, N-S-T, S-X-T, S-S-Y, N-X-T, N-S-Y, S-X-Y, or N-X-Y, where N and X are independently non-serine amino acids and Y is a non-threonine amino acid and the engineered adeno-associated virus is AAV7, AAV8, AAV10.

In some embodiments, an engineered adeno-associated virus includes a substitution of an amino acid at positions 156, 157 or 158 of VP1 or at positions 19, 20 or 21 of VP2, where the engineered adeno-associated virus is AAV7, AAV8 or AAV10.

In some embodiments, an engineered adeno-associated virus includes a deletion of at least one amino acid at positions 156, 157 or 158 of VP1 or at positions 19, 20 or 21 of VP2, where the engineered adeno-associated virus is AAV7, AAV8 or AAV10.

In some embodiments, an engineered adeno-associated virus includes a sequence of amino acids at positions 154, 155 and 156 of VP1 or at positions 18, 19 and 20 of VP2 that is S-S-S, N-S-T, S-X-T, S-S-Y, N-X-T, N-S-Y, S-X-Y, or N-X-Y, where N and X are independently non-serine amino acids and Y is a non-threonine amino acid and the engineered adeno-associated virus is AAV4.

In some embodiments, an engineered adeno-associated virus includes a substitution of an amino acid at positions 154, 155 or 156 of VP1 or at positions 18, 19 or 20 of VP2, where the engineered adeno-associated virus is AAV4.

In some embodiments, an engineered adeno-associated virus includes a deletion of at least one amino acid at positions 154, 155 or 156 of VP1 or at positions 18, 19 or 20 of VP2, where the engineered adeno-associated virus is AAV4.

In some embodiments, an engineered adeno-associated virus includes a sequence of amino acids at positions 155, 156 and 157 of VP1 or at positions 18, 19 and 20 of VP2 that is S-S-S, N-S-A, S-X-A, S-S-Y, N-X-A, N-S-Y, S-X-Y, or N-X-Y, where N and X are independently non-serine amino acids and Y is a non-alanine amino acid and the engineered adeno-associated virus is AAV9.

In some embodiments, an engineered adeno-associated virus includes a substitution of an amino acid at positions 155, 156 or 157 of VP1 or at positions 18, 19 or 20 of VP2, where the engineered adeno-associated virus is AAV9.

In some embodiments, an engineered adeno-associated virus includes a deletion of at least one amino acid at positions 155, 156 or 157 of VP1 or at positions 18, 19 or 20 of VP2, where the engineered adeno-associated virus is AAV9.

In an embodiment, an engineered adeno-associated virus includes one or more non-naturally occurring amino acid substitutions or deletions at amino acid positions having threonine, lysine, serine, or tyrosine residues in a region between an amino acid at position 130 and an amino acid at position 198 of VP1 or a corresponding region of VP2.

In an embodiment, an engineered adeno-associated virus includes one or more non-naturally occurring amino acid substitutions or insertions of threonine, lysine, serine, or tyrosine residues in a region between an amino acid at position 130 and an amino acid at position 198 of VP1 or a corresponding region of VP2.

In an embodiment, an engineered adeno-associated virus includes at least one of the mutations listed in Table 3 in VP1 or at a corresponding position in VP2.

In an embodiment, a nucleic acid encoding an engineered VP1 or VP2 peptide includes one or more of a non-naturally occurring amino acid substitution, insertion, or deletion as set forth in Table 3.

In an embodiment, an engineered VP1 or VP2 peptide includes one or more of a non-naturally occurring amino acid substitution, insertion, or deletion as set forth in Table 3.

In an embodiment, a method if provided for modulating the transduction efficiency of an adeno-associated virus including a step of providing an engineered adeno-associated virus comprising one or more of a non-naturally occurring amino acid substitution, insertion, or deletion according to the present disclosure, including Table 3.

This summary is provided to introduce disclosure, certain aspects, advantages and novel features of the disclosure in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The patent or application file contains at least one drawing executed in color. Copies of this patent or patent application publication with color drawings will be provided by the office upon request and payment of the necessary fee.

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

All error bars shown in the figures are standard error of the mean (SEM) unless otherwise noted.

Figure 1:
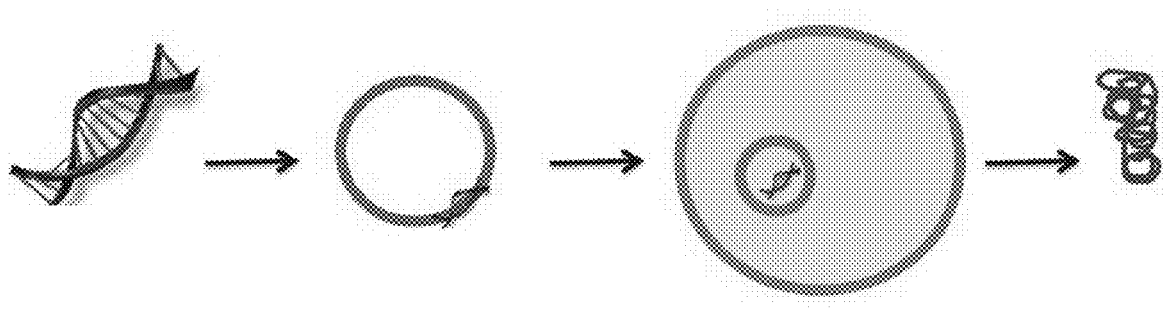

FIG. 1 depicts the general strategy for gene therapy application where a nucleic acid (DNA/gene) encoding a desired protein is incorporated into a plasmid and delivered to a cell nucleus resulting in expression of the desired protein.

Figure 2:
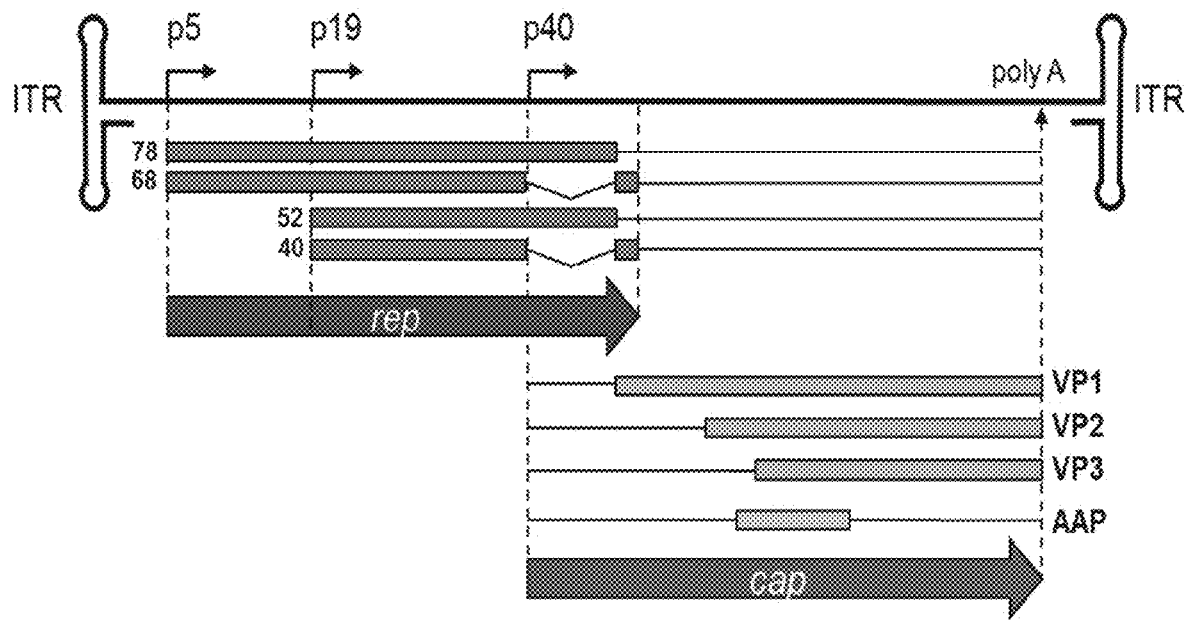

FIG. 2 depicts the AAV genome including the rep and cap genes and a graphical alignment of the gene products including capsid proteins VP1, VP2 and VP3 from the cap gene.

Figure 3:
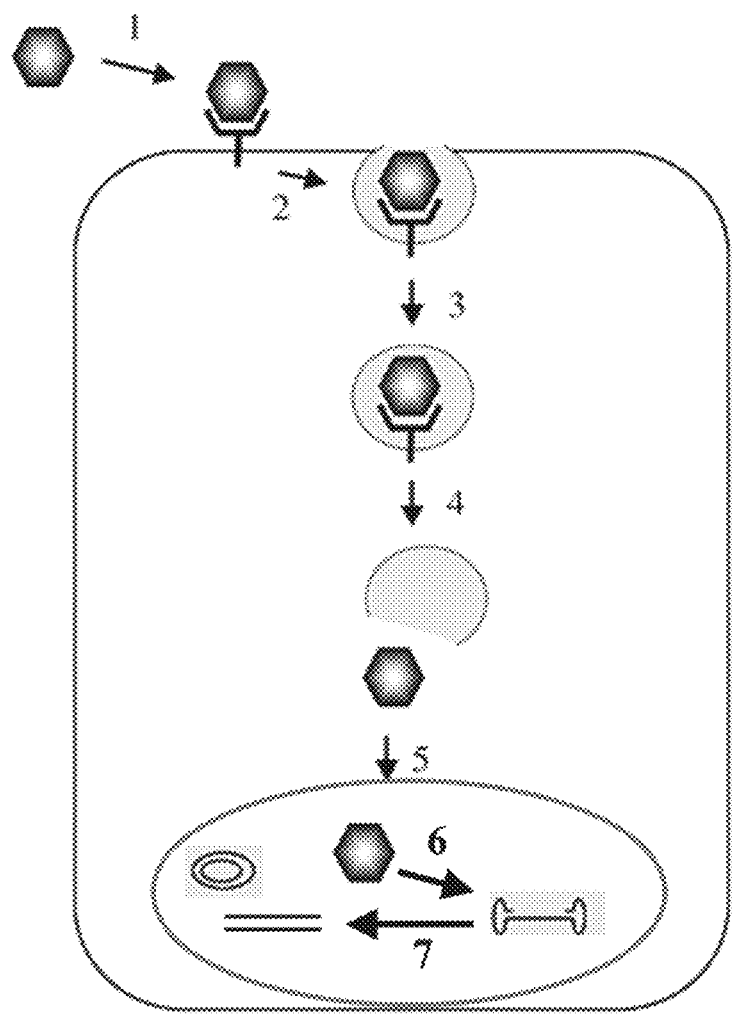

FIG. 3 depicts the AAV infectious pathway. The hexagons represent AAV virus.

Figures 4, 5A:
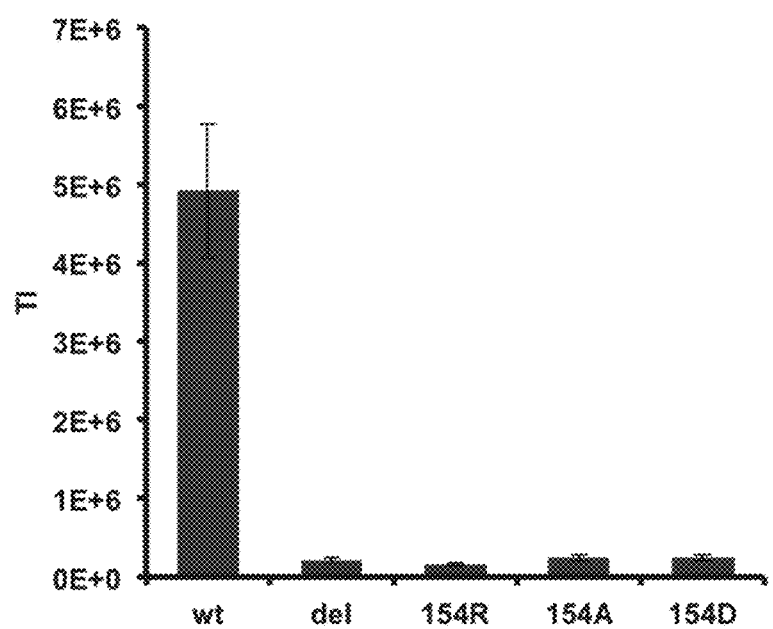

FIG. 4 depicts a partial sequence alignment of VP1 from AAV1, AAV2, AAV4, AAV6, AAV7, AAV8, AAV9, AAV10 and AAV11 generated using Clustal Omega. Residue numbering corresponds to AAV2 VP1. The basic motifs BR2 and BR3 and putative PEST domain area are aligned below the AAV VP1 sequences. Figure discloses SEQ ID NOS 25-33, respectively, in order of appearance.

FIG. 5A depicts the transduction index (TI=% GFP$^+$ cells×geometric mean fluorescence) for wild-type AAV2, AAV2 including a VP1 deletion mutant del149-160 ("del") or insertion mutants 154R, 154A and 154D in HEK293T cells. For each mutant, corresponding deletions or insertions were also present at corresponding positions of VP2.

Figure 5B:
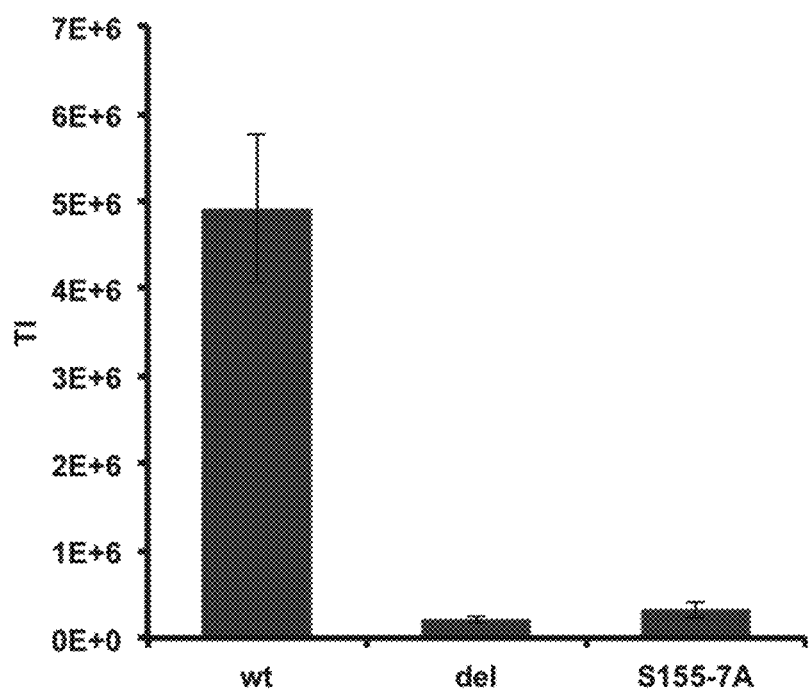

FIG. 5B depicts the transduction index for wild-type AAV2, AAV2 including a VP1 deletion mutant del149-160 ("del") or a substitution mutant S155-7A in HEK293T cells. For each mutant, corresponding deletions or substitutions were also present at corresponding positions of VP2.

FIG. 6 depicts several sequence modifications to VP1 of AAV2.

Figure 7A:
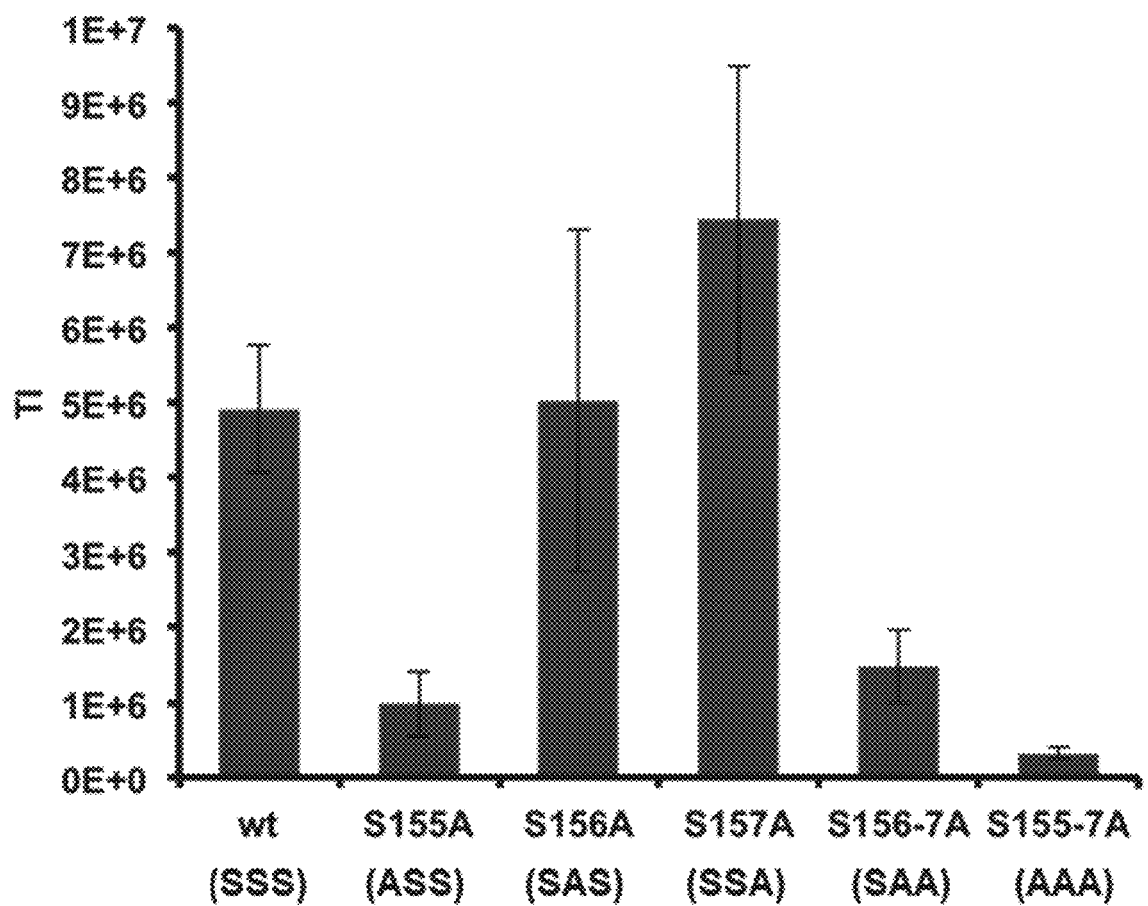

FIG. 7A depicts the transduction index wild-type AAV2 and the AAV2 variants shown in FIG. 6. For each variant, corresponding modifications were also present at corresponding positions of VP2.

Figure 7B:
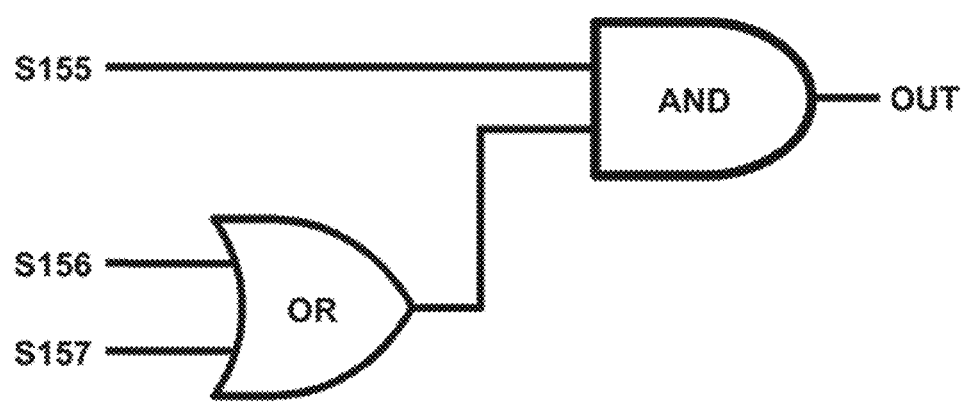

FIG. 7B shows a decision tree summarizing the results of FIG. 7A which demonstrate that a serine residue at position 155 (VP1 numbering) and at least one serine residue at position 156 or position 157 (VP1 numbering) are necessary to maintain the transduction efficiency of AAV2.

Figure 8:
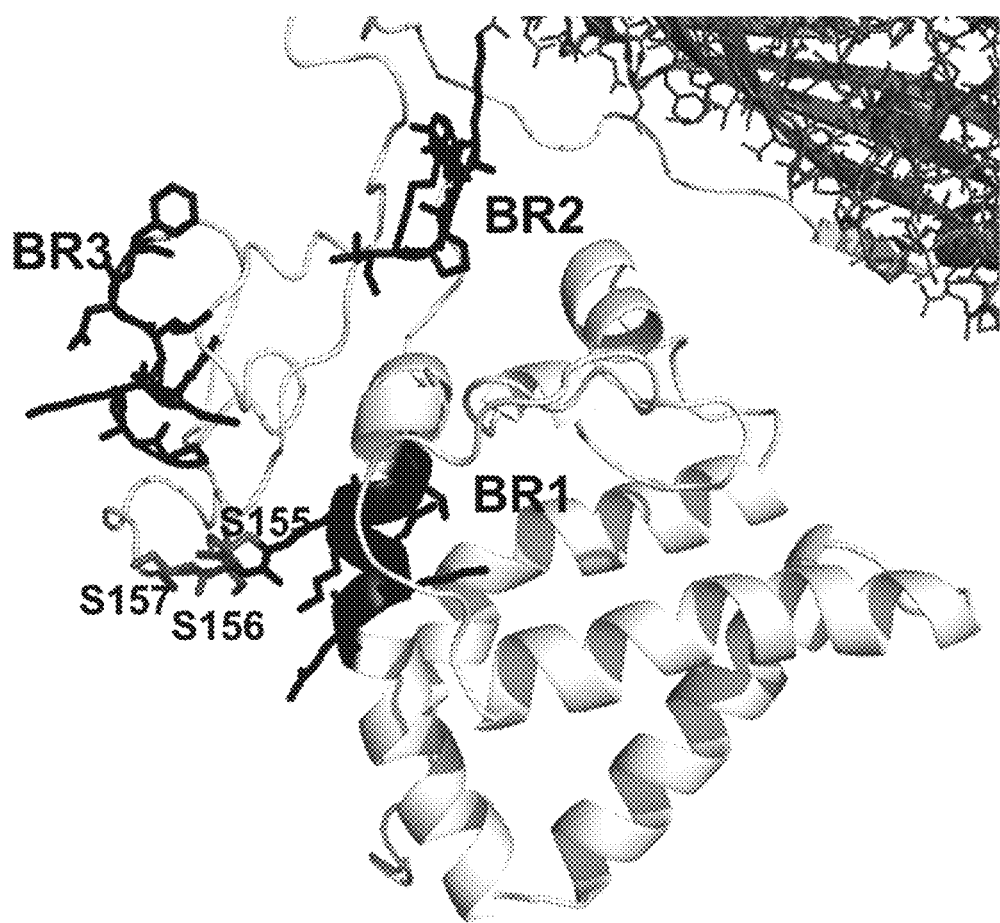

FIG. 8 depicts the three-dimensional protein structure around S155-S157 (triple serine motif) of AAV2 with the basic motifs BR1, BR2 and BR3 nearby to the serine motif. Ablation of BR1, BR2 and BR3 result in decreased transduction efficiency.

Figure 9:
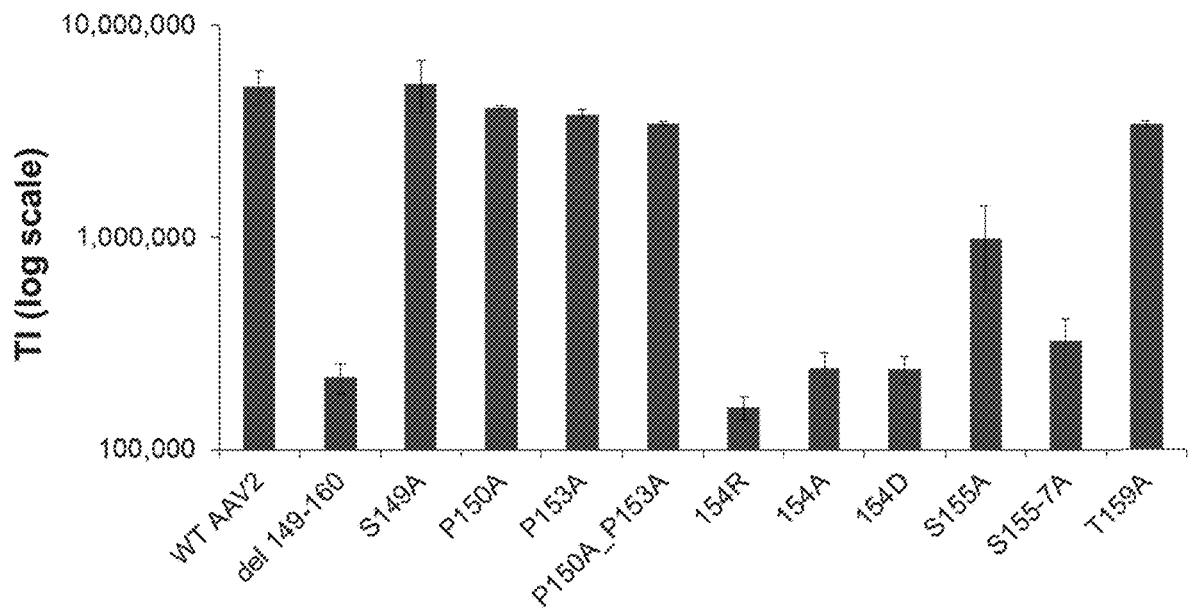

FIG. 9 depicts the transduction index for variants of AAV2 with the indicated modifications to VP1. For each variant, corresponding modifications were also present at corresponding positions of VP2.

Figure 10:
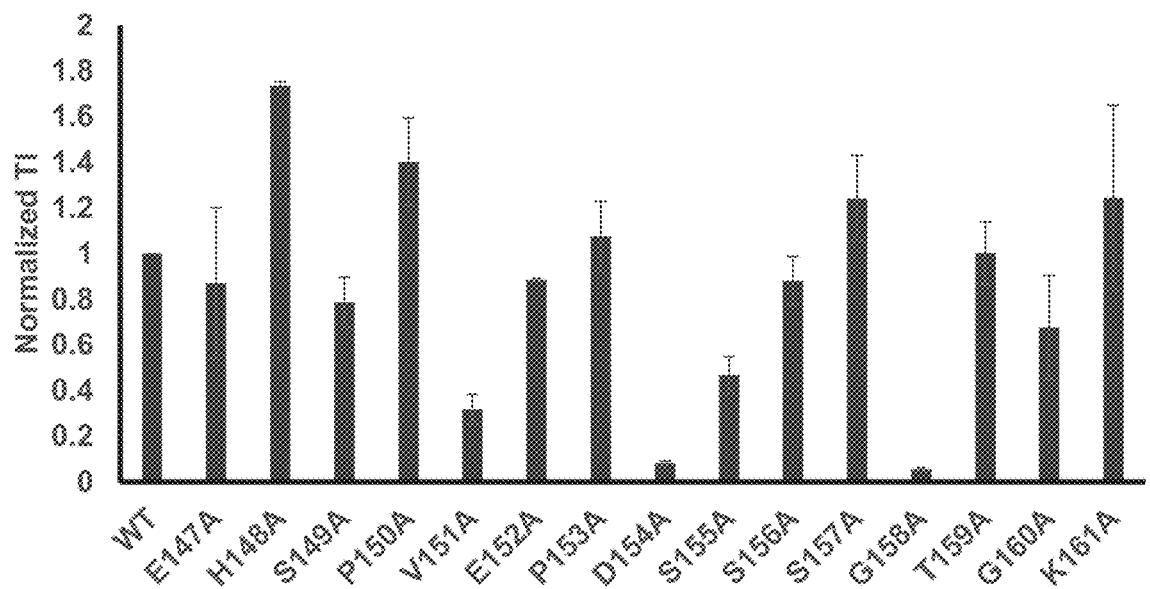

FIG. 10 depicts the normalized transduction index for variants of AAV2 with the indicated modifications to VP1. For each variant, corresponding modifications were also present at corresponding positions of VP2.

FIG. 11A depicts a partial sequence alignment of VP1 from AAV1, AAV2, AAV4, AAV6, AAV7, AAV8, AAV9, AAV10 and AAV11 corresponding, in part, to the triple serine motif of AAV2. Figure discloses SEQ ID NOS 34-42, respectively, in order of appearance.

FIG. 11B depicts several sequence modifications to VP1 of AAV9.

Figure 12A:
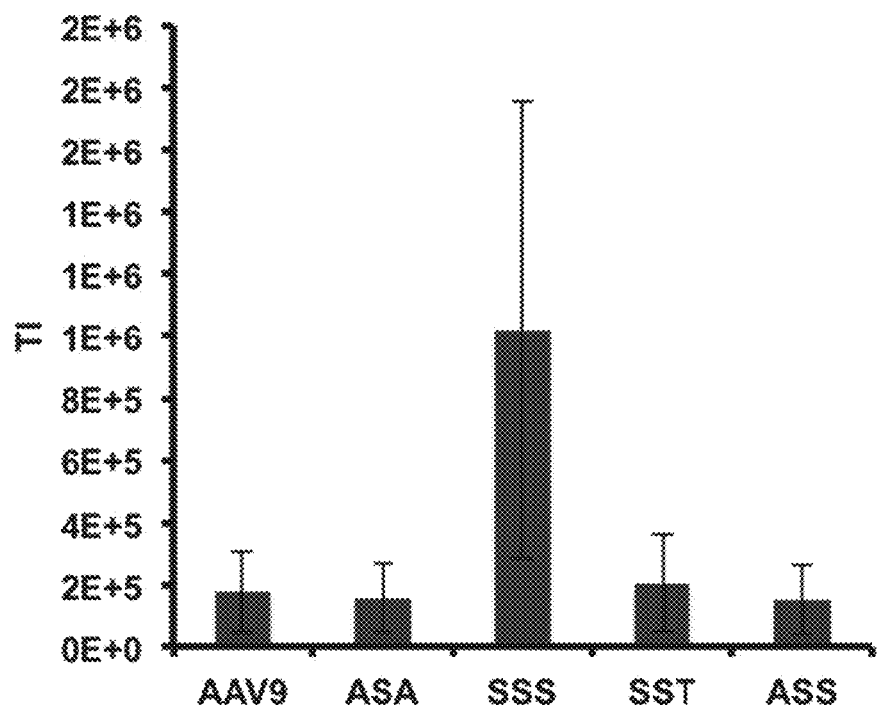

FIG. 12A depicts the transduction index for the AAV9 variants shown in FIG. 11B and a variant where A157 (as shown in FIG. 11A) is mutated to serine. For each variant, corresponding modifications were also present at corresponding positions of VP2.

Figure 12B:
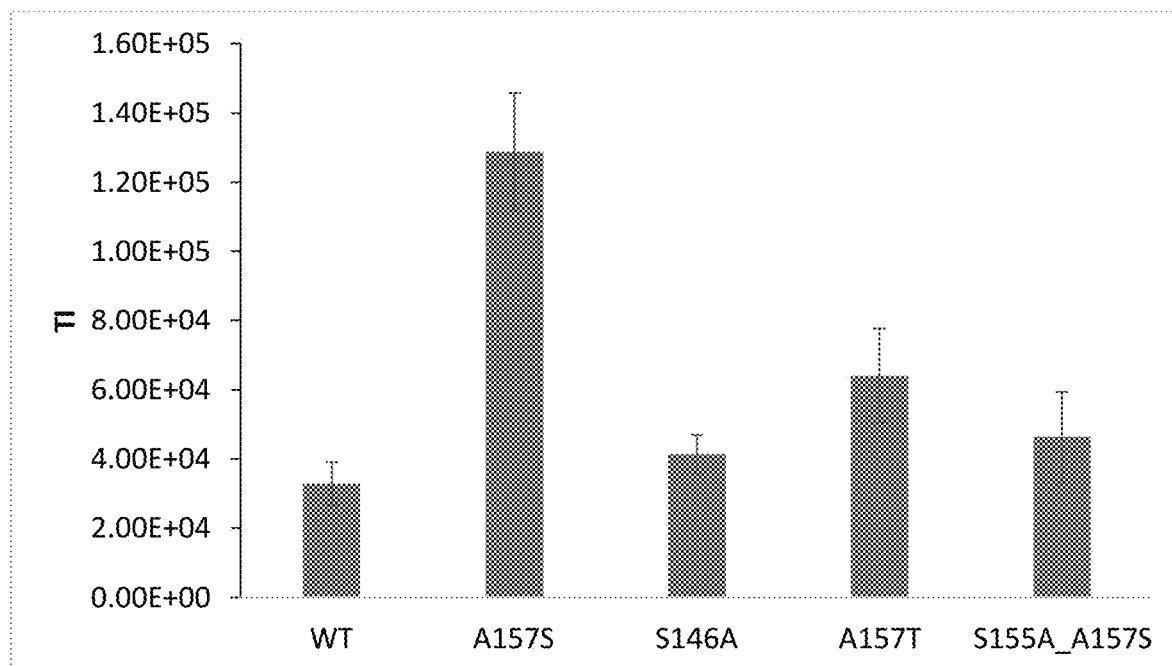

FIG. 12B depicts the transduction index for AAV9 variants A157S, S146A, A157T and S155A_A157S in CHO-Lec2 cells.

Figure 13A:
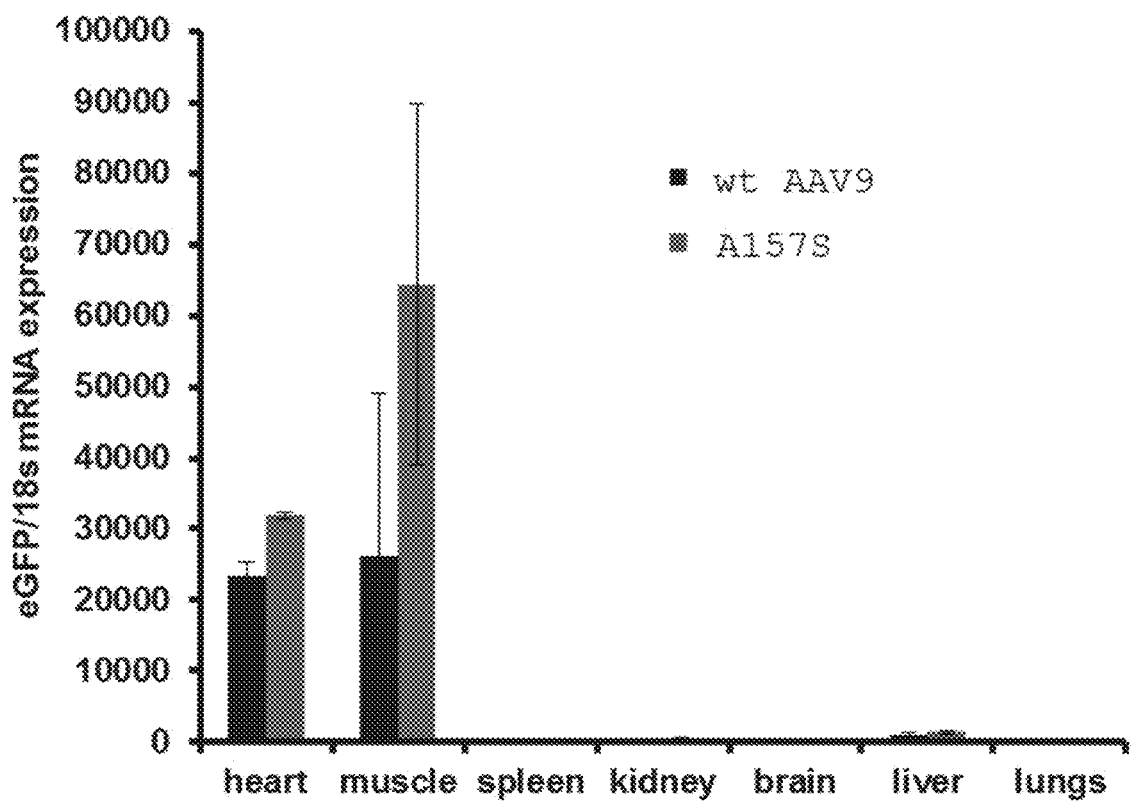

FIG. 13A depicts the in vivo expression based on eGFP/18s mRNA in tissues from mice (n=2) treated with wild-type AAV9 and AAV9 with a modification of A157S in the sequence of VP1. For the A157S variant, a mutation of alanine to serine was also present at the corresponding position in VP2.

Figure 13B:
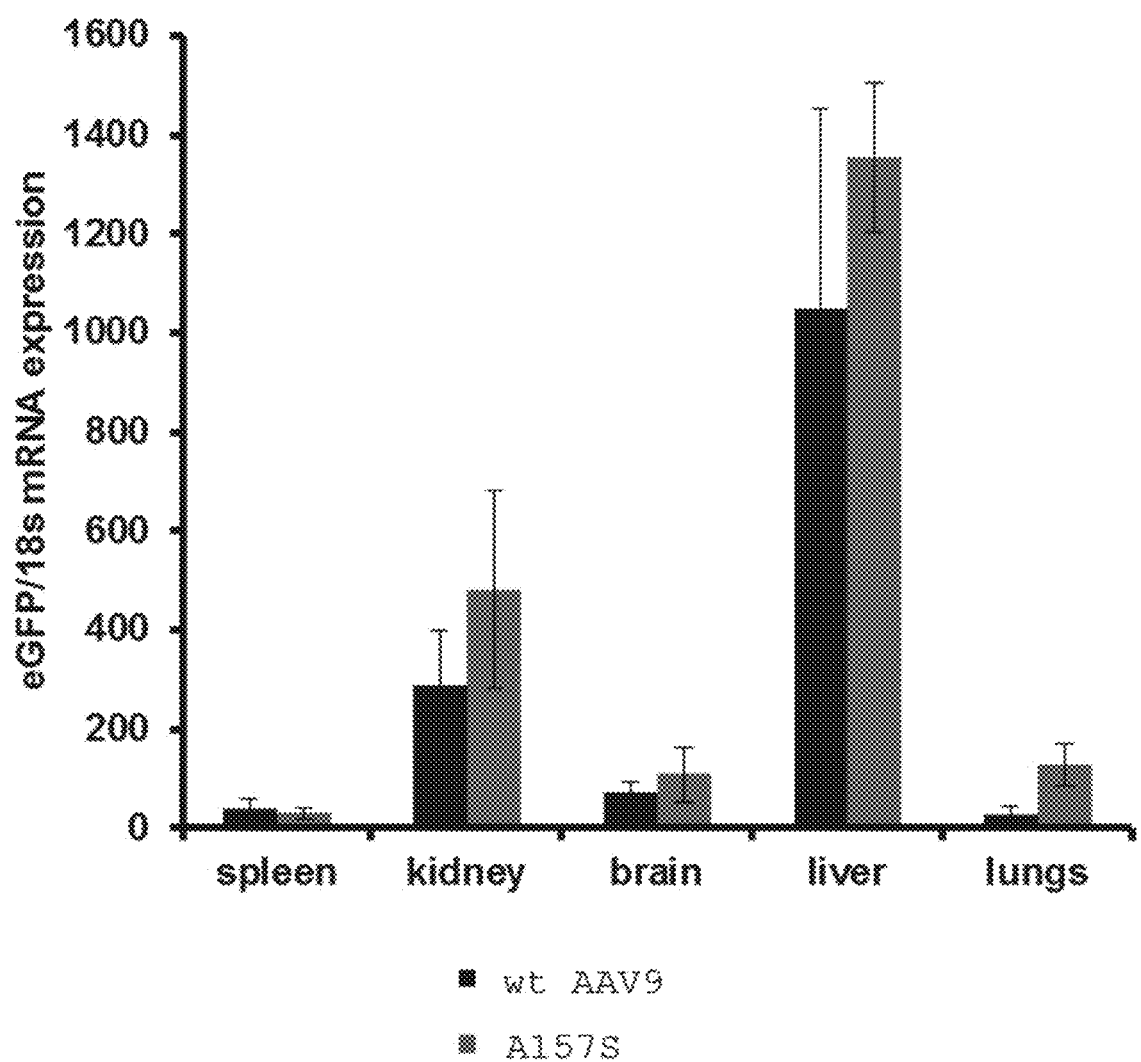

FIG. 13B depicts the in vivo expression based on eGFP/18s mRNA in tissues from mice (n=2) treated with wild-type AAV9 and AAV9 with a modification of A157S in the sequence of VP1. For the A157S variant, a mutation of alanine to serine was also present at the corresponding position in VP2.

Figure 14:
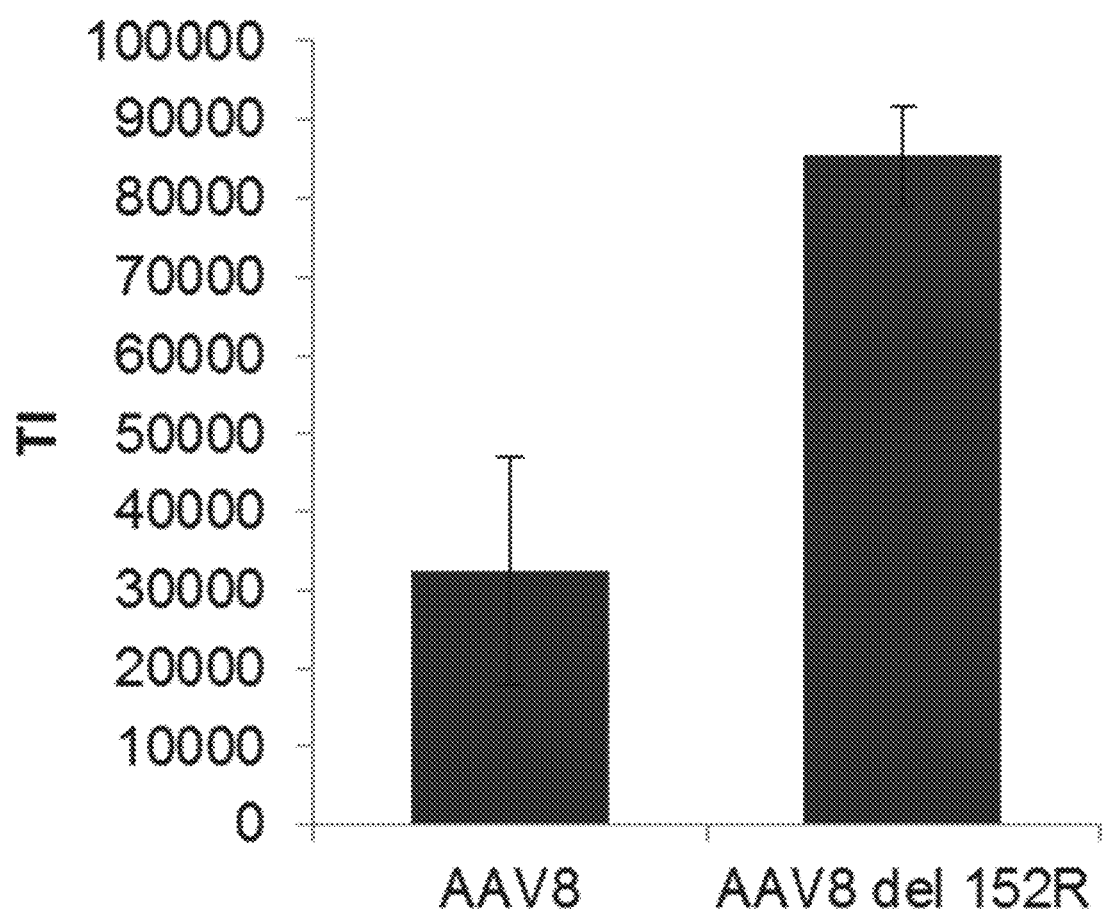

FIG. 14 depicts the transduction index for wild-type AAV8 and AAV8 with a deletion of arginine at position 152 of VP1 and at a corresponding position in VP2 in HEK293T cells.

DESCRIPTION

The present disclosure describes particular embodiments and with reference to certain drawings, but the subject matter is not limited thereto. The drawings described are only schematic and are non-limiting. In the drawings, the size of some of the elements may be exaggerated or distorted and not drawn on scale for illustrative purposes. Where the elements of the disclosure are designated as "a" or "an" in first appearance and designated as "the" or "said" for second or subsequent appearances unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Definitions

Certain terminology is used in the following description for convenience only and is not limiting. Certain words used herein designate directions in the drawings to which reference is made. Unless specifically set forth herein, the terms "a," "an" and "the" are not limited to one element, but instead should be read as meaning "at least one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

As used herein, the term "engineered adeno-associated virus" means a virus that has an amino acid sequence that is synthetically modified from the naturally-occurring amino acid sequence. More generally, "engineered" refers to any virus, nucleic acid molecule or amino acid molecule that has been modified from its naturally occurring form, e.g. sequence.

As used herein, the term "non-naturally occurring amino acid substitutions, insertions, or deletions" means a man-made substitution, insertion, or deletion of an amino acid that results in an amino acid sequence that does not exist in nature for the protein being so mutated.

As used herein, the term "S/T-rich motif" or "S/T-rich region" refers to a three amino acid region where at least two of the amino acid residues are serine and/or threonine.

As used herein, the term "PEST domain", "PEST motif" and "PEST region" mean an amino acid sequence that is: 1) enriched in proline (P), glutamate (E) or aspartate (D), serine (S), or threonine (T); 2) uninterrupted by positively charged residues; and 3) flanked on both ends by positively charged residues. In some embodiments, a PEST domain, PEST motif or PEST region comprises at least 12 amino acid residues.

As used herein, "enriched" means comprising a higher quantity than in surrounding regions. For example, an amino acid sequence would be enriched in serine if it has more serine residues than in surrounding amino acid sequences.

As used herein, "N-terminal region" refers to a region of amino acids proximate to the N-terminus of VP1 or VP2. Where an N-terminal region is defined with respect to VP1, it should be understood that the corresponding region in VP2 is also the N-terminal region to the extent that modifications are made to VP2 alone or in addition to VP1.

Throughout this disclosure, the terms peptide and protein and peptides and proteins are used interchangeably unless otherwise noted.

The present disclosure generally relates to adeno-associated virus (AAV) variants with mutations in the N-terminal region of the capsid protein that can alter viral properties, including virus capsid assembly, viral genome packaging, capsid stability, intracellular processing in host cells, and transduction efficiency. The present disclosure is based on the discovery of important motifs throughout the N-terminal region of VP1 or VP2 viral capsid proteins. It has been found that mutations in the N-terminal region of VP1 or VP2 can influence viral properties. Specifically, it has been found that modification which affect or effect PEST domains or S/T-rich regions can have effects on viral properties, permitting the modulation of viral properties such as transduction efficiency. In particular, it has been found that mutations to PEST regions between BR2 and BR3 in certain AAV serotypes can affect transduction efficiency. It has also been found that S/T-rich motifs, including the triple serine motif (S-S-S) of AAV2 are important for transduction. It is possible, without being bound to theory, that modifications to and resulting in PEST domains or S/T-rich regions in other capsid regions may also affect viral properties.

The present disclosure also provides a number of specific mutations (deletions, insertions, and amino acid substitutions) and strategies for mutations to key residues that modulate virus assembly, packaging, and transduction across multiple AAV serotypes.

Various enzymes (e.g. kinases) in the cell often modify serine (S or Ser), threonine (T or Thr), tyrosine (Y or Tyr), and lysine (K or Lys) residues (e.g. phosphorylation, ubiquitination) on proteins to alter the protein's stability, function, or intracellular trafficking. By manipulating the number and location of Ser, Thr, Tyr, and Lys residues in the N-terminal region of AAV capsid subunits, viral properties are modulated, including but not limited to virus capsid assembly, viral genome packaging, capsid stability, intracellular processing in host cells, and transduction efficiency.

It should be understood, that throughout this disclosure the reference to nucleic acids includes any nucleic acid, such as, by way of example but not limitation, DNA, RNA, cDNA. In some embodiments, a nucleic acid molecule is a cDNA, DNA or RNA molecule. In some embodiments, the nucleic acid molecule is contained in a plasmid.

In embodiments, the engineered adeno-associated virus can be selected from any serotype, including AAV1, AAV2, AAV3, AAV4, AAV5, AAV6, AAV7, AAV8, AAV9, AAV10, AAV11 and AAV12.

The amino acid sequences of the VP1 and VP2 capsid proteins can vary between serotypes. TABLE 1 below provides a sequence alignment using Clustal Omega of the VP1 capsid protein for each AAV serotype. The sequences of VP2 for each AAV serotype (SEQ ID NO: 43-SEQ ID NO: 54, corresponding to AAV1-AAV12, respectively) are truncated versions of the VP1 peptides, lacking 136-137 amino acids at the N-terminus of the protein depending on the specific serotype.

TABLE 1

Clustal Sequence Alignment of VP1 amino acid sequences of AAV serotypes 1-12 (SEQ ID NOS 1-12, respectively, in order of appearance)

```
AAV5    MSFVDHPPDWLEE-VGEGLREFLGLEAGPPKPKPNQQHQDQARGLVLPGYNYLGPGNGLD   59
AAV1    MAADGYLPDWLEDNLSEGIREWWDLKPGAPKPKANQQKDDGRGLVLPGYKYLGPFNGLD   60
AAV6    MAADGYLPDWLEDNLSEGIREWWDLKPGAPKPKANQQKQDDGRGLVLPGYKYLGPFNGLD   60
AAV2    MAADGYLPDWLEDTLSEGIRQWWKLKPGPPPPKPAERHKDDSRGLVLPGYKYLGPFNGLD   60
AAV3    MAADGYLPDWLEDNLSEGIREWWALKPGVPQPKANQQHQDNRRGLVLPGYKYLGPGNGLD   60
AAV9    MAADGYLPDWLEDNLSEGIREWWALKPGAPQPKANQQHQDNARGLVLPGYKYLGPGNGLD   60
AAV7    MAADGYLPDWLEDNLSEGIREWWDLKPGAPKPKANQQKQDNGRGLVLPGYKYLGPFNGLD   60
AAV8    MAADGYLPDWLEDNLSEGIREWWALKPGAPKPKANQQKQDDGRGLVLPGYKYLGPFNGLD   60
AAV10   MAADGYLPDWLEDNLSEGIREWWDLKPGAPKPKANQQKQDDGRGLVLPGYKYLGPFNGLD   60
AAV4    -MTDGYLPDWLEDNLSEGVREWWALQPGAPKPKANQQHQDNARGLVLPGYKYLGPGNGLD   59
AAV11   MAADGYLPDWLEDNLSEGIREWWDLKPGAPKPKANQQKQDDGRGLVLPGYKYLGPFNGLD   60
AAV12   MAADGYLPDWLEDNLSEGIREWWALKPGAPQPKANQQHQDNGRGLVLPGYKYLGPFNGLD   60
         : *****: :.**:*:: *: * * **  :::.*; ********.**** ****

AAV5    RGEPVNRADEVAREHDISYNEQLEAGDNPYLKYNHADAEFQEKLADDTSEGGNLGKAVFQ  119
AAV1    KGEPVNAADAAALEHDKAYDQQLKAGDNPYLRYNHADAEFQERLQEDTSEGGNLGRAVFQ  120
AAV6    KGEPVNAADAAALEHDKAYDQQLKAGDNPYLRYNHADAEFQERLQEDTSEGGNLGRAVFQ  120
AAV2    KGEPVNEADAAALEHDKAYDRQLDSGDNPYLKYNHADAEFQERLKEDTSEGGNLGRAVFQ  120
AAV3    KGEPVNEADAAALEHDKAYDQQLKAGDNPYLKYNHADAEFQERLQEDTSEGGNLGRAVFQ  120
AAV9    KGEPVNAADAAALEHDKAYDQQLKAGDNPYLKYNHADAEFQERLKEDTSEGGNLGRAVFQ  120
AAV7    KGEPVNAADAAALEHDKAYDQQLKAGDNPYLRYNHADAEFQERLQEDTSEGGNLGRAVFQ  120
AAV8    KGEPVNAADAAALEHDKAYDQQLQAGDNPYLRYNHADAEFQERLQEDTSEGGNLGRAVFQ  120
AAV10   KGEPVNAADAAALEHDKAYDQQLKAGDNPYLRYNHADAEFQERLQEDTSEGGNLGRAVFQ  120
AAV4    KGEPVNAADAAALEHDKAYDQQLKAGDNPYLKYNHADAEFQQRLQGDTSEGGNLGRAVFQ  119
AAV11   KGEPVNAADAAALEHDKAYDQQLKAGDNPYLRYNHADAEFQERLQEDTSEGGNLGRAVFQ  120
AAV12   KGEPVNEADAAALEHDKAYDKQLEQGDNPYLKYNHADAEFQQRLATDTSEGGNLGRAVFQ  120
        :***** **  .* *** :*:.**. ******:**********::*  *********:****

AAV5    AKKRVLEPFGLVEEGAKTAPTGKRIDDHFPKRKKARTEEDSK--------------PS--  163
AAV1    AKKRVLEPLGLVEEGAKTAPGKKRPVEQSPQ-EPDSSSGIGK---------TGQQPAKK  169
AAV6    AKKRVLEPFGLVEEGAKTAPGKKRPVEQSPQ-EPDSSSGIGK---------TGQQPAKK  169
AAV2    AKKRVLEPLGLVEEPVKTAPGKKRPVEHSPV-EPDSSSGTGK---------AGQQPARK  169
AAV3    AKKRILEPLGLVEEAAKTAPGKKGAVDQSPQ-EPDSSSGVGK---------SGKQPARK  169
AAV9    AKKRLLEPLGLVEEAAKTAPGKKRPVEQSPQ-EPDSSAGIGK---------SGAQPAKK  169
AAV7    AKKRVLEPLGLVEEGAKTAPAKKKRPVEPSPQRSPDSSTGIGK---------KGQQPAKK  170
AAV8    AKKRVLEPLGLVEEGAKTAPGKKRPVEPSPQRSPDSSTGIGK---------KGQQPARK  170
AAV10   AKKRVLEPLGLVEEAAKTAPGKKRPVEPSPQRSPDSSTGIGK---------KGQQPAKK  170
AAV4    AKKRVLEPLGLVEQAGETAPGKKRPLIESPQ-QPDSSTGIGK---------KGKQPAKK  168
AAV11   AKKRVLEPLGLVEEGAKTAPGKKRPLESPQE--PDSSSGIGK----K------GKQPARK  168
AAV12   AKKRILEPLGLVEEGVKTAPGKKRPLEKTPN--RPTNPDSGKAPAKKKQKDGEPADSARR  178
        ****.***:****. :*** *   .   .*   :

AAV5    -----TSSDAEAGPSGSQQLQIPAQPASSLGADTMSAGGGGPLGDNNQGADGVGNASGDW 218
AAV1    RLNFGQTGDSESVPD-PQPLGEPPATPAAVGPTTMASGGGAPMADNNEGADGVGNASGNW 228
```

TABLE 1-continued

Clustal Sequence Alignment of VP1 amino acid sequences of AAV
serotypes 1-12 (SEQ ID NOS 1-12, respectively, in order of appearance)

```
AAV6   RLNFGQTGDSESVPD-PQPLGEPPATPAAVGPTTMASGGGAPMADNNEGADGVGNASGNW 228
AAV2   RLNFGQTGDADSVPD-PQPLGQPPAAPSGLGTNTMATGSGAPMADNNEGADGVGNSSGNW 228
AAV3   RLNFGQTGDSESVPD-PQPLGEPPAAPTSLGSNTMASGGGAPMADNNEGADGVGNSSGNW 228
AAV9   RLNFGQTGDTESVPD-PQPIGEPPAAPSGVGSLTMASGGGAPVADNNEGADGVGSSSGNW 228
AAV7   RLNFGQTGDSESVPD-PQPLGEPPAAPSSVGSGTVAAGGGAPMADNNEGADGVGNASGNW 229
AAV8   RLNFGQTGDSESVPD-PQPLGEPPAAPSGVGPNTMAAGGGAPMADNNEGADGVGSSSGNW 229
AAV10  RLNFGQTGESESVPD-PQPIGEPPAGPSGLGSGTMAAGGGAPMADNNEGADGVGSSSGNW 229
AAV4   KLVFEDETGAGDG----PPEGSTSGAMS--DDSEMRAAAGGAAVEGGQGADGVGNASGDW 222
AAV11  RLNFEEDTGAGDG----PPEGSDTSAMS--SDIEMRAAPGGNAVDAGQGSDGVGNASGDW 222
AAV12  TLDF-EDSGAGDG----PPEGSSSGEMS--HDAEMRAAPGGNAVEAGQGADGVGNASGDW 231
                        :  :.    *.   :   :*.:****..**:*

AAV5   HCDSTWMGDRVVTKSTRTWVLPSYNNHQYREIKSGSV-DGSNANAYEGYSTPWGYFDENR 277
AAV1   HCDSTWLGDRVITTSTRTWALPTYNNHLYKQISSAST-GASNDNHYEGYSTPWGYFDENR 287
AAV6   HCDSTWLGDRVITTSTRTWALPTYNNHLYKQISSAST-GASNDNHYEGYSTPWGYFDENR 287
AAV2   HCDSTWMGDRVITTSTRTWALPTYNNHLYKQISSQ-S-GASNDNHYEGYSTPWGYFDENR 286
AAV3   HCDSQWLGDRVITTSTRTWALPTYNNHLYKQISSQ-S-GASNDNHYEGYSTPWGYFDENR 286
AAV9   HCDSQWLGDRVITTSTRTWALPTYNNHLYKQISNSTSGGSSNDNAYEGYSTPWGYFDENR 288
AAV7   HCDSTWLGDRVITTSTRTWALPTYNNHLYKQISSETA-GSTNDNTYFGYSTPWGYFDENR 288
AAV8   HCDSTWLGDRVITTSTRTWALPTYNNHLYKQISNGTSGGATNDNTYFGYSTPWGYFDENR 289
AAV10  HCDSTWLGDRVITTSTRTWALPTYNNHLYKQISNGTSGGSTNDNTYFGYSTPWGYFDENR 289
AAV4   HCDSTWSEGHVTTTSTRTWALPTYNNHLYKRLG-----ESLQSNTYNGFSTPWGYFDFNR 277
AAV11  HCDSTWSEGKVTTTSTRTWVLPTYNNHLYLRLG-----TTSSSNTYNGFSTPWGYFDFNR 277
AAV12  HCDSTWSEGRVTTTSTRTWVLPTYNNHLYLRIG-----TTANSNTYNGFSTPWGYFDFNR 286
       **** *  :* *.*****.**:**** *  .:        . * *.*:***********

AAV5   FHSHWSPRDWQRLINNYWGFRPRSLRVKIFNIQVKEVTVQDSTTTIANNLTSTVQVFTDD 337
AAV1   FHCHFSPRDWQRLINNNWGFRPKRLNFKLFNIQVKEVTTNDGVTTIANNLTSTVQVFSDS 347
AAV6   FHCHFSPRDWQRLINNNWGFRPKRLNFKLFNIQVKEVTTNDGVTTIANNLTSTVQVFSDS 347
AAV2   FHCHFSPRDWQRLINNNWGFRPKRLNFKLFNIQVKEVTQNDGTTTIANNLTSTVQVFTDS 346
AAV3   FHCHFSPRDWQRLINNNWGFRPKKLSFKLFNIQVRGVTQNDGTTTIANNLTSTVQVFTDS 346
AAV9   FHCHFSPRDWQRLINNNWGFRPKRLNFKLFNIQVKEVTDNNGVKTIANNLTSTVQVFTDS 348
AAV7   FHCHFSPRDWQRLINNNWGFRPKKLRFKLFNIQVKEVTTNDGVTTIANNLTSTIQVFSDS 348
AAV8   FHCHFSPRDWQRLINNNWGFRPKRLSFKLFNIQVKEVTQNEGTKTIANNLTSTIQVFTDS 349
AAV10  FHCHFSPRDWQRLINNNWGFRPKRLSFKLFNIQVKEVTQNEGTKTIANNLTSTIQVFTDS 349
AAV4   FHCHFSPRDWQRLINNNWGMRPKAMRVKIFNIQVKEVTTSNGETTVANNLTSTVQIFADS 337
AAV11  FHCHFSPRDWQRLINNNWGLRPKAMRVKIFNIQVKEVTTSNGETTVANNLTSTVQIFADS 337
AAV12  FHCHFSPRDWQRLINNNWGLRPKSMRVKIFNIQVKEVTTSNGETTVANNLTSTVQIFADS 346
       **.*:*********** **:**:   .*:*****:  **  ..  .*:*******:*:*.

AAV5   DYQLPYVVGNGTEGCLPAFPPQVFTLPQYGYATLNRDNT-ENPTERSSFFCLEYFPSKML 396
AAV1   EYQLPYVLGSAHQGCLPPFPADVFMIPQYGYLTLNNG---SQAVGRSSFYCLEYFPSQML 404
AAV6   EYQLPYVLGSAHQGCLPPFPADVFMIPQYGYLTLNNG---SQAVGRSSFYCLEYFPSQML 404
AAV2   EYQLPYVLGSAHQGCLPPFPADVFMVPQYGYLTLNNG---SQAVGRSSFYCLEYFPSQML 403
AAV3   EYQLPYVLGSAHQGCLPPFPADVFMVPQYGYLTLNNG---SQAVGRSSFYCLEYFPSQML 403
AAV9   DYQLPYVLGSAHEGCLPPFPADVFMIPQYGYLTLNDG---SQAVGRSSFYCLEYFPSQML 405
AAV7   EYQLPYVLGSAHQGCLPPFPADVFMIPQYGYLTLNNG---SQSVGRSSFYCLEYFPSQML 405
AAV8   EYQLPYVLGSAHQGCLPPFPADVFMIPQYGYLTLNNG---SQAVGRSSFYCLEYFPSQML 406
AAV10  EYQLPYVLGSAHQGCLPPFPADVFMIPQYGYLTLNNG---SQAVGRSSFYCLEYFPSQML 406
AAV4   SYELPYVMDAGQEGSLPPFPNDVFMVPQYGYCGLVTGNTSQQQTDRNAFYCLEYFPSQML 397
AAV11  SYELPYVMDAGQEGSLPPFPNDVFMVPQYGYCGIVTGEN-QNQTDRNAFYCLEYFPSQML 396
AAV12  TYELPYVMDAGQEGSFPPFPNDVFMVPQYGYCGVVTGKN-QNQTDRNAFYCLEYFPSQML 405
       *:****:    .*.:* ** :** :***** :         .: . *.:*:*******:**

AAV5   RTGNNFEFTYNFEEVPFHSSFAPSQNLFKLANPLVDQYLYRFVSTNNT-------       449
       GGVQF
AAV1   RTGNNFTFSYTFEEVPFHSSYAHSQSLDRLMNPLIDQYLYYLNRTQN-QSGSAQNKDLLF 463
AAV6   RTGNNFTFSYTFEDVPFHSSYAHSQSLDRLMNPLIDQYLYYLNRTQN-QSGSAQNKDLLF 463
AAV2   RTGNNFTFSYTFEDVPFHSSYAHSQSLDRLMNPLIDQYLYYLSRTN-TPSGTTTQSRLQF 462
AAV3   RTGNNFQFSYTFEDVPFHSSYAHSQSLDRLMNPLIDQYLYYLNRTQGTTSGTTNQSRLLF 463
AAV9   RTGNNFQFSYEFENVPFHSSYAHSQSLDRLMNPLIDQYLYYLSKTINGS--GQNQQTLKF 463
AAV7   RTGNNFEFSYSFEDVPFHSSYAHSQSLDRLMNPLIDQYLYYLARTQSNPGGTAGNRELQF 465
AAV8   RTGNNFQFTYTFEDVPFHSSYAHSQSLDRLMNPLIDQYLYYLSRTQT-TGGTANTQTLGF 465
AAV10  RTGNNFEFSYTFEDVPFHSSYAHSQSLDRLMNPLIDQYLYYLSRTQS-TGGTQGTQQLLF 465
AAV4   RTGNNFEITYSFEKVPFHSMYAHSQSLDRLMNPLIDQLWGLQSTTTGTTLNAGTATTNF 457
AAV11  RTGNNFEMAYNFEKVPFHSMYAHSQSLDRLMNPLLDQLWHLQSTTSGETLNQGNAATTF 456
AAV12  RTGNNFEVSYQFEKVPFHSMYAHSQSLDRMMNPLLDQLWHLQSTTTGNSLNQGTATTTY 465
       ******   .:.**.***** :* **.*   ***:****:   :  *                 :

AAV5   NKNLAGRYANTYKNWFPGPMGRTQGWNLGSGVNRASV-----SAFATTNRMELEGASYQV 504
AAV1   SRGSPAGMSVQPKNWLPGPCYRQQRVSKTKTDNNNSN-----FTWTGASKYNLNGRESII 518
AAV6   SRGSPAGMSVQPKNWLPGPCYRQQRVSKTKTDNNNSN-----FTWTGASKYNLNGRESII 518
AAV2   SQAGASDIRDQSRNWLPGPCYRQQRVSKTSADNNNSE-----YSWTGATKYHLNGRDSLV 517
AAV3   SQAGPQSMSLQARNWLPGPCYRQQRLSKTANDNNNSN-----FPWTAASKYHLNGRDSLV 518
AAV9   SVAGPSNMAVQGRNYIPGPSYRQQRVSTTVTQNNNSE-----FAWPGASSWALNGRNSLM 518
AAV7   YQGGPSTMAEQAKNWLPGPCFRQQRVSKTLDQNNNSN-----FAWTGATKYHLNGRNSLV 520
AAV8   SQGGPNTMANQAKNWLPGPCYRQQRVSTTTGQNNNSN-----FAWTAGTKYHLNGRNSLA 520
```

TABLE 1 -continued

Clustal Sequence Alignment of VP1 amino acid sequences of AAV
serotypes 1-12 (SEQ ID NOS 1-12, respectively, in order of appearance)

```
AAV10   SQAGPANMSAQAKNWLPGPCYRQQRVSTTLSQNNNSN-----FAWTGATKYHLNGRDSLV  520
AAV4    TKLRPTNFSNFKKNWLPGPSIKQQGFSKTANQNYKIPATGSDSLIKYETHSTLDGRWSAL  517
AAV11   GKIRSGDFAFYRKNWLPGPCVKQQRFSKTASQNYKIPASGGNALLKYDTHYTLNNRWSNI  516
AAV12   GKITTGDFAYYRKNWLPGACIKQQKFSKNANQNYKIPASGGDALLKYDTHTTLNGRWSNM  525
                :*::**    : *       *               . *:

AAV5    PPQPNGMTNNLQGSNTYALENTMIFNSQPANPGTTATYLEGNMLITSESETQPVNRVAYN  564
AAV1    NPGTAMASHKDDEDKFFPMSGVMIFGKESAG---ASNTALDNVMITDEEEIKATNPVATE  575
AAV6    NPGTAMASHKDDKDKFFPMSGVMIFGKESAG---ASNTALDNVMITDEEEIKATNPVATE  575
AAV2    NPGPAMASHKDDEEKFFPQSGVLIFGKQGSE---KTNVDIEKVMITDEEEIRTTNPVATE  574
AAV3    NPGPAMASHKDDEEKFFPMHGNLIFGKEGTT---ASNAELDNVMITDEEEIRTTNPVATE  575
AAV9    NPGPAMASHKEGEDRFFPLSGSLIFGKQGTG---RDNVDADKVMITNEEEIKTTNPVATE  575
AAV7    NPGVAMATHKDDEDRFFPSSGVLIFGKTGAT---N-KTTLENVLMTNEEEIRPTNPVATE  576
AAV8    NPGIAMATHKDDEERFFPSNGILIFGKQNAA---RDNADYSDVMLTSEEEIKTTNPVATE  577
AAV10   NPGVAMATHKDDEERFFPSSGVLMFGKQGAG---RDNVDYSSVMLTSEEEIKTTNPVATE  577
AAV4    TPGPPMATAGPADSKFS-NSQLIFAGPKQNG---NTATVPGTLIFTSEEELAATNATDTD  573
AAV11   APGPPMATAGPSDGDFS-NAQLIFPGPSVTG---NTTTSANNLLFTSEEEIAATNPRDTD  572
AAV12   APGPPMATAGAGDSDFS-NSQLIFAGPNPSG---NTTTSSNNLLFTSEEEIATTNPRDTD  581
             *      :         ::          :::*.*.*   .*      :

AAV5    VGGQMATNNQSSTTAPATGTYNLQEIVPGSVWMERDVYLQGPIWAKIPETGAHFHPSPAM  624
AAV1    REGTVAVNFQSSSTDPATGDVHAMGALPGMVWQDRDVYLQGPIWAKIPHTDGHFHPSPLM  635
AAV6    REGTVAVNLQSSSTDPATGDVHVMGALPGMVWQDRDVYLQGPIWAKIPHTDGHFHPSPLM  635
AAV2    QYGSVSTNLQRGNRQAATADVNTQGVLPGMVWQDRDVYLQGPIWAKIPHTDGHFHPSPLM  634
AAV3    QYGTVANNLQSSNTAPTTGTVNHQGALPGMVWQDRDVYLQGPIWAKIPHTDGHFHPSPLM  635
AAV9    SYGQVATNHQSAQAQAQTGWVQNQGILPGMVWQDRDVYLQGPIWAKIPHTDGNFHPSPLM  635
AAV7    EYGIVSSNLQAANTAAQTQVVNNQGALPGMVWQNRDVYLQGPIWAKIPHTDGNFHPSPLM  636
AAV8    EYGIVADNLQQQNTAPQIGTVNSQGALPGMVWQNRDVYLQGPIWAKIPHTDGNFHPSPLM  637
AAV10   QYGVVADNLQQANTGPIVGNVNSQGALPGMVWQNRDVYLQGPIWAKIPHTDGNFHPSPLM  637
AAV4    MWGNLPGGDQSNSNLPTVDRLTALGAVPGMVWQNRDIYYQGPIWAKIPHTDGHFHPSPLI  633
AAV11   MFGQIADNNQNATTAPITGNVTAMGVLPGMVWQNRDIYYQGPIWAKIPHADGHFHPSPLI  632
AAV12   MFGQIADNNQNATTAPHIANLDAMGIVPGMVWQNRDIYYQGPIWAKVPHTDGHFHPSPLM  641
         * :    *             :** **  :**:*  *******:*.:  ..*****  :

AAV5    GGEGLKHPPPMMLIKNTPVPGNI-TSFSDVPVSSFITQYSTGQVTVEMEWELKKENSKRW  683
AAV1    GGFGLKNPPPQILIKNTPVPANPPAEFSATKFASFITQYSTGQVSVEIEWELQKENSKRW  695
AAV6    GGEGLKHPPPQILIKNTPVPANPPAEFSATKFASFITQYSTGQVSVEIEWELQKENSKRW  695
AAV2    GGEGLKHPPPQILIKNTPVPANPSTTFSAAKFASFITQYSTGQVSVEIEWELQKENSKRW  694
AAV3    GGEGLKHPPPQIMIKNTPVPANPPTTFSPAKFASFITQYSTGQVSVEIEWELQKENSKRW  695
AAV9    GGEGMKHPPPQILIKNTPVPADPPTAFNKDKLNSFITQYSTGQVSVEIEWELQKENSKRW  695
AAV7    GGEGLKHPPPQILIKNTPVPANPPEVFTPAKFASFITQYSTGQVSVEIEWELQKENSKRW  696
AAV8    GGEGLKHPPPQILIKNTPVPADPPTTFNQSKLNSFITQYSTGQVSVEIEWELQKENSKRW  697
AAV10   GGEGLKHPPPQILIKNTPVPADPPTTFSQAKLASFITQYSTGQVSVEIEWELQKENSKRW  697
AAV4    GGEGLKHPPPQIFIKNTPVPANPATTFSSTPVNSFITQYSTGQVSVQIDWEIQKERSKRW  693
AAV11   GGEGLKHPPPQIFIKNTPVPANPATTFTAARVDSFITQYSTGQVAVQIEWEIEKERSKRW  692
AAV12   GGEGLKHPPPQIFIKNTPVPANPNTTFSAARINSFLTQYSTGQVAVQIDWEIQKEHSKRW  701
        ****:*.***  ::*******.:      *.    .**:*******:*::**::**.****

AAV5    NPEIQYTNNYNDPQFVDFAPDSTGEYRTTRPIGTRYLTRPL           724
AAV1    NPEVQYTSNYAKSANVDFTVDNNGLYTEPRPIGTRYLTRPL           736
AAV6    NPEVQYTSNYAKSANVDFTVDNNGLYTEPRPIGTRYLTRPL           736
AAV2    NPEIQYTSNYNKSVNVDFTVDTNGVYSEPRPIGTRYLTRNL           735
AAV3    NPEIQYTSNYNKSVNVDFTVDTNGVYSEPRPIGTRYLTRNL           736
AAV9    NPEIQYTSNYYKSNNVEFAVNTEGVYSEPRPIGTRYLTRNL           736
AAV7    NPEIQYTSNFEKQTGVDFAVDSQGVYSEPRPIGTRYLTRNL           737
AAV8    NPEIQYTSNYYKSTSVDFAVNTEGVYSEPRPIGTRYLTRNL           738
AAV10   NPEIQYTSNYYKSTNVDFAVNTEGTYSEPRPIGTRYLTRNL           738
AAV4    NPEVQFTSNYGQQNSLLWAPDAAGKYTEPRAIGTRYLTHHL           734
AAV11   NPEVQFTSNYGNQSSMLWAPDTTGKYTEPRVIGSRYLTNHL           733
AAV12   NPEVQFTSNYGTQNSMLWAPDNAGNYHELRAIGSRFLTHHL           742
        ***:*:*.*:          :  :::   *  *  * **:*:**. *
```

The sequences of VP1 for several AAV serotypes were analyzed using an online PEST-FIND algorithm to identify putative PEST domains. The PEST-FIND algorithm scans protein sequences and highlights putative PEST motifs, assigning scores of −50 to +50 based on how likely the sequence is a PEST motif. PEST domains typically signal proteins for degradation (likely through ubiquitination via the ubiquitin/26S proteasome pathway) and several viruses have been shown to use these motifs in various steps of the replication and/or transduction process. However, PEST domains were not previously reported or investigated in AAV. Several putative PEST domains were identified in several AAV serotypes as shown in TABLE 2 below:

TABLE 2

Putative PEST Domains in AAV serotypes 1-4, 6, 9 and 11-12

| Serotype | Amino Acid Position (VP1) | Putative PEST Domain Sequence | PEST Score | SEQ ID NO: |
|---|---|---|---|---|
| AAV1 | 144-161 | RPVEQSPQEPDSSSGIGK | 7.72 | 13 |
| AAV2 | 148-161 | HSPVEPDSSSGTGK | 10.85 | 14 |
| AAV3 | 143-161 | KGAVDQSPQEPDSSSGVGK | 3.17 | 15 |
| AAV4 | 143-160 | RPLIESPQQPDSSTGIGK | 0.54 | 16 |
| AAV6 | 144-161 | RPVEQSPQEPDSSSGIGK | 7.72 | 17 |
| AAV9 | 144-161 | RPVEQSPQEPDSSAGIGK | 4.35 | 18 |
| AAV11 | 144-160 | RPLESPQEPDSSSGIGK | 8.53 | 19 |
| AAV4 | 169-198 | KLVFEDETGAGDGPPEGST SGAMSDDSEMR | 9.35 | 20 |
| AAV11 | 169-198 | RLNFEEDTGAGDGPPEGSD TSAMSSDIEMR | 9.05 | 21 |
| AAV12 | 178-202 | RTLDFEDSGAGDGPPEGSS SSGEMSH | 10.86 | 22 |

Although AAV8 has a S/T-rich region at amino acids 156-158, it does not contain a putative PEST domain because of the charged arginine (R) residue at position 152. Deletion of the arginine (R) residue at amino acid position 152 would permit a putative PEST domain in AAV8 VP1 and has been demonstrated to improve transduction efficiency by 2.6-fold versus wild-type AAV8. Similarly, in AAV5, insertion of a PEST domain, such as that of AAV2 may improve transduction efficiency or intracellular trafficking. Similarly, AAV7 and AAV10 have a charged arginine interrupting a putative PEST domain. As shown in Table 2, AAV 4, 11 and 12 have PEST motifs downstream from most other serotypes.

S/T-rich regions can be targeted for mutation because serine and threonine residues are more commonly phosphorylated in cells compared to tyrosine residues, although tyrosine rich regions may provide similar properties. It was noted that the S155-S157 residues in AAV2 (VP1 numbering) are important for transduction. By substituting alanine (A) for serine singly or in combination in these positions, the overall transduction efficiency can be modulated, e.g. 3-152% compared to wild-type AAV2 in HEK293T cells. Similar trends have been observed in HeLa cells. This triple serine motif is highly conserved amongst several AAV serotypes (AAV1, 2, 4, 6, 7, 8, 10 and 11) that share the sequence P153-D-S-S-S/T-G158 (AAV2 VP1 numbering). This suggests that these serine residues are important (especially S155 and S156) due to their high levels of conservation.

AAV9 varies slightly with an S-S-A instead of S-S-S/T in the same capsid location. Notably, by creating a single amino acid substitution to recapitulate the S-S-S of AAV2 in AAV9, the A157S (AAV9 VP1 numbering) mutant demonstrates dramatically increased transduction efficiency, e.g. up 550% greater than wild-type AAV9, across multiple cell lines in vitro and higher transduction levels in multiple organs (heart, liver, kidney, brain, muscle, and lungs) in vivo upon systemic injection in nude mice comparted to wild-type AAV9 one week post-injection as discussed in the Examples.

AAV9 is widely used as an efficient gene delivery vehicle in academic and clinical settings for several diseases. The AAV9 A157S mutant and AAV8 del152 mutants may provide improved transduction efficiency and be useful as more efficient gene delivery vectors.

In an embodiment, an engineered adeno-associated virus is provided comprising one or more non-naturally occurring amino acid substitutions, insertions, or deletions in the N-terminal region of the VP1 or VP2 capsid protein. The N-terminal region of VP1 includes regions of amino acids proximate to the N-terminus of VP1. In some embodiments, the N-terminal region includes about the first 200 amino acids of VP1 or the corresponding positions in VP2. In some embodiments, the N-terminal region includes a subset of amino acid positions, such as amino acids 130 to 198. In some embodiments, the N-terminal region can include a region beginning with amino acid position 1, 10, 20, 30, 40, 50, 60, 70, 80, 90, 100, 110, 120, 130, 140, 150, 160, 170, 180 or 190 and ending with amino acid position 200, 190, 180, 170, 160, 150, 140, 130, 120, 110, 100, 90, 80, 70, 60, 50, 40, 30, 20, or 10 of VP1 or a corresponding region in VP2. In some embodiments, the N-terminal region includes the sequence between the amino acid at position 130 and the amino acid at position 198 of VP1, or the corresponding region of VP2. The non-naturally occurring substitutions, insertions, or deletions may result in a S/T-rich region or a PEST domain In some embodiments, an engineered adeno-associated virus comprises at least one mutation set forth in TABLE 3 below:

TABLE 3

Mutations in the N-terminal Region of Capsid Proteins of Various AAV Serotypes
("PDSSSG" disclosed as SEQ ID NO: 23)

| Serotype | Name | Mutation | Serotype | Name | Mutation | Serotype | Name | Mutation |
|---|---|---|---|---|---|---|---|---|
| AAV2 | S149A | Sub | AAV8 | del152 | Del | AAV6 | 156R | Ins |
| AAV2 | S155A | Sub | AAV8 | T158S | Sub | AAV6 | S155A | Sub |
| AAV2 | S156A | Sub | AAV8 | S156A | Sub | AAV6 | S156A | Sub |
| AAV2 | S157A | Sub | AAV8 | S157A | Sub | AAV6 | S157A | Sub |
| AAV2 | S155-7A | Sub | AAV8 | T158A | Sub | AAV6 | S155-7A | Sub |
| AAV2 | P150A | Sub | AAV5 | del148-160 | Del | AAV6 | S155T | Sub |
| AAV2 | P153A | Sub | AAV5 | 2PESTrep | Sub | AAV6 | S156T | Sub |
| AAV2 | P150_P153A | Sub | AAV5 | 2PESTins148 | Ins | AAV6 | S157T | Sub |
| AAV2 | T159A | Sub | AAV5 | 148PD555G | Ins | AAV6 | 154A | Ins |
| AAV2 | 154R | Ins | AAV5 | 148SSS | Ins | AAV6 | 154D | Ins |
| AAV2 | del149-160 | Del | AAV9 | S155A | Sub | AAV6 | 154R | Ins |
| AAV2 | S156-7A | Sub | AAV9 | S155A_A157S | Sub | AAV6 | del155-7 | Del |
| AAV2 | S155T | Sub | AAV9 | A157S | Sub | AAV4 | del169-198 | Del |

TABLE 3-continued

Mutations in the N-terminal Region of Capsid Proteins of Various AAV Serotypes
("PDSSSG" disclosed as SEQ ID NO: 23)

| Serotype | Name | Mutation | Serotype | Name | Mutation | Serotype | Name | Mutation |
|---|---|---|---|---|---|---|---|---|
| AAV2 | S156T | Sub | AAV9 | A157T | Sub | AAV4 | T156S | Sub |
| AAV2 | S157T | Sub | AAV9 | S156A | Sub | AAV4 | 153R | Ins |
| AAV2 | P145A | Sub | AAV9 | S155-7A | Sub | AAV4 | 153A | Ins |
| AAV2 | E147A | Sub | AAV9 | S155-7T | Sub | AAV4 | 153D | Ins |
| AAV2 | V151A | Sub | AAV9 | S155T | Sub | AAV4 | S195A | Sub |
| AAV2 | E152A | Sub | AAV9 | S156T | Sub | AAV4 | S192A | Sub |
| AAV2 | D154A | Sub | AAV9 | S155-6T | Sub | AAV4 | S188A | Sub |
| AAV2 | G158A | Sub | AAV11 | del169-198 | Del | AAV4 | S186A | Sub |
| AAV2 | G160A | Sub | AAV11 | del144-160 | Del | AAV2 | K105R | Sub |
| AAV2 | 155S | Ins | AAV11 | del169-198__del144-160 | Del | AAV2 | K26R | Sub |
| AAV2 | 155A | Ins | AAV11 | 185R | Ins | AAV2 | K142R | Sub |
| AAV2 | 156A | Ins | AAV11 | 153R | Ins | AAV2 | k143R | Sub |
| AAV2 | S181A | Sub | AAV11 | 153R__185R | Ins | AAV2 | K142-3R | Sub |
| AAV2 | del155 | Del | AAV11 | S154A | Sub | AAV9 | S155A | Sub |
| AAV2 | del155-6 | Del | AAV11 | S155A | Sub | AAV9 | S155A__A157S | Sub |
| AAV2 | del155-7 | Del | AAV11 | S156A | Sub | | | |
| AAV2 | S181T | Sub | AAV11 | S154-6A | Sub | | | |

With respect to TABLE 3, all numbering (amino acid positions) is based on VP1 numbering of the serotype listed. "Mutation" column stands for what kind of mutation is being made: Sub=substitution; Ins=insertion; Del=deletion. AAV5 mutants with "2PEST" denotes insertion of the PEST domain (amino acids 149-160) of AAV2 into AAV5. AAV5 mutants with "2PESTrep" denotes substitution of amino acids at 144-160 in VP1 of AAV5 with the PEST domain (amino acids 149-160) of AAV2.

In some embodiments, an engineered adeno-associated virus includes a sequence of amino acids at positions 155, 156 and 157 of VP1 or at positions 18, 19 and 20 of VP2 that is N-S-S, S-X-S, S-S-Y, N-X-S, N-S-Y, S-X-Y and N-X-Y, where N, X and Y are independently non-serine amino acids and the engineered adeno-associated virus is AAV1, AAV2, AAV3, or AAV6. In some embodiments, an engineered adeno-associated virus includes a sequence of amino acids at positions 154, 155 and 156 of VP1 or at positions 17, 18 and 19 of VP2 that is N-S-S, S-X-S, S-S-Y, N-X-S, N-S-Y, S-X-Y and N-X-Y, where N, X and Y are independently non-serine amino acids and the engineered adeno-associated virus is AAV11. In some embodiments, N, X and Y can be independently selected from alanine or threonine.

In some embodiments, an engineered adeno-associated virus includes a substitution of an amino acid at positions 155, 156 or 157 of VP1 or at positions 18, 19 or 20 of VP2, where the engineered adeno-associated virus is AAV1, AAV2, AAV3, or AAV6. In some embodiments, an engineered adeno-associated virus includes a substitution of an amino acid at positions 154, 155 or 156 of VP1 or at positions 17, 18 or 19 of VP2, where the engineered adeno-associated virus is AAV11. In some embodiments, the substitution is alanine or threonine for serine.

In some embodiments, an engineered adeno-associated virus includes a deletion of at least one amino acid at positions 155, 156 or 157 of VP1 or at positions 18, 19 or 20 of VP2, where the engineered adeno-associated virus is AAV1, AAV2, AAV3, or AAV6. In some embodiments, an engineered adeno-associated virus includes a deletion of at least one amino acid at positions 154, 155 or 156 of VP1 or at positions 17, 18 or 19 of VP2, where the engineered adeno-associated virus is AAV11.

In some embodiments, an engineered adeno-associated virus includes a sequence of amino acids at positions 156, 157 and 158 of VP1 or at positions 19, 20 and 21 of VP2 that is S-S-S, N-S-T, S-X-T, S-S-Y, N-X-T, N-S-Y, S-X-Y, or N-X-Y, where N and X are independently non-serine amino acids and Y is a non-threonine amino acid and the engineered adeno-associated virus is AAV7, AAV8, AAV10. In some embodiments, N and X can be independently selected from alanine and threonine and Y can be threonine.

In some embodiments, an engineered adeno-associated virus includes a substitution of an amino acid at positions 156, 157 or 158 of VP1 or at positions 19, 20 or 21 of VP2, where the engineered adeno-associated virus is AAV7, AAV8 or AAV10. In some embodiments, the substitution is alanine or threonine for serine or alanine for serine or threonine.

In some embodiments, an engineered adeno-associated virus includes a deletion of at least one amino acid at positions 156, 157 or 158 of VP1 or at positions 19, 20 or 21 of VP2, where the engineered adeno-associated virus is AAV7, AAV8 or AAV10.

In some embodiments, an engineered adeno-associated virus includes a sequence of amino acids at positions 154, 155 and 156 of VP1 or at positions 18, 19 and 20 of VP2 that is S-S-S, N-S-T, S-X-T, S-S-Y, N-X-T, N-S-Y, S-X-Y, or N-X-Y, where N and X are independently non-serine amino acids and Y is a non-threonine amino acid and the engineered adeno-associated virus is AAV4. In some embodiments, N and X can be independently selected from alanine and threonine and Y can be threonine.

In some embodiments, an engineered adeno-associated virus includes a substitution of an amino acid at positions 154, 155 or 156 of VP1 or at positions 18, 19 or 20 of VP2, where the engineered adeno-associated virus is AAV4. In some embodiments, the substitution is alanine or threonine for serine or alanine for serine or threonine.

In some embodiments, an engineered adeno-associated virus includes a deletion of at least one amino acid at positions 154, 155 or 156 of VP1 or at positions 18, 19 or 20 of VP2, where the engineered adeno-associated virus is AAV4.

In some embodiments, an engineered adeno-associated virus includes a sequence of amino acids at positions 155, 156 and 157 of VP1 or at positions 18, 19 and 20 of VP2 that is S-S-S, N-S-A, S-X-A, S-S-Y, N-X-A, N-S-Y, S-X-Y, or N-X-Y, where N and X are independently non-serine amino acids and Y is a non-alanine amino acid and the engineered adeno-associated virus is AAV9. In some embodiments, N and X can be independently selected from alanine and threonine and Y can be serine.

In some embodiments, an engineered adeno-associated virus includes a substitution of an amino acid at positions 155, 156 or 157 of VP1 or at positions 18, 19 or 20 of VP2, where the engineered adeno-associated virus is AAV9. In some embodiments, the substitution is alanine or threonine for serine or serine for alanine.

In some embodiments, an engineered adeno-associated virus includes a deletion of at least one amino acid at positions 155, 156 or 157 of VP1 or at positions 18, 19 or 20 of VP2, where the engineered adeno-associated virus is AAV9.

In an embodiment, an engineered adeno-associated virus includes one or more non-naturally occurring amino acid substitutions or deletions at amino acid positions having threonine, lysine, serine, or tyrosine residues in a region between an amino acid at position 130 and an amino acid at position 198 of VP1 or a corresponding region of VP2.

In an embodiment, an engineered adeno-associated virus includes one or more non-naturally occurring amino acid substitutions or insertions of threonine, lysine, serine, or tyrosine residues in a region between an amino acid at position 130 and an amino acid at position 198 of VP1 or a corresponding region of VP2.

In an embodiment, an engineered adeno-associated virus includes at least one of the mutations listed in Table 3 in VP1 or at a corresponding position in VP2.

In some embodiments, an engineered adeno-associated virus with one or more non-naturally occurring amino acid substitutions, insertions or deletions in VP1 or VP2 results in a S/T-rich motif. In some embodiments, the one or more non-naturally occurring amino acid substitutions, insertions or deletions comprises an insertion or deletion of a triple serine (S-S-S) motif. In some embodiments, the one or more non-naturally occurring amino acid substitutions, insertions or deletions results in a PEST domain. In some embodiments, the one or more non-naturally occurring amino acid substitutions, insertions or deletions include insertion of a PEST domain. The PEST domain can be any PEST domain, including a portion thereof. By way of example but not limitation, the PEST domain can be amino acids 149-160 of VP1 of AAV2, PDSSSG (SEQ ID NO: 23) or SPVEPDSSS-GTG (SEQ ID NO: 24). In some embodiments, the one or more non-naturally occurring amino acid substitutions, insertions or deletions include a deletion of a S/T-rich motif or an insertion of a S/T-rich motif or a substitution resulting in a S/T-rich motif. In some embodiments, the S/T-rich motif is a triple serine motif.

In an embodiment, a nucleic acid encoding an engineered VP1 or VP2 peptide includes one or more of a non-naturally occurring amino acid substitution, insertion, or deletion as set forth in Table 3. In some embodiments, a nucleic acid encodes an engineered adeno-associated virus as described in the present disclosure. In some embodiments, a nucleic acid encodes an engineered VP1 or VP2 peptide of an engineered adeno-associated virus as described in the present disclosure. In some embodiments, a nucleic acid molecule comprises a nucleotide sequence selected from the group consisting of SEQ ID NO: 55-78 (VP1 and VP2 for AAV1-AAV12, respectively) with one or more of a non-naturally occurring modification resulting in an amino acid substitution, insertion or deletion in the protein encoded by the nucleic acid molecule, where the amino acid substitution, insertion or deletion is set forth in Table 3 or otherwise set forth in viral embodiments of the present disclosure. Such modifications can include substitutions, insertions or deletions that result in a PEST domain or S/T-rich motif or otherwise affect a PEST domain or S/T-rich motif in VP1 or VP2.

In an embodiment, an engineered VP1 or VP2 peptide includes one or more of a non-naturally occurring amino acid substitution, insertion, or deletion as set forth in Table 3. In some embodiments, an engineered VP1 or VP2 peptide comprises a sequence according to any of the engineered adeno-associated viruses as described in the present disclosure.

In an embodiment, a method if provided for modulating the transduction efficiency of an adeno-associated virus including a step of providing an engineered adeno-associated virus comprising one or more of a non-naturally occurring amino acid substitution, insertion, or deletion according to the present disclosure, including Table 3.

In some embodiments, a mutation can be a substitution of alanine or threonine for serine. In some embodiments, a mutation can be a substation of serine for alanine or threonine.

Viral Synthesis Methods

The insertion, deletion, or substitution mutations described in the present disclosure are within the VP1 or VP2 N-terminal regions between amino acids at positions 130 and 198. Traditional molecular cloning techniques, such as site-directed mutagenesis can be performed to generate AAV capsid mutants. Other methods of producing mutations and AAV viruses are well known to those of skill in the art.

For example, as used in in the examples below, a plasmid (modified pRepCap), along with an ITR-containing transgene plasmid, and helper plasmid with adenovirus proteins can be used for triple plasmid infection in HEK293T cells via polyethylenimine transfection. 48 hours post-transfection, cells are harvested and resuspended in saline buffer. Cells are burst open to release viruses via three freeze-thaw cycles and lysates are separated via ultracentrifugation to separate viruses from all debris and cellular proteins.

In addition, the viruses can be purified to exchange buffer or concentrated for further analysis.

In all examples below, viruses packaged sc-CMV-GFP which encodes GFP as a detectable marker of transduction and expression of the transgene.

EXAMPLES

Example 1: Effect of Deletion or Mutation of the PEST Domain of AAV2 on Transduction Efficiency In order to determine the effect of deletion or mutation of the PEST domain of VP1 and VP2 of AAV2, AAV2 capsid mutants were prepared.

Wild-type AAV2 and AAV2 capsid mutants were prepared via standard viral synthesis and molecular cloning techniques. The viruses were applied to HEK293T cells at a multiplicity of infection (MOI) of 1000 viral genomes per cell. Cells were harvested at 48 hours post-transduction and gene expression was measured using a BD FACS Canto II flow cytometer. The Transduction Index (TI) was determined for each virus by multiplying the % of GFP$^+$ cells by the geometric mean fluorescence intensity.

The specific mutants generated included a deletion mutant where the amino acids from 149-160 in VP1 have been deleted, insertion mutants at amino acid position 154 of VP1 with either arginine (154R), alanine (154A) or aspartic acid (154D), and a substitution mutant where the triple serine motif at amino acids 155-157 of VP1 has been substituted with a triple alanine motif (S155-7A). All mutants were generated to include the mutations in VP1 and at a corresponding position in VP2.

As shown in FIG. 5A, deletion of the amino acids from positions 149-160 in VP1 or insertion of R, A or D residues at amino acid position 154, in the middle of the PEST domain, decreased transduction efficiency significantly (3-4% TI as compared to wild-type). As shown in FIG. 5B, mutation of the triple serine motif at amino acid positions 155-157 to a triple alanine motif (S155-7A) also significantly decreased transduction efficiency.

Example 2: Effect of Substitutions in the Triple Serine Motif of VP1 of AAV2 at Amino Acid Positions 155-157

In order to further assess the effect of substitutions for serine in the triple serine motif, further substitution mutants of AAV2 VP1 and at corresponding positions of VP2 were prepared using standard viral synthesis and molecular cloning techniques. The same GFP transgene as in Example 1 was used and packaged into the viruses. The same methods as in Example 1 for transductions and cell harvesting and analysis were used.

The specific mutants generated included: S155A, S156A, S157A, S156-7A and S155-7A as listed in FIG. 6.

As shown in FIG. 7A, substitution of the serine at amino acid position 155 with alanine resulted in significantly decreased transduction efficiency in both S155A and S155-7A. Transduction efficiency was also substantially reduced in a mutant having only the serine at amino acid position 155 of VP1 (S156-7A). Mutants with a serine at amino acid position 155 of VP1 and at least one serine at amino acid position 156 or 157 of VP1 had transduction efficiencies indistinguishable from the wild-type virus (S156A and S157A).

These results demonstrate that the serine at amino acid position 155 in VP1 of AAV2 is essential for wild-type levels of transduction in addition to at least one of the serines at amino acid position 156 or 157 of AAV2 VP1. Thus, the triple serine motif (S-S-S) behaves like an OR-AND-GATE as shown in FIG. 7B, either the S156 or S157 is required AND the S155 residue must be present for wild-type transduction to occur. As shown in FIG. 8, the S/T-rich region, in this case a S-S-S motif is surrounded by basic regions—BR1, BR2 and BR3—ablation of which results in decreased transduction, further confirming the importance of the S/T-rich region, in this case S-S-S, in transduction.

Example 3: Additional AAV2 VP1 Mutants and Their Effect on Transduction Efficiency Additional mutations in VP1 of AAV2 were also investigated for their effect on transduction efficiency. Following the procedures of Examples 1-2, the following substitution mutants were generated: S149A, P150A, P153A, P150A_P153A and T159A. The mutants prepared included mutations at corresponding positions of VP2 in addition to the mutations in VP1. These mutants were compared with the wild-type AAV2 and the previously investigated mutants: del149-160, 154R, 154A, 154D, S155A and S155-7A.

In addition, alanine scanning mutants were prepared by substituting each amino acid from amino acid positions 147-161 of AAV2 VP1, as follows: E147A, H148A S149A, P150A, V151A, E152A, P153A, D154A, S155A, S156A, S157A, G158A, T159A, G160A, K161A The mutants prepared included mutations at corresponding positions of VP2 in addition to mutations in VP1.

As shown in FIG. 9, P150A, P153A, P150A_P153A and T159A reduced transduction efficiency although not as drastically as del149-160, 154R, 154A, 154D, S155A and S155-7A. These results demonstrate that the transduction efficiency of the virus can be modulated by mutations within the PEST domain.

As shown in FIG. 10, the alanine scanning mutants provided a wide range of normalized transduction efficiency, permitting modulation of transduction efficiency by mutations beyond those in the triple serine motif. H148A, in particular, significantly increased transduction efficiency while D154A and G158A resulted in nearly 10-fold lower transduction efficiency than for wild-type AAV2.

Example 4: Effect of Mutation of VP1 of AAV9 on Transduction Efficiency, In Vitro and In Vivo Mutations of VP1 in AAV9 were investigated for their effect on transduction efficiency. AAV9 has a S-S-A motif in its putative PEST domain and is known to have lower transduction efficiency than AAV2. Using the methods of the foregoing examples, AAV9 mutants were prepared with mutations in VP1 at S155, S156 or A157 and at corresponding positions of VP2. In addition to transduction in HEK293T cells, CHO-Lec2 cells were also transduced, harvested and analyzed using the same methods as in Example 1. The partial sequence alignment of AAV9 VP1 with other AAV serotypes according AAV2 VP1 numbering is shown in FIG. 11A and the mutations made to VP1 of AAV9 are shown in FIG. 11B.

As shown in FIG. 12, mutation of the S-S-A sequence in AAV9 VP1 to S-S-S results in a substantial increase in transduction efficiency, while mutations resulting in A-S-A, S-S-T and A-S-S sequences did not differ significantly from wild-type AAV9 in transduction efficiency. This effect is even more pronounced in CHO-Lec2 cells as shown in FIG. 11C. These results demonstrate that the S-S-S-motif can improve transduction efficiency in AAV9 which naturally has a S-S-A motif.

To confirm this effect, wild-type AAV9 or AAV9 with a A157S substitution in VP1 and at a corresponding position in VP2 were injected into mice at a dose of $5 \times 10^{10}$ viral genomes per mouse via tail-vein i.v. injection. After 1 week, mice were sacrificed and mRNA was harvested from several organs to measure biodistribution using RT-PCR. As shown in FIGS. 13A and 13B, in nearly every organ, the mutant AAV9 demonstrated increased transduction as compared to wild-type, significantly in heart tissue. These results confirm that the A157S mutant of AAV9 VP1 improves transduction efficiency of AAV9 in vivo in addition to in vitro.

Example 5: Effect of Deletion of Arginine at Amino Acid Position 152 (152R) in VP1 of AAV8

AAV8 lacks a naturally occurring PEST domain corresponding to the PEST domain in AAV2 because it has a charged arginine residue at amino acid position 152 of VP1. To assess the effect of deletion of this residue, thus resulting in a PEST domain (PEST score of 9.16) in AAV8, a mutant AAV8 was prepared with a deletion of the arginine at amino acid position 152 in VP1 and at a corresponding position in VP2.

The virus was transduced into HEK293T cells as described in Example 1. Wild-type AAV8 was used as a control. As shown in FIG. 14, the transduction index of the del152R mutant was increased 2.6-fold over that of wild-type AAV2, further supporting that the PEST domain in AAV viral capsid proteins is important for transduction.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated.

What is claimed is:

1. An engineered adeno-associated virus comprising one or more non-naturally occurring amino acid substitutions, insertions or deletions in the VP1 capsid, wherein the VP1 capsid comprises a sequence selected from the group consisting of SEQ ID NOS: 2, 3, 4, 5, 6, 10, and 11, wherein
   i) when the VP1 capsid comprises the sequence of SEQ ID NOS: 2, 3, 4, 5, or 6, the one or more non-naturally occurring amino acid substitutions, insertions or deletions of the VP1 capsid is at positions 155, 156, and 157 of the sequence, or ii) when the VP1 capsid comprises the sequence of SEQ ID NOS: 10 or 11, the one or more non-naturally occurring amino acid substitutions, insertions or deletions of the VP1 capsid is at positions 154, 155 and 156 of the sequence.

2. The engineered adeno-associated virus of claim 1, wherein: (1) when the sequence is any one of SEQ ID NOS: 2-5, positions 155, 156, and 157 have an amino acid sequence selected from the group consisting of N-S-S, S-X-S, S-S-Y, N-X-S, N-S-Y, S-X-Y, and N-X-Y, wherein N, X and Y are independently non-serine amino acids; and (2) when the sequence is SEQ ID NO: 6, positions 155, 156, and 157 have an amino acid sequence selected from the group consisting of S-S-S, N-S-A, S-X-A, S-S-Y, N-X-A, N-S-Y, S-X-Y, or N-X-Y, wherein N and X are independently non-serine amino acids, and wherein Y is a non-alanine amino acid.

3. The engineered adeno-associated virus of claim 2, wherein: (1) when the sequence is any one of SEQ ID NOS: 2-5, then N, X and Y are independently selected from the group consisting of alanine (A) and threonine (T); and (2) when the sequence is SEQ ID NO: 6, then N and X are independently selected from the group consisting of alanine (A) and threonine (T), and Y is serine.

4. The engineered adeno-associated virus of claim 1, wherein: (1) when the sequence is SEQ ID NO: 11, positions 154, 155, and 156 have an amino acid sequence selected from the group consisting of N-S-S, S-X-S, S-S-Y, N-X-S, N-S-Y, S-X-Y, and N-X-Y, wherein N, X and Y are independently non-serine amino acids; and (2) when the sequence is SEQ ID NO: 10, positions 154, 155, and 156 have an amino acid sequence selected from the group consisting of S-S-S, N-S-T, S-X-T, S-S-Y, N-X-T, N-S-Y, S-X-Y, or N-X-Y, wherein N and X are independently non-serine amino acids, and wherein Y is a non-threonine amino acid.

5. The engineered adeno-associated virus of claim 4, wherein: (1) when the sequence is SEQ ID NO: 11, then N, X and Y are independently selected from the group consisting of alanine (A) and threonine (T); and (2) when the sequence is SEQ ID NO: 10, then N and X are independently selected from the group consisting of alanine (A) and threonine (T), and wherein Y is alanine.

6. An engineered adeno-associated virus, comprising one or more non-naturally occurring amino acid substitutions, insertions or deletions in the VP2 capsid, wherein the VP2 capsid comprises a sequence selected from the group consisting of SEQ ID NOS: 43, 44, 45, 46, 48, 49, 50, 51, 52 and 53, i) wherein the one or more amino acid substitutions, insertions or deletions of the VP2 capsid is at positions 18, 19, and 20 of the sequence when the VP2 capsid comprises the sequence of SEQ ID NOS: 43, 44, 45, 46, 48 or 51, ii) wherein the one or more amino acid substitutions, insertions or deletions of the VP2 capsid is at positions 19, 20 and 21 of the sequence when the VP2 capsid comprises the sequence of SEQ ID NOS: 49, 50 or 52, and wherein the one or more amino acid substitutions, insertions or deletions of the VP2 capsid is at positions 17, 18 and 19 of the sequence when the VP2 capsid comprises the sequence of SEQ ID NO: 53.

7. The engineered adeno-associated virus of claim 6, wherein: (1) when the sequence is any one of SEQ ID NOS: 43-45 and 48, positions 18, 19, and 20 have an amino acid sequence selected from the group consisting of N-S-S, S-X-S, S-S-Y, N-X-S, N-S-Y, S-X-Y, and N-X-Y, wherein N, X and Y are independently non-serine amino acids; (2) when the sequence is SEQ ID NO: 51, positions 18, 19, and 20 have an amino acid sequence selected from the group consisting of S-S-S, N-S-A, S-X-A, S-S-Y, N-X-A, N-S-Y, S-X-Y, or N-X-Y, wherein N and X are independently non-serine amino acids, and wherein Y is a non-alanine amino acid; and (3) when the sequence is SEQ ID NO: 46, positions 18, 19, and 20 have an amino acid sequence selected from the group consisting of S-S-S, N-S-T, S-X-T, S-S-Y, N-X-T, N-S-Y, S-X-Y, or N-X-Y, wherein N and X are independently non-serine amino acids, and wherein Y is a non-threonine amino acid.

8. The engineered adeno-associated virus of claim 7, wherein: (1) when the sequence is any one of SEQ ID NOS: 43-45 and 48, then N, X and Y are independently selected from the group consisting of alanine (A) and threonine (T); (2) when the sequence is SEQ ID NO: 46, then N and X are independently selected from the group consisting of alanine (A) and threonine (T), and wherein Y is alanine; and (3) when the sequence is SEQ ID NO: 51, then N and X are independently selected from the group consisting of alanine (A) and threonine (T) and Y is serine.

9. The engineered adeno-associated virus of claim 6, wherein the VP2 capsid comprises the sequence of SEQ ID NO: 53, and wherein positions 17, 18, and 19 have an amino acid sequence selected from the group consisting of N-S-S, S-X-S, S-S-Y, N-X-S, N-S-Y, S-X-Y, and N-X-Y, wherein N, X and Y are independently non-serine amino acids.

10. The engineered adeno-associated virus of claim 9, wherein N, X and Y are independently selected from the group consisting of alanine (A) and threonine (T).

11. An engineered adeno-associated virus comprising one or more non-naturally occurring amino acid substitutions, insertions or deletions in the VP1 capsid, wherein the VP1 capsid comprises a sequence selected from the group consisting of SEQ ID NOS: 7, 8, and 9, and wherein the one or more non-naturally occurring amino acid substitutions, insertions or deletions in the VP1 capsid is at positions 156, 157 and 158 of the sequence.

12. The engineered adeno-associated virus of claim 11, wherein positions 156, 157, and 158 have an amino acid sequence selected from the group consisting of S-S-S, N-S-T, S-X-T, S-S-Y, N-X-T, N-S-Y, S-X-Y, or N-X-Y, wherein N and X are independently non-serine amino acids, and wherein Y is a non-threonine amino acid.

13. The engineered adeno-associated virus of claim 12, wherein N and X are independently selected from the group consisting of alanine (A) and threonine (T), and wherein Y is alanine.

14. The engineered adeno-associated virus of claim 6, wherein the VP2 capsid comprises the sequence of SEQ ID NO: 49, 50 or 52, and wherein positions 19, 20 and 21 have an amino acid sequence selected from the group consisting of S-S-S, N-S-T, S-X-T, S-S-Y, N-X-T, N-S-Y, S-X-Y, or N-X-Y, wherein N and X are independently non-serine amino acids, and wherein Y is a non-threonine amino acid.

15. The engineered adeno-associated virus of claim 14, wherein N and X are independently selected from the group consisting of alanine (A) and threonine (T), and wherein Y is alanine.

* * * * *

SEQUENCE LISTING

<160> NUMBER OF SEQ ID NOS: 78

<210> SEQ ID NO 1
<211> LENGTH: 724
<212> TYPE: PRT
<213> ORGANISM: Adeno-associated virus

<400> SEQUENCE: 1

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
```

```
                        325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
                355                 360                 365
Ala Thr Leu Asn Arg Asp Asn Thr Glu Asn Pro Thr Glu Arg Ser Ser
            370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
                420                 425                 430
Gln Tyr Leu Tyr Arg Phe Val Ser Thr Asn Asn Thr Gly Gly Val Gln
                435                 440                 445
Phe Asn Lys Asn Leu Ala Gly Arg Tyr Ala Asn Thr Tyr Lys Asn Trp
            450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
                500                 505                 510
Asn Asn Leu Gln Gly Ser Asn Thr Tyr Ala Leu Glu Asn Thr Met Ile
            515                 520                 525
Phe Asn Ser Gln Pro Ala Asn Pro Gly Thr Thr Ala Thr Tyr Leu Glu
            530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
                580                 585                 590
Gly Ser Val Trp Met Glu Arg Asp Val Tyr Leu Gln Gly Pro Ile Trp
            595                 600                 605
Ala Lys Ile Pro Glu Thr Gly Ala His Phe His Pro Ser Pro Ala Met
            610                 615                 620
Gly Gly Phe Gly Leu Lys His Pro Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
                660                 665                 670
Trp Glu Leu Lys Lys Glu Asn Ser Lys Arg Trp Asn Pro Glu Ile Gln
            675                 680                 685
Tyr Thr Asn Asn Tyr Asn Asp Pro Gln Phe Val Asp Phe Ala Pro Asp
            690                 695                 700
Ser Thr Gly Glu Tyr Arg Thr Thr Arg Pro Ile Gly Thr Arg Tyr Leu
705                 710                 715                 720
Thr Arg Pro Leu

<210> SEQ ID NO 2
<211> LENGTH: 736
```

<212> TYPE: PRT
<213> ORGANISM: Adeno-associated virus

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

```
Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 3
<211> LENGTH: 736
<212> TYPE: PRT
<213> ORGANISM: Adeno-associated virus

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
```

```
                35                  40                  45
Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460
```

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
    515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 735
<212> TYPE: PRT
<213> ORGANISM: Adeno-associated virus

<400> SEQUENCE: 4

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly

```
                100             105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
            130                 135             140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
            450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
```

-continued

```
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Ile Arg Thr Thr Asn Pro Val Ala Thr Glu Gln Tyr
            565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
            610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
            645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
            725                 730                 735

<210> SEQ ID NO 5
<211> LENGTH: 736
<212> TYPE: PRT
<213> ORGANISM: Adeno-associated virus

<400> SEQUENCE: 5

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Val Pro Gln Pro
            20                  25                  30
Lys Ala Asn Gln Gln His Gln Asp Asn Arg Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Ile Leu Glu Pro
        115                 120                 125
Leu Gly Leu Val Glu Glu Ala Ala Lys Thr Ala Pro Gly Lys Lys Gly
    130                 135                 140
Ala Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
```

-continued

```
                165                 170                 175
Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590
```

```
Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 6
<211> LENGTH: 736
<212> TYPE: PRT
<213> ORGANISM: Adeno-associated virus

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

-continued

```
            225                 230                 235                 240
        Thr Thr Ser Thr Arg Thr Trp Ala Leu Pro Thr Tyr Asn Asn His Leu
                        245                 250                 255
        Tyr Lys Gln Ile Ser Asn Ser Thr Ser Gly Gly Ser Ser Asn Asp Asn
                        260                 265                 270
        Ala Tyr Phe Gly Tyr Ser Thr Pro Trp Gly Tyr Phe Asp Phe Asn Arg
                        275                 280                 285
        Phe His Cys His Phe Ser Pro Arg Asp Trp Gln Arg Leu Ile Asn Asn
                        290                 295                 300
        Asn Trp Gly Phe Arg Pro Lys Arg Leu Asn Phe Lys Leu Phe Asn Ile
        305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Pro Phe Pro
                        355                 360                 365
        Ala Asp Val Phe Met Ile Pro Gln Tyr Gly Tyr Leu Thr Leu Asn Asp
                        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Ser
        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
        Tyr Gly Gln Val Ala Thr Asn His Gln Ser Ala Gln Ala Gln Ala Gln
                        580                 585                 590
        Thr Gly Trp Val Gln Asn Gln Gly Ile Leu Pro Gly Met Val Trp Gln
                        595                 600                 605
        Asp Arg Asp Val Tyr Leu Gln Gly Pro Ile Trp Ala Lys Ile Pro His
                        610                 615                 620
        Thr Asp Gly Asn Phe His Pro Ser Pro Leu Met Gly Gly Phe Gly Met
        625                 630                 635                 640
        Lys His Pro Pro Pro Gln Ile Leu Ile Lys Asn Thr Pro Val Pro Ala
                        645                 650                 655
```

-continued

Asp Pro Pro Thr Ala Phe Asn Lys Asp Lys Leu Asn Ser Phe Ile Thr
              660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 737
<212> TYPE: PRT
<213> ORGANISM: Adeno-associated virus

<400> SEQUENCE: 7

Met Ala Ala Asp Gly Tyr Leu Pro Asp Trp Leu Glu Asp Asn Leu Ser
1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn

```
            290                 295                 300
Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                    325                 330                 335

Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                    405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
                515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720
```

Val Tyr Ser Glu Pro Arg Pro Ile Gly Thr Arg Tyr Leu Thr Arg Asn
                725                 730                 735

Leu

<210> SEQ ID NO 8
<211> LENGTH: 738
<212> TYPE: PRT
<213> ORGANISM: Adeno-associated virus

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
           355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 9
<211> LENGTH: 738
<212> TYPE: PRT

<213> ORGANISM: Adeno-associated virus

<400> SEQUENCE: 9

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Ala Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Glu Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
```

```
Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 10
<211> LENGTH: 734
<212> TYPE: PRT
<213> ORGANISM: Adeno-associated virus

<400> SEQUENCE: 10

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30
```

-continued

Ala Asn Gln Gln His Gln Asp Asn Ala Arg Gly Leu Val Leu Pro Gly
             35                  40                  45

Tyr Lys Tyr Leu Gly Pro Gly Asn Gly Leu Asp Lys Gly Glu Pro Val
 50                  55                  60

Asn Ala Ala Asp Ala Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn

```
        450                 455                 460
Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
                580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His Leu
                725                 730

<210> SEQ ID NO 11
<211> LENGTH: 733
<212> TYPE: PRT
<213> ORGANISM: Adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
```

```
            515                 520                 525
Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 12
<211> LENGTH: 742
<212> TYPE: PRT
<213> ORGANISM: Adeno-associated virus

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160
```

-continued

Ala Pro Ala Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365

Val Phe Met Val Pro Gln Tyr Gly Tyr Cys Gly Val Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Ile Ala Thr Asn
                565                 570                 575

Pro Arg Asp Thr Asp Met Phe Gly Gln Ile Ala Asp Asn Asn Gln Asn

-continued

```
                    580             585             590
        Ala Thr Thr Ala Pro His Ile Ala Asn Leu Asp Ala Met Gly Ile Val
                        595                 600                 605

Pro Gly Met Val Trp Gln Asn Arg Asp Ile Tyr Tyr Gln Gly Pro Ile
                    610                 615                 620

Trp Ala Lys Val Pro His Thr Asp Gly His Phe His Pro Ser Pro Leu
        625                 630                 635                 640

Met Gly Gly Phe Gly Leu Lys His Pro Pro Gln Ile Phe Ile Lys
                        645                 650                 655

Asn Thr Pro Val Pro Ala Asn Pro Asn Thr Thr Phe Ser Ala Ala Arg
                    660                 665                 670

Ile Asn Ser Phe Leu Thr Gln Tyr Ser Thr Gly Gln Val Ala Val Gln
                    675                 680                 685

Ile Asp Trp Glu Ile Gln Lys Glu His Ser Lys Arg Trp Asn Pro Glu
                690                 695                 700

Val Gln Phe Thr Ser Asn Tyr Gly Thr Gln Asn Ser Met Leu Trp Ala
        705                 710                 715                 720

Pro Asp Asn Ala Gly Asn Tyr His Glu Leu Arg Ala Ile Gly Ser Arg
                        725                 730                 735

Phe Leu Thr His His Leu
                        740

<210> SEQ ID NO 13
<211> LENGTH: 18
<212> TYPE: PRT
<213> ORGANISM: Adeno-associated virus

<400> SEQUENCE: 13

Arg Pro Val Glu Gln Ser Pro Gln Glu Pro Asp Ser Ser Ser Gly Ile
1               5                   10                  15

Gly Lys

<210> SEQ ID NO 14
<211> LENGTH: 14
<212> TYPE: PRT
<213> ORGANISM: Adeno-associated virus

<400> SEQUENCE: 14

His Ser Pro Val Glu Pro Asp Ser Ser Ser Gly Thr Gly Lys
1               5                   10

<210> SEQ ID NO 15
<211> LENGTH: 19
<212> TYPE: PRT
<213> ORGANISM: Adeno-associated virus

<400> SEQUENCE: 15

Lys Gly Ala Val Asp Gln Ser Pro Gln Glu Pro Asp Ser Ser Ser Gly
1               5                   10                  15

Val Gly Lys

<210> SEQ ID NO 16
<211> LENGTH: 18
<212> TYPE: PRT
<213> ORGANISM: Adeno-associated virus

<400> SEQUENCE: 16

Arg Pro Leu Ile Glu Ser Pro Gln Gln Pro Asp Ser Ser Thr Gly Ile
1               5                   10                  15
```

Gly Lys

```
<210> SEQ ID NO 17
<211> LENGTH: 18
<212> TYPE: PRT
<213> ORGANISM: Adeno-associated virus

<400> SEQUENCE: 17
```

Arg Pro Val Glu Gln Ser Pro Gln Glu Pro Asp Ser Ser Ser Gly Ile
1               5                   10                  15

Gly Lys

```
<210> SEQ ID NO 18
<211> LENGTH: 18
<212> TYPE: PRT
<213> ORGANISM: Adeno-associated virus

<400> SEQUENCE: 18
```

Arg Pro Val Glu Gln Ser Pro Gln Glu Pro Asp Ser Ser Ala Gly Ile
1               5                   10                  15

Gly Lys

```
<210> SEQ ID NO 19
<211> LENGTH: 17
<212> TYPE: PRT
<213> ORGANISM: Adeno-associated virus

<400> SEQUENCE: 19
```

Arg Pro Leu Glu Ser Pro Gln Glu Pro Asp Ser Ser Ser Gly Ile Gly
1               5                   10                  15

Lys

```
<210> SEQ ID NO 20
<211> LENGTH: 30
<212> TYPE: PRT
<213> ORGANISM: Adeno-associated virus

<400> SEQUENCE: 20
```

Lys Leu Val Phe Glu Asp Glu Thr Gly Ala Gly Asp Gly Pro Pro Glu
1               5                   10                  15

Gly Ser Thr Ser Gly Ala Met Ser Asp Asp Ser Glu Met Arg
            20                  25                  30

```
<210> SEQ ID NO 21
<211> LENGTH: 30
<212> TYPE: PRT
<213> ORGANISM: Adeno-associated virus

<400> SEQUENCE: 21
```

Arg Leu Asn Phe Glu Glu Asp Thr Gly Ala Gly Asp Gly Pro Pro Glu
1               5                   10                  15

Gly Ser Asp Thr Ser Ala Met Ser Ser Asp Ile Glu Met Arg
            20                  25                  30

```
<210> SEQ ID NO 22
<211> LENGTH: 26
<212> TYPE: PRT
<213> ORGANISM: Adeno-associated virus

<400> SEQUENCE: 22
```

Arg Thr Leu Asp Phe Glu Asp Ser Gly Ala Gly Asp Gly Pro Pro Glu

```
                1               5                  10                  15
Gly Ser Ser Ser Ser Gly Glu Met Ser His
            20                  25
```

<210> SEQ ID NO 23
<211> LENGTH: 6
<212> TYPE: PRT
<213> ORGANISM: Adeno-associated virus

<400> SEQUENCE: 23

```
Pro Asp Ser Ser Ser Gly
1               5
```

<210> SEQ ID NO 24
<211> LENGTH: 12
<212> TYPE: PRT
<213> ORGANISM: Adeno-associated virus

<400> SEQUENCE: 24

```
Ser Pro Val Glu Pro Asp Ser Ser Ser Gly Thr Gly
1               5                   10
```

<210> SEQ ID NO 25
<211> LENGTH: 41
<212> TYPE: PRT
<213> ORGANISM: Adeno-associated virus

<400> SEQUENCE: 25

```
Glu Pro Val Lys Thr Ala Pro Gly Lys Lys Arg Pro Val Glu His Ser
1               5                   10                  15

Pro Val Glu Pro Asp Ser Ser Ser Gly Thr Gly Lys Ala Gly Gln Gln
            20                  25                  30

Pro Ala Arg Lys Arg Leu Asn Phe Gly
            35                  40
```

<210> SEQ ID NO 26
<211> LENGTH: 40
<212> TYPE: PRT
<213> ORGANISM: Adeno-associated virus

<400> SEQUENCE: 26

```
Glu Gly Ala Lys Thr Ala Pro Gly Lys Lys Arg Pro Leu Glu Ser Pro
1               5                   10                  15

Gln Glu Pro Asp Ser Ser Ser Gly Ile Gly Lys Lys Gly Lys Gln Pro
            20                  25                  30

Ala Arg Lys Arg Leu Asn Phe Glu
            35                  40
```

<210> SEQ ID NO 27
<211> LENGTH: 41
<212> TYPE: PRT
<213> ORGANISM: Adeno-associated virus

<400> SEQUENCE: 27

```
Gln Ala Gly Glu Thr Ala Pro Gly Lys Lys Arg Pro Leu Ile Glu Ser
1               5                   10                  15

Pro Gln Gln Pro Asp Ser Ser Thr Gly Ile Gly Lys Lys Gly Lys Gln
            20                  25                  30

Pro Ala Lys Lys Lys Leu Val Phe Glu
            35                  40
```

<210> SEQ ID NO 28
<211> LENGTH: 41
<212> TYPE: PRT
<213> ORGANISM: Adeno-associated virus

<400> SEQUENCE: 28

Glu Gly Ala Lys Thr Ala Pro Gly Lys Lys Arg Pro Val Glu Gln Ser
1               5                   10                  15

Pro Gln Glu Pro Asp Ser Ser Ser Gly Ile Gly Lys Thr Gly Gln Gln
            20                  25                  30

Pro Ala Lys Lys Arg Leu Asn Phe Gly
        35                  40

<210> SEQ ID NO 29
<211> LENGTH: 41
<212> TYPE: PRT
<213> ORGANISM: Adeno-associated virus

<400> SEQUENCE: 29

Glu Gly Ala Lys Thr Ala Pro Gly Lys Lys Arg Pro Val Glu Gln Ser
1               5                   10                  15

Pro Gln Glu Pro Asp Ser Ser Ser Gly Ile Gly Lys Thr Gly Gln Gln
            20                  25                  30

Pro Ala Lys Lys Arg Leu Asn Phe Gly
        35                  40

<210> SEQ ID NO 30
<211> LENGTH: 42
<212> TYPE: PRT
<213> ORGANISM: Adeno-associated virus

<400> SEQUENCE: 30

Glu Gly Ala Lys Thr Ala Pro Gly Lys Lys Arg Pro Val Glu Pro Ser
1               5                   10                  15

Pro Gln Arg Ser Pro Asp Ser Ser Thr Gly Ile Gly Lys Lys Gly Gln
            20                  25                  30

Gln Pro Ala Arg Lys Arg Leu Asn Phe Gly
        35                  40

<210> SEQ ID NO 31
<211> LENGTH: 42
<212> TYPE: PRT
<213> ORGANISM: Adeno-associated virus

<400> SEQUENCE: 31

Glu Ala Ala Lys Thr Ala Pro Gly Lys Lys Arg Pro Val Glu Pro Ser
1               5                   10                  15

Pro Gln Arg Ser Pro Asp Ser Ser Thr Gly Ile Gly Lys Lys Gly Gln
            20                  25                  30

Gln Pro Ala Lys Lys Arg Leu Asn Phe Gly
        35                  40

<210> SEQ ID NO 32
<211> LENGTH: 42
<212> TYPE: PRT
<213> ORGANISM: Adeno-associated virus

<400> SEQUENCE: 32

Glu Gly Ala Lys Thr Ala Pro Ala Lys Lys Arg Pro Val Glu Pro Ser
1               5                   10                  15

Pro Gln Arg Ser Pro Asp Ser Ser Thr Gly Ile Gly Lys Lys Gly Gln 20                  25                  30

Gln Pro Ala Arg Lys Arg Leu Asn Phe Gly
        35                  40

<210> SEQ ID NO 33
<211> LENGTH: 41
<212> TYPE: PRT
<213> ORGANISM: Adeno-associated virus

<400> SEQUENCE: 33

Glu Ala Ala Lys Thr Ala Pro Gly Lys Lys Arg Pro Val Glu Gln Ser
1               5                   10                  15

Pro Gln Glu Pro Asp Ser Ser Ala Gly Ile Gly Lys Ser Gly Ala Gln
            20                  25                  30

Pro Ala Lys Lys Arg Leu Asn Phe Gly
        35                  40

<210> SEQ ID NO 34
<211> LENGTH: 5
<212> TYPE: PRT
<213> ORGANISM: Adeno-associated virus

<400> SEQUENCE: 34

Asp Ser Ser Ser Gly
1               5

<210> SEQ ID NO 35
<211> LENGTH: 5
<212> TYPE: PRT
<213> ORGANISM: Adeno-associated virus

<400> SEQUENCE: 35

Asp Ser Ser Ser Gly
1               5

<210> SEQ ID NO 36
<211> LENGTH: 5
<212> TYPE: PRT
<213> ORGANISM: Adeno-associated virus

<400> SEQUENCE: 36

Asp Ser Ser Thr Gly
1               5

<210> SEQ ID NO 37
<211> LENGTH: 5
<212> TYPE: PRT
<213> ORGANISM: Adeno-associated virus

<400> SEQUENCE: 37

Asp Ser Ser Ser Gly
1               5

<210> SEQ ID NO 38
<211> LENGTH: 5
<212> TYPE: PRT
<213> ORGANISM: Adeno-associated virus

<400> SEQUENCE: 38

Asp Ser Ser Ser Gly
1               5

<210> SEQ ID NO 39

```
<211> LENGTH: 5
<212> TYPE: PRT
<213> ORGANISM: Adeno-associated virus

<400> SEQUENCE: 39

Asp Ser Ser Thr Gly
1               5

<210> SEQ ID NO 40
<211> LENGTH: 5
<212> TYPE: PRT
<213> ORGANISM: Adeno-associated virus

<400> SEQUENCE: 40

Asp Ser Ser Thr Gly
1               5

<210> SEQ ID NO 41
<211> LENGTH: 5
<212> TYPE: PRT
<213> ORGANISM: Adeno-associated virus

<400> SEQUENCE: 41

Asp Ser Ser Thr Gly
1               5

<210> SEQ ID NO 42
<211> LENGTH: 5
<212> TYPE: PRT
<213> ORGANISM: Adeno-associated virus

<400> SEQUENCE: 42

Asp Ser Ser Ala Gly
1               5

<210> SEQ ID NO 43
<211> LENGTH: 599
<212> TYPE: PRT
<213> ORGANISM: Adeno-associated virus

<400> SEQUENCE: 43

Thr Ala Pro Gly Lys Lys Arg Pro Val Glu Gln Ser Pro Gln Glu Pro
1               5                   10                  15

Asp Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
            35                  40                  45

Gln Pro Leu Gly Glu Pro Pro Ala Thr Pro Ala Ala Val Gly Pro Thr
        50                  55                  60

Thr Met Ala Ser Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160
```

-continued

```
Gln Arg Leu Ile Asn Asn Asn Trp Gly Phe Arg Pro Lys Arg Leu Asn
                165                 170                 175
Phe Lys Leu Phe Asn Ile Gln Val Lys Glu Val Thr Thr Asn Asp Gly
            180                 185                 190
Val Thr Thr Ile Ala Asn Asn Leu Thr Ser Thr Val Gln Val Phe Ser
        195                 200                 205
Asp Ser Glu Tyr Gln Leu Pro Tyr Val Leu Gly Ser Ala His Gln Gly
    210                 215                 220
Cys Leu Pro Pro Phe Pro Ala Asp Val Phe Met Ile Pro Gln Tyr Gly
225                 230                 235                 240
Tyr Leu Thr Leu Asn Asn Gly Ser Gln Ala Val Gly Arg Ser Ser Phe
                245                 250                 255
Tyr Cys Leu Glu Tyr Phe Pro Ser Gln Met Leu Arg Thr Gly Asn Asn
            260                 265                 270
Phe Thr Phe Ser Tyr Thr Phe Glu Glu Val Pro Phe His Ser Ser Tyr
        275                 280                 285
Ala His Ser Gln Ser Leu Asp Arg Leu Met Asn Pro Leu Ile Asp Gln
    290                 295                 300
Tyr Leu Tyr Tyr Leu Asn Arg Thr Gln Asn Gln Ser Gly Ser Ala Gln
305                 310                 315                 320
Asn Lys Asp Leu Leu Phe Ser Arg Gly Ser Pro Ala Gly Met Ser Val
                325                 330                 335
Gln Pro Lys Asn Trp Leu Pro Gly Pro Cys Tyr Arg Gln Gln Arg Val
            340                 345                 350
Ser Lys Thr Lys Thr Asp Asn Asn Ser Asn Phe Thr Trp Thr Gly
                355                 360                 365
Ala Ser Lys Tyr Asn Leu Asn Gly Arg Glu Ser Ile Ile Asn Pro Gly
    370                 375                 380
Thr Ala Met Ala Ser His Lys Asp Asp Glu Asp Lys Phe Phe Pro Met
385                 390                 395                 400
Ser Gly Val Met Ile Phe Gly Lys Glu Ser Ala Gly Ala Ser Asn Thr
                405                 410                 415
Ala Leu Asp Asn Val Met Ile Thr Asp Glu Glu Glu Ile Lys Ala Thr
            420                 425                 430
Asn Pro Val Ala Thr Glu Arg Phe Gly Thr Val Ala Val Asn Phe Gln
        435                 440                 445
Ser Ser Ser Thr Asp Pro Ala Thr Gly Asp Val His Ala Met Gly Ala
    450                 455                 460
Leu Pro Gly Met Val Trp Gln Asp Arg Asp Val Tyr Leu Gln Gly Pro
465                 470                 475                 480
Ile Trp Ala Lys Ile Pro His Thr Asp Gly His Phe His Pro Ser Pro
                485                 490                 495
Leu Met Gly Gly Phe Gly Leu Lys Asn Pro Pro Pro Gln Ile Leu Ile
            500                 505                 510
Lys Asn Thr Pro Val Pro Ala Asn Pro Ala Glu Phe Ser Ala Thr
        515                 520                 525
Lys Phe Ala Ser Phe Ile Thr Gln Tyr Ser Thr Gly Gln Val Ser Val
    530                 535                 540
Glu Ile Glu Trp Glu Leu Gln Lys Glu Asn Ser Lys Arg Trp Asn Pro
545                 550                 555                 560
Glu Val Gln Tyr Thr Ser Asn Tyr Ala Lys Ser Ala Asn Val Asp Phe
                565                 570                 575
```

```
Thr Val Asp Asn Asn Gly Leu Tyr Thr Glu Pro Arg Pro Ile Gly Thr
            580                 585                 590

Arg Tyr Leu Thr Arg Pro Leu
        595
```

<210> SEQ ID NO 44
<211> LENGTH: 598
<212> TYPE: PRT
<213> ORGANISM: Adeno-associated virus

<400> SEQUENCE: 44

```
Thr Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350
```

-continued

```
Lys Thr Ser Ala Asp Asn Asn Ser Glu Tyr Ser Trp Thr Gly Ala
        355                 360                 365
Thr Lys Tyr His Leu Asn Gly Arg Asp Ser Leu Val Asn Pro Gly Pro
    370                 375                 380
Ala Met Ala Ser His Lys Asp Asp Glu Glu Lys Phe Phe Pro Gln Ser
385                 390                 395                 400
Gly Val Leu Ile Phe Gly Lys Gln Gly Ser Glu Lys Thr Asn Val Asp
                405                 410                 415
Ile Glu Lys Val Met Ile Thr Asp Glu Glu Ile Arg Thr Thr Asn
            420                 425                 430
Pro Val Ala Thr Glu Gln Tyr Gly Ser Val Ser Thr Asn Leu Gln Arg
                435                 440                 445
Gly Asn Arg Gln Ala Ala Thr Ala Asp Val Asn Thr Gln Gly Val Leu
        450                 455                 460
Pro Gly Met Val Trp Gln Asp Arg Asp Val Tyr Leu Gln Gly Pro Ile
465                 470                 475                 480
Trp Ala Lys Ile Pro His Thr Asp Gly His Phe His Pro Ser Pro Leu
                485                 490                 495
Met Gly Gly Phe Gly Leu Lys His Pro Pro Pro Gln Ile Leu Ile Lys
            500                 505                 510
Asn Thr Pro Val Pro Ala Asn Pro Ser Thr Thr Phe Ser Ala Ala Lys
        515                 520                 525
Phe Ala Ser Phe Ile Thr Gln Tyr Ser Thr Gly Gln Val Ser Val Glu
530                 535                 540
Ile Glu Trp Glu Leu Gln Lys Glu Asn Ser Lys Arg Trp Asn Pro Glu
545                 550                 555                 560
Ile Gln Tyr Thr Ser Asn Tyr Asn Lys Ser Val Asn Val Asp Phe Thr
                565                 570                 575
Val Asp Thr Asn Gly Val Tyr Ser Glu Pro Arg Pro Ile Gly Thr Arg
            580                 585                 590
Tyr Leu Thr Arg Asn Leu
        595

<210> SEQ ID NO 45
<211> LENGTH: 599
<212> TYPE: PRT
<213> ORGANISM: Adeno-associated virus

<400> SEQUENCE: 45

Thr Ala Pro Gly Lys Lys Gly Ala Val Asp Gln Ser Pro Gln Glu Pro
1               5                   10                  15
Asp Ser Ser Ser Gly Val Gly Lys Ser Gly Lys Gln Pro Ala Arg Lys
            20                  25                  30
Arg Leu Asn Phe Gly Gln Thr Gly Asp Ser Glu Ser Val Pro Asp Pro
        35                  40                  45
Gln Pro Leu Gly Glu Pro Pro Ala Ala Pro Thr Ser Leu Gly Ser Asn
    50                  55                  60
Thr Met Ala Ser Gly Gly Gly Ala Pro Met Ala Asp Asn Asn Glu Gly
65                  70                  75                  80
Ala Asp Gly Val Gly Asn Ser Ser Gly Asn Trp His Cys Asp Ser Gln
                85                  90                  95
Trp Leu Gly Asp Arg Val Ile Thr Thr Ser Thr Arg Thr Trp Ala Leu
            100                 105                 110
Pro Thr Tyr Asn Asn His Leu Tyr Lys Gln Ile Ser Ser Gln Ser Gly
```

-continued

```
            115                 120                 125
Ala Ser Asn Asp Asn His Tyr Phe Gly Tyr Ser Thr Pro Trp Gly Tyr
130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Lys Leu Ser Phe
                165                 170                 175

Lys Leu Phe Asn Ile Gln Val Arg Gly Val Thr Gln Asn Asp Gly Thr
                180                 185                 190

Thr Thr Ile Ala Asn Asn Leu Thr Ser Thr Val Gln Val Phe Thr Asp
            195                 200                 205

Ser Glu Tyr Gln Leu Pro Tyr Val Leu Gly Ser Ala His Gln Gly Cys
210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
                260                 265                 270

Gln Phe Ser Tyr Thr Phe Glu Asp Val Pro Phe His Ser Ser Tyr Ala
            275                 280                 285

His Ser Gln Ser Leu Asp Arg Leu Met Asn Pro Leu Ile Asp Gln Tyr
290                 295                 300

Leu Tyr Tyr Leu Asn Arg Thr Gln Gly Thr Thr Ser Gly Thr Thr Asn
305                 310                 315                 320

Gln Ser Arg Leu Leu Phe Ser Gln Ala Gly Pro Gln Ser Met Ser Leu
                325                 330                 335

Gln Ala Arg Asn Trp Leu Pro Gly Pro Cys Tyr Arg Gln Gln Arg Leu
                340                 345                 350

Ser Lys Thr Ala Asn Asp Asn Asn Asn Ser Asn Phe Pro Trp Thr Ala
            355                 360                 365

Ala Ser Lys Tyr His Leu Asn Gly Arg Asp Ser Leu Val Asn Pro Gly
370                 375                 380

Pro Ala Met Ala Ser His Lys Asp Asp Glu Glu Lys Phe Phe Pro Met
385                 390                 395                 400

His Gly Asn Leu Ile Phe Gly Lys Glu Gly Thr Thr Ala Ser Asn Ala
                405                 410                 415

Glu Leu Asp Asn Val Met Ile Thr Asp Glu Glu Glu Ile Arg Thr Thr
                420                 425                 430

Asn Pro Val Ala Thr Glu Gln Tyr Gly Thr Val Ala Asn Asn Leu Gln
            435                 440                 445

Ser Ser Asn Thr Ala Pro Thr Thr Gly Thr Val Asn His Gln Gly Ala
450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly His Phe His Pro Ser Pro
                485                 490                 495

Leu Met Gly Gly Phe Gly Leu Lys His Pro Pro Pro Gln Ile Met Ile
                500                 505                 510

Lys Asn Thr Pro Val Pro Ala Asn Pro Pro Thr Thr Phe Ser Pro Ala
            515                 520                 525

Lys Phe Ala Ser Phe Ile Thr Gln Tyr Ser Thr Gly Gln Val Ser Val
530                 535                 540
```

Glu Ile Glu Trp Glu Leu Gln Lys Glu Asn Ser Lys Arg Trp Asn Pro
545                 550                 555                 560

Glu Ile Gln Tyr Thr Ser Asn Tyr Asn Lys Ser Val Asn Val Asp Phe
                565                 570                 575

Thr Val Asp Thr Asn Gly Val Tyr Ser Glu Pro Arg Pro Ile Gly Thr
                580                 585                 590

Arg Tyr Leu Thr Arg Asn Leu
        595

<210> SEQ ID NO 46
<211> LENGTH: 598
<212> TYPE: PRT
<213> ORGANISM: Adeno-associated virus

<400> SEQUENCE: 46

Thr Ala Pro Gly Lys Lys Arg Pro Leu Ile Glu Ser Pro Gln Gln Pro
1               5                   10                  15

Asp Ser Ser Thr Gly Ile Gly Lys Lys Gly Lys Gln Pro Ala Lys Lys
            20                  25                  30

Lys Leu Val Phe Glu Asp Glu Thr Gly Ala Gly Asp Gly Pro Pro Glu
        35                  40                  45

Gly Ser Thr Ser Gly Ala Met Ser Asp Asp Ser Glu Met Arg Ala Ala
    50                  55                  60

Ala Gly Gly Ala Ala Val Glu Gly Gly Gln Gly Ala Asp Gly Val Gly
65                  70                  75                  80

Asn Ala Ser Gly Asp Trp His Cys Asp Ser Thr Trp Ser Glu Gly His
                85                  90                  95

Val Thr Thr Thr Ser Thr Arg Thr Trp Val Leu Pro Thr Tyr Asn Asn
                100                 105                 110

His Leu Tyr Lys Arg Leu Gly Glu Ser Leu Gln Ser Asn Thr Tyr Asn
            115                 120                 125

Gly Phe Ser Thr Pro Trp Gly Tyr Phe Asp Phe Asn Arg Phe His Cys
        130                 135                 140

His Phe Ser Pro Arg Asp Trp Gln Arg Leu Ile Asn Asn Asn Trp Gly
145                 150                 155                 160

Met Arg Pro Lys Ala Met Arg Val Lys Ile Phe Asn Ile Gln Val Lys
                165                 170                 175

Glu Val Thr Thr Ser Asn Gly Glu Thr Thr Val Ala Asn Asn Leu Thr
            180                 185                 190

Ser Thr Val Gln Ile Phe Ala Asp Ser Ser Tyr Glu Leu Pro Tyr Val
        195                 200                 205

Met Asp Ala Gly Gln Glu Gly Ser Leu Pro Pro Phe Pro Asn Asp Val
    210                 215                 220

Phe Met Val Pro Gln Tyr Gly Tyr Cys Gly Leu Val Thr Gly Asn Thr
225                 230                 235                 240

Ser Gln Gln Gln Thr Asp Arg Asn Ala Phe Tyr Cys Leu Glu Tyr Phe
                245                 250                 255

Pro Ser Gln Met Leu Arg Thr Gly Asn Asn Phe Glu Ile Thr Tyr Ser
            260                 265                 270

Phe Glu Lys Val Pro Phe His Ser Met Tyr Ala His Ser Gln Ser Leu
        275                 280                 285

Asp Arg Leu Met Asn Pro Leu Ile Asp Gln Tyr Leu Trp Gly Leu Gln
    290                 295                 300

Ser Thr Thr Thr Gly Thr Thr Leu Asn Ala Gly Thr Ala Thr Thr Asn

```
                305                 310                 315                 320
        Phe Thr Lys Leu Arg Pro Thr Asn Phe Ser Asn Phe Lys Lys Asn Trp
                        325                 330                 335

Leu Pro Gly Pro Ser Ile Lys Gln Gln Gly Phe Ser Lys Thr Ala Asn
                        340                 345                 350

Gln Asn Tyr Lys Ile Pro Ala Thr Gly Ser Asp Ser Leu Ile Lys Tyr
                        355                 360                 365

Glu Thr His Ser Thr Leu Asp Gly Arg Trp Ser Ala Leu Thr Pro Gly
                370                 375                 380

Pro Pro Met Ala Thr Ala Gly Pro Ala Asp Ser Lys Phe Ser Asn Ser
        385                 390                 395                 400

Gln Leu Ile Phe Ala Gly Pro Lys Gln Asn Gly Asn Thr Ala Thr Val
                        405                 410                 415

Pro Gly Thr Leu Ile Phe Thr Ser Glu Glu Leu Ala Ala Thr Asn
                        420                 425                 430

Ala Thr Asp Thr Asp Met Trp Gly Asn Leu Pro Gly Gly Asp Gln Ser
                        435                 440                 445

Asn Ser Asn Leu Pro Thr Val Asp Arg Leu Thr Ala Leu Gly Ala Val
                450                 455                 460

Pro Gly Met Val Trp Gln Asn Arg Asp Ile Tyr Tyr Gln Gly Pro Ile
        465                 470                 475                 480

Trp Ala Lys Ile Pro His Thr Asp Gly His Phe His Pro Ser Pro Leu
                        485                 490                 495

Ile Gly Gly Phe Gly Leu Lys His Pro Pro Pro Gln Ile Phe Ile Lys
                        500                 505                 510

Asn Thr Pro Val Pro Ala Asn Pro Ala Thr Thr Phe Ser Ser Thr Pro
                        515                 520                 525

Val Asn Ser Phe Ile Thr Gln Tyr Ser Thr Gly Gln Val Ser Val Gln
                530                 535                 540

Ile Asp Trp Glu Ile Gln Lys Glu Arg Ser Lys Arg Trp Asn Pro Glu
        545                 550                 555                 560

Val Gln Phe Thr Ser Asn Tyr Gly Gln Gln Asn Ser Leu Leu Trp Ala
                        565                 570                 575

Pro Asp Ala Ala Gly Lys Tyr Thr Glu Pro Arg Ala Ile Gly Thr Arg
                        580                 585                 590

Tyr Leu Thr His His Leu
                595

<210> SEQ ID NO 47
<211> LENGTH: 588
<212> TYPE: PRT
<213> ORGANISM: Adeno-associated virus

<400> SEQUENCE: 47

Thr Ala Pro Thr Gly Lys Arg Ile Asp Asp His Phe Pro Lys Arg Lys
        1               5                   10                  15

Lys Ala Arg Thr Glu Glu Asp Ser Lys Pro Ser Thr Ser Ser Asp Ala
                        20                  25                  30

Glu Ala Gly Pro Ser Gly Ser Gln Gln Leu Gln Ile Pro Ala Gln Pro
                        35                  40                  45

Ala Ser Ser Leu Gly Ala Asp Thr Met Ser Ala Gly Gly Gly Gly Pro
                50                  55                  60

Leu Gly Asp Asn Asn Gln Gly Ala Asp Gly Val Gly Asn Ala Ser Gly
        65                  70                  75                  80
```

```
Asp Trp His Cys Asp Ser Thr Trp Met Gly Asp Arg Val Val Thr Lys
                 85                  90                  95

Ser Thr Arg Thr Trp Val Leu Pro Ser Tyr Asn Asn His Gln Tyr Arg
            100                 105                 110

Glu Ile Lys Ser Gly Ser Val Asp Gly Ser Asn Ala Asn Ala Tyr Phe
        115                 120                 125

Gly Tyr Ser Thr Pro Trp Gly Tyr Phe Asp Phe Asn Arg Phe His Ser
    130                 135                 140

His Trp Ser Pro Arg Asp Trp Gln Arg Leu Ile Asn Asn Tyr Trp Gly
145                 150                 155                 160

Phe Arg Pro Arg Ser Leu Arg Val Lys Ile Phe Asn Ile Gln Val Lys
                165                 170                 175

Glu Val Thr Val Gln Asp Ser Thr Thr Ile Ala Asn Asn Leu Thr
            180                 185                 190

Ser Thr Val Gln Val Phe Thr Asp Asp Tyr Gln Leu Pro Tyr Val
        195                 200                 205

Val Gly Asn Gly Thr Glu Gly Cys Leu Pro Ala Phe Pro Pro Gln Val
    210                 215                 220

Phe Thr Leu Pro Gln Tyr Gly Tyr Ala Thr Leu Asn Arg Asp Asn Thr
225                 230                 235                 240

Glu Asn Pro Thr Glu Arg Ser Ser Phe Phe Cys Leu Glu Tyr Phe Pro
                245                 250                 255

Ser Lys Met Leu Arg Thr Gly Asn Asn Phe Glu Phe Thr Tyr Asn Phe
                260                 265                 270

Glu Glu Val Pro Phe His Ser Ser Phe Ala Pro Ser Gln Asn Leu Phe
            275                 280                 285

Lys Leu Ala Asn Pro Leu Val Asp Gln Tyr Leu Tyr Arg Phe Val Ser
        290                 295                 300

Thr Asn Asn Thr Gly Gly Val Gln Phe Asn Lys Asn Leu Ala Gly Arg
305                 310                 315                 320

Tyr Ala Asn Thr Tyr Lys Asn Trp Phe Pro Gly Pro Met Gly Arg Thr
                325                 330                 335

Gln Gly Trp Asn Leu Gly Ser Gly Val Asn Arg Ala Ser Val Ser Ala
            340                 345                 350

Phe Ala Thr Thr Asn Arg Met Glu Leu Glu Gly Ala Ser Tyr Gln Val
        355                 360                 365

Pro Pro Gln Pro Asn Gly Met Thr Asn Asn Leu Gln Gly Ser Asn Thr
    370                 375                 380

Tyr Ala Leu Glu Asn Thr Met Ile Phe Asn Ser Gln Pro Ala Asn Pro
385                 390                 395                 400

Gly Thr Thr Ala Thr Tyr Leu Glu Gly Asn Met Leu Ile Thr Ser Glu
                405                 410                 415

Ser Glu Thr Gln Pro Val Asn Arg Val Ala Tyr Asn Val Gly Gly Gln
            420                 425                 430

Met Ala Thr Asn Asn Gln Ser Ser Thr Thr Ala Pro Ala Thr Gly Thr
        435                 440                 445

Tyr Asn Leu Gln Glu Ile Val Pro Gly Ser Val Trp Met Glu Arg Asp
    450                 455                 460

Val Tyr Leu Gln Gly Pro Ile Trp Ala Lys Ile Pro Glu Thr Gly Ala
465                 470                 475                 480

His Phe His Pro Ser Pro Ala Met Gly Gly Phe Gly Leu Lys His Pro
                485                 490                 495

Pro Pro Met Met Leu Ile Lys Asn Thr Pro Val Pro Gly Asn Ile Thr
```

```
                500                 505                 510
Ser Phe Ser Asp Val Pro Val Ser Ser Phe Ile Thr Gln Tyr Ser Thr
            515                 520                 525

Gly Gln Val Thr Val Glu Met Glu Trp Glu Leu Lys Lys Glu Asn Ser
        530                 535                 540

Lys Arg Trp Asn Pro Glu Ile Gln Tyr Thr Asn Asn Tyr Asn Asp Pro
545                 550                 555                 560

Gln Phe Val Asp Phe Ala Pro Asp Ser Thr Gly Glu Tyr Arg Thr Thr
                565                 570                 575

Arg Pro Ile Gly Thr Arg Tyr Leu Thr Arg Pro Leu
                580                 585

<210> SEQ ID NO 48
<211> LENGTH: 599
<212> TYPE: PRT
<213> ORGANISM: Adeno-associated virus

<400> SEQUENCE: 48

Thr Ala Pro Gly Lys Lys Arg Pro Val Glu Gln Ser Pro Gln Glu Pro
1               5                   10                  15

Asp Ser Ser Gly Ile Gly Lys Thr Gly Gln Pro Ala Lys Lys
            20                  25                  30

Arg Leu Asn Phe Gly Gln Thr Gly Asp Ser Glu Ser Val Pro Asp Pro
            35                  40                  45

Gln Pro Leu Gly Glu Pro Pro Ala Thr Pro Ala Ala Val Gly Pro Thr
        50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Thr Asn Asp Gly
            180                 185                 190

Val Thr Thr Ile Ala Asn Asn Leu Thr Ser Thr Val Gln Val Phe Ser
        195                 200                 205

Asp Ser Glu Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asn Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Asp Val Pro Phe His Ser Ser Tyr
        275                 280                 285
```

Ala His Ser Gln Ser Leu Asp Arg Leu Met Asn Pro Leu Ile Asp Gln
            290                 295                 300

Tyr Leu Tyr Tyr Leu Asn Arg Thr Gln Asn Gln Ser Gly Ser Ala Gln
305                 310                 315                 320

Asn Lys Asp Leu Leu Phe Ser Arg Gly Ser Pro Ala Gly Met Ser Val
                325                 330                 335

Gln Pro Lys Asn Trp Leu Pro Gly Pro Cys Tyr Arg Gln Gln Arg Val
            340                 345                 350

Ser Lys Thr Lys Thr Asp Asn Asn Ser Asn Phe Thr Trp Thr Gly
            355                 360                 365

Ala Ser Lys Tyr Asn Leu Asn Gly Arg Glu Ser Ile Ile Asn Pro Gly
370                 375                 380

Thr Ala Met Ala Ser His Lys Asp Asp Lys Asp Lys Phe Phe Pro Met
385                 390                 395                 400

Ser Gly Val Met Ile Phe Gly Lys Glu Ser Ala Gly Ala Ser Asn Thr
                405                 410                 415

Ala Leu Asp Asn Val Met Ile Thr Asp Glu Glu Ile Lys Ala Thr
                420                 425                 430

Asn Pro Val Ala Thr Glu Arg Phe Gly Thr Val Ala Val Asn Leu Gln
            435                 440                 445

Ser Ser Ser Thr Asp Pro Ala Thr Gly Asp Val His Val Met Gly Ala
450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly His Phe His Pro Ser Pro
                485                 490                 495

Leu Met Gly Gly Phe Gly Leu Lys His Pro Pro Gln Ile Leu Ile
            500                 505                 510

Lys Asn Thr Pro Val Pro Ala Asn Pro Pro Ala Glu Phe Ser Ala Thr
            515                 520                 525

Lys Phe Ala Ser Phe Ile Thr Gln Tyr Ser Thr Gly Gln Val Ser Val
            530                 535                 540

Glu Ile Glu Trp Glu Leu Gln Lys Glu Asn Ser Lys Arg Trp Asn Pro
545                 550                 555                 560

Glu Val Gln Tyr Thr Ser Asn Tyr Ala Lys Ser Ala Asn Val Asp Phe
                565                 570                 575

Thr Val Asp Asn Asn Gly Leu Tyr Thr Glu Pro Arg Pro Ile Gly Thr
            580                 585                 590

Arg Tyr Leu Thr Arg Pro Leu
            595

<210> SEQ ID NO 49
<211> LENGTH: 600
<212> TYPE: PRT
<213> ORGANISM: Adeno-associated virus

<400> SEQUENCE: 49

Thr Ala Pro Ala Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Arg
                20                  25                  30

Lys Arg Leu Asn Phe Gly Gln Thr Gly Asp Ser Glu Ser Val Pro Asp
            35                  40                  45

Pro Gln Pro Leu Gly Glu Pro Pro Ala Ala Pro Ser Ser Val Gly Ser
    50                  55                  60

```
Gly Thr Val Ala Ala Gly Gly Ala Pro Met Ala Asp Asn Asn Glu
 65                  70                  75                  80

Gly Ala Asp Gly Val Gly Asn Ala Ser Gly Asn Trp His Cys Asp Ser
                 85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Ser Glu Thr
        115                 120                 125

Ala Gly Ser Thr Asn Asp Asn Thr Tyr Phe Gly Tyr Ser Thr Pro Trp
130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Lys Leu
                165                 170                 175

Arg Phe Lys Leu Phe Asn Ile Gln Val Lys Glu Val Thr Thr Asn Asp
            180                 185                 190

Gly Val Thr Thr Ile Ala Asn Asn Leu Thr Ser Thr Ile Gln Val Phe
        195                 200                 205

Ser Asp Ser Glu Tyr Gln Leu Pro Tyr Val Leu Gly Ser Ala His Gln
210                 215                 220

Gly Cys Leu Pro Pro Phe Pro Ala Asp Val Phe Met Ile Pro Gln Tyr
225                 230                 235                 240

Gly Tyr Leu Thr Leu Asn Asn Gly Ser Gln Ser Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Glu Phe Ser Tyr Ser Phe Glu Asp Val Pro Phe His Ser Ser
        275                 280                 285

Tyr Ala His Ser Gln Ser Leu Asp Arg Leu Met Asn Pro Leu Ile Asp
290                 295                 300

Gln Tyr Leu Tyr Tyr Leu Ala Arg Thr Gln Ser Asn Pro Gly Gly Thr
305                 310                 315                 320

Ala Gly Asn Arg Glu Leu Gln Phe Tyr Gln Gly Gly Pro Ser Thr Met
                325                 330                 335

Ala Glu Gln Ala Lys Asn Trp Leu Pro Gly Pro Cys Phe Arg Gln Gln
            340                 345                 350

Arg Val Ser Lys Thr Leu Asp Gln Asn Asn Asn Ser Asn Phe Ala Trp
        355                 360                 365

Thr Gly Ala Thr Lys Tyr His Leu Asn Gly Arg Asn Ser Leu Val Asn
370                 375                 380

Pro Gly Val Ala Met Ala Thr His Lys Asp Asp Glu Asp Arg Phe Phe
385                 390                 395                 400

Pro Ser Ser Gly Val Leu Ile Phe Gly Lys Thr Gly Ala Thr Asn Lys
                405                 410                 415

Thr Thr Leu Glu Asn Val Leu Met Thr Asn Glu Glu Ile Arg Pro
            420                 425                 430

Thr Asn Pro Val Ala Thr Glu Glu Tyr Gly Ile Val Ser Ser Asn Leu
        435                 440                 445

Gln Ala Ala Asn Thr Ala Ala Gln Thr Gln Val Val Asn Asn Gln Gly
450                 455                 460

Ala Leu Pro Gly Met Val Trp Gln Asn Arg Asp Val Tyr Leu Gln Gly
465                 470                 475                 480
```

-continued

```
Pro Ile Trp Ala Lys Ile Pro His Thr Asp Gly Asn Phe His Pro Ser
                485                 490                 495
Pro Leu Met Gly Gly Phe Gly Leu Lys His Pro Pro Gln Ile Leu
            500                 505                 510
Ile Lys Asn Thr Pro Val Pro Ala Asn Pro Pro Glu Val Phe Thr Pro
                515                 520                 525
Ala Lys Phe Ala Ser Phe Ile Thr Gln Tyr Ser Thr Gly Gln Val Ser
            530                 535                 540
Val Glu Ile Glu Trp Glu Leu Gln Lys Glu Asn Ser Lys Arg Trp Asn
545                 550                 555                 560
Pro Glu Ile Gln Tyr Thr Ser Asn Phe Glu Lys Gln Thr Gly Val Asp
                565                 570                 575
Phe Ala Val Asp Ser Gln Gly Val Tyr Ser Glu Pro Arg Pro Ile Gly
            580                 585                 590
Thr Arg Tyr Leu Thr Arg Asn Leu
                595                 600

<210> SEQ ID NO 50
<211> LENGTH: 601
<212> TYPE: PRT
<213> ORGANISM: Adeno-associated virus

<400> SEQUENCE: 50

Thr Ala Pro Gly Lys Lys Arg Pro Val Glu Pro Ser Pro Gln Arg Ser
1               5                   10                  15
Pro Asp Ser Ser Thr Gly Ile Gly Lys Lys Gly Gln Gln Pro Ala Arg
            20                  25                  30
Lys Arg Leu Asn Phe Gly Gln Thr Gly Asp Ser Glu Ser Val Pro Asp
        35                  40                  45
Pro Gln Pro Leu Gly Glu Pro Pro Ala Ala Pro Ser Gly Val Gly Pro
    50                  55                  60
Asn Thr Met Ala Ala Gly Gly Gly Ala Pro Met Ala Asp Asn Asn Glu
65                  70                  75                  80
Gly Ala Asp Gly Val Gly Ser Ser Ser Gly Asn Trp His Cys Asp Ser
                85                  90                  95
Thr Trp Leu Gly Asp Arg Val Ile Thr Thr Ser Thr Arg Thr Trp Ala
            100                 105                 110
Leu Pro Thr Tyr Asn Asn His His Leu Tyr Lys Gln Ile Ser Asn Gly Thr
        115                 120                 125
Ser Gly Gly Ala Thr Asn Asp Asn Thr Tyr Phe Gly Tyr Ser Thr Pro
    130                 135                 140
Trp Gly Tyr Phe Asp Phe Asn Arg Phe His Cys His Phe Ser Pro Arg
145                 150                 155                 160
Asp Trp Gln Arg Leu Ile Asn Asn Asn Trp Gly Phe Arg Pro Lys Arg
                165                 170                 175
Leu Ser Phe Lys Leu Phe Asn Ile Gln Val Lys Glu Val Thr Gln Asn
            180                 185                 190
Glu Gly Thr Lys Thr Ile Ala Asn Asn Leu Thr Ser Thr Ile Gln Val
        195                 200                 205
Phe Thr Asp Ser Glu Tyr Gln Leu Pro Tyr Val Leu Gly Ser Ala His
    210                 215                 220
Gln Gly Cys Leu Pro Pro Phe Pro Ala Asp Val Phe Met Ile Pro Gln
225                 230                 235                 240
Tyr Gly Tyr Leu Thr Leu Asn Asn Gly Ser Gln Ala Val Gly Arg Ser
                245                 250                 255
```

Ser Phe Tyr Cys Leu Glu Tyr Phe Pro Ser Gln Met Leu Arg Thr Gly
          260                 265                 270

Asn Asn Phe Gln Phe Thr Tyr Thr Phe Glu Asp Val Pro Phe His Ser
          275                 280                 285

Ser Tyr Ala His Ser Gln Ser Leu Asp Arg Leu Met Asn Pro Leu Ile
          290                 295                 300

Asp Gln Tyr Leu Tyr Tyr Leu Ser Arg Thr Gln Thr Thr Gly Gly Thr
305                 310                 315                 320

Ala Asn Thr Gln Thr Leu Gly Phe Ser Gln Gly Gly Pro Asn Thr Met
                  325                 330                 335

Ala Asn Gln Ala Lys Asn Trp Leu Pro Gly Pro Cys Tyr Arg Gln Gln
              340                 345                 350

Arg Val Ser Thr Thr Thr Gly Gln Asn Asn Asn Ser Asn Phe Ala Trp
          355                 360                 365

Thr Ala Gly Thr Lys Tyr His Leu Asn Gly Arg Asn Ser Leu Ala Asn
          370                 375                 380

Pro Gly Ile Ala Met Ala Thr His Lys Asp Asp Glu Glu Arg Phe Phe
385                 390                 395                 400

Pro Ser Asn Gly Ile Leu Ile Phe Gly Lys Gln Asn Ala Ala Arg Asp
                  405                 410                 415

Asn Ala Asp Tyr Ser Asp Val Met Leu Thr Ser Glu Glu Ile Lys
              420                 425                 430

Thr Thr Asn Pro Val Ala Thr Glu Glu Tyr Gly Ile Val Ala Asp Asn
          435                 440                 445

Leu Gln Gln Gln Asn Thr Ala Pro Gln Ile Gly Thr Val Asn Ser Gln
          450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                  485                 490                 495

Ser Pro Leu Met Gly Gly Phe Gly Leu Lys His Pro Pro Pro Gln Ile
              500                 505                 510

Leu Ile Lys Asn Thr Pro Val Pro Ala Asp Pro Pro Thr Thr Phe Asn
          515                 520                 525

Gln Ser Lys Leu Asn Ser Phe Ile Thr Gln Tyr Ser Thr Gly Gln Val
          530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Ser Val
                  565                 570                 575

Asp Phe Ala Val Asn Thr Glu Gly Val Tyr Ser Glu Pro Arg Pro Ile
              580                 585                 590

Gly Thr Arg Tyr Leu Thr Arg Asn Leu
          595                 600

<210> SEQ ID NO 51
<211> LENGTH: 599
<212> TYPE: PRT
<213> ORGANISM: Adeno-associated virus

<400> SEQUENCE: 51

Thr Ala Pro Gly Lys Lys Arg Pro Val Glu Gln Ser Pro Gln Glu Pro
1               5                   10                  15

Asp Ser Ser Ala Gly Ile Gly Lys Ser Gly Ala Gln Pro Ala Lys Lys

```
            20                  25                  30
Arg Leu Asn Phe Gly Gln Thr Gly Asp Thr Glu Ser Val Pro Asp Pro
             35                  40                  45
Gln Pro Ile Gly Glu Pro Pro Ala Ala Pro Ser Gly Val Gly Ser Leu
 50                  55                  60
Thr Met Ala Ser Gly Gly Ala Pro Val Ala Asp Asn Asn Glu Gly
 65                  70                  75                  80
Ala Asp Gly Val Gly Ser Ser Gly Asn Trp His Cys Asp Ser Gln
                 85                  90                  95
Trp Leu Gly Asp Arg Val Ile Thr Thr Ser Thr Arg Thr Trp Ala Leu
                100                 105                 110
Pro Thr Tyr Asn Asn His Leu Tyr Lys Gln Ile Ser Asn Ser Thr Ser
            115                 120                 125
Gly Gly Ser Ser Asn Asp Asn Ala Tyr Phe Gly Tyr Ser Thr Pro Trp
            130                 135                 140
Gly Tyr Phe Asp Phe Asn Arg Phe His Cys His Phe Ser Pro Arg Asp
145                 150                 155                 160
Trp Gln Arg Leu Ile Asn Asn Asn Trp Gly Phe Arg Pro Lys Arg Leu
                165                 170                 175
Asn Phe Lys Leu Phe Asn Ile Gln Val Lys Glu Val Thr Asp Asn Asn
                180                 185                 190
Gly Val Lys Thr Ile Ala Asn Asn Leu Thr Ser Thr Val Gln Val Phe
            195                 200                 205
Thr Asp Ser Asp Tyr Gln Leu Pro Tyr Val Leu Gly Ser Ala His Glu
210                 215                 220
Gly Cys Leu Pro Pro Phe Pro Ala Asp Val Phe Met Ile Pro Gln Tyr
225                 230                 235                 240
Gly Tyr Leu Thr Leu Asn Asp Gly Ser Gln Ala Val Gly Arg Ser Ser
                245                 250                 255
Phe Tyr Cys Leu Glu Tyr Phe Pro Ser Gln Met Leu Arg Thr Gly Asn
                260                 265                 270
Asn Phe Gln Phe Ser Tyr Glu Phe Glu Asn Val Pro Phe His Ser Ser
            275                 280                 285
Tyr Ala His Ser Gln Ser Leu Asp Arg Leu Met Asn Pro Leu Ile Asp
            290                 295                 300
Gln Tyr Leu Tyr Tyr Leu Ser Lys Thr Ile Asn Gly Ser Gly Gln Asn
305                 310                 315                 320
Gln Gln Thr Leu Lys Phe Ser Val Ala Gly Pro Ser Asn Met Ala Val
                325                 330                 335
Gln Gly Arg Asn Tyr Ile Pro Gly Pro Ser Tyr Arg Gln Gln Arg Val
                340                 345                 350
Ser Thr Thr Val Thr Gln Asn Asn Asn Ser Glu Phe Ala Trp Pro Gly
            355                 360                 365
Ala Ser Ser Trp Ala Leu Asn Gly Arg Asn Ser Leu Met Asn Pro Gly
            370                 375                 380
Pro Ala Met Ala Ser His Lys Glu Gly Glu Asp Arg Phe Phe Pro Leu
385                 390                 395                 400
Ser Gly Ser Leu Ile Phe Gly Lys Gln Gly Thr Gly Arg Asp Asn Val
                405                 410                 415
Asp Ala Asp Lys Val Met Ile Thr Asn Glu Glu Glu Ile Lys Thr Thr
                420                 425                 430
Asn Pro Val Ala Thr Glu Ser Tyr Gly Gln Val Ala Thr Asn His Gln
            435                 440                 445
```

Ser Ala Gln Ala Gln Ala Gln Thr Gly Trp Val Gln Asn Gln Gly Ile
            450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly Asn Phe His Pro Ser Pro
            485                 490                 495

Leu Met Gly Gly Phe Gly Met Lys His Pro Pro Gln Ile Leu Ile
            500                 505                 510

Lys Asn Thr Pro Val Pro Ala Asp Pro Pro Thr Ala Phe Asn Lys Asp
            515                 520                 525

Lys Leu Asn Ser Phe Ile Thr Gln Tyr Ser Thr Gly Val Ser Val
            530                 535                 540

Glu Ile Glu Trp Glu Leu Gln Lys Glu Asn Ser Lys Arg Trp Asn Pro
545                 550                 555                 560

Glu Ile Gln Tyr Thr Ser Asn Tyr Tyr Lys Ser Asn Asn Val Glu Phe
                565                 570                 575

Ala Val Asn Thr Glu Gly Val Tyr Ser Glu Pro Arg Pro Ile Gly Thr
            580                 585                 590

Arg Tyr Leu Thr Arg Asn Leu
            595

<210> SEQ ID NO 52
<211> LENGTH: 601
<212> TYPE: PRT
<213> ORGANISM: Adeno-associated virus

<400> SEQUENCE: 52

Thr Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Lys
                20                  25                  30

Lys Arg Leu Asn Phe Gly Gln Thr Gly Glu Ser Glu Ser Val Pro Asp
            35                  40                  45

Pro Gln Pro Ile Gly Glu Pro Pro Ala Gly Pro Ser Gly Leu Gly Ser
    50                  55                  60

Gly Thr Met Ala Ala Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Ser Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His

```
                210                 215                 220
Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
                260                 265                 270

Asn Asn Phe Glu Phe Ser Tyr Thr Phe Glu Asp Val Pro Phe His Ser
                275                 280                 285

Ser Tyr Ala His Ser Gln Ser Leu Asp Arg Leu Met Asn Pro Leu Ile
                290                 295                 300

Asp Gln Tyr Leu Tyr Tyr Leu Ser Arg Thr Gln Ser Thr Gly Gly Thr
305                 310                 315                 320

Gln Gly Thr Gln Gln Leu Leu Phe Ser Gln Ala Gly Pro Ala Asn Met
                325                 330                 335

Ser Ala Gln Ala Lys Asn Trp Leu Pro Gly Pro Cys Tyr Arg Gln Gln
                340                 345                 350

Arg Val Ser Thr Thr Leu Ser Gln Asn Asn Asn Ser Asn Phe Ala Trp
                355                 360                 365

Thr Gly Ala Thr Lys Tyr His Leu Asn Gly Arg Asp Ser Leu Val Asn
                370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Arg Asp
                405                 410                 415

Asn Val Asp Tyr Ser Ser Val Met Leu Thr Ser Glu Glu Glu Ile Lys
                420                 425                 430

Thr Thr Asn Pro Val Ala Thr Glu Gln Tyr Gly Val Val Ala Asp Asn
                435                 440                 445

Leu Gln Gln Ala Asn Thr Gly Pro Ile Val Gly Asn Val Asn Ser Gln
450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Pro Gln Ile
                500                 505                 510

Leu Ile Lys Asn Thr Pro Val Pro Ala Asp Pro Pro Thr Thr Phe Ser
                515                 520                 525

Gln Ala Lys Leu Ala Ser Phe Ile Thr Gln Tyr Ser Thr Gly Gln Val
                530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Asn Val
                565                 570                 575

Asp Phe Ala Val Asn Thr Glu Gly Thr Tyr Ser Glu Pro Arg Pro Ile
                580                 585                 590

Gly Thr Arg Tyr Leu Thr Arg Asn Leu
                595                 600

<210> SEQ ID NO 53
<211> LENGTH: 596
<212> TYPE: PRT
<213> ORGANISM: Adeno-associated virus
```

<400> SEQUENCE: 53

```
Thr Ala Pro Gly Lys Lys Arg Pro Leu Glu Ser Pro Gln Glu Pro Asp
1               5                   10                  15

Ser Ser Ser Gly Ile Gly Lys Lys Gly Lys Gln Pro Ala Arg Lys Arg
            20                  25                  30

Leu Asn Phe Glu Glu Asp Thr Gly Ala Gly Asp Gly Pro Pro Glu Gly
            35                  40                  45

Ser Asp Thr Ser Ala Met Ser Ser Asp Ile Glu Met Arg Ala Ala Pro
50                  55                  60

Gly Gly Asn Ala Val Asp Ala Gly Gln Gly Ser Asp Gly Val Gly Asn
65                  70                  75                  80

Ala Ser Gly Asp Trp His Cys Asp Ser Thr Trp Ser Glu Gly Lys Val
                85                  90                  95

Thr Thr Thr Ser Thr Arg Thr Trp Val Leu Pro Thr Tyr Asn Asn His
            100                 105                 110

Leu Tyr Leu Arg Leu Gly Thr Thr Ser Ser Asn Thr Tyr Asn Gly
            115                 120                 125

Phe Ser Thr Pro Trp Gly Tyr Phe Asp Phe Asn Arg Phe His Cys His
            130                 135                 140

Phe Ser Pro Arg Asp Trp Gln Arg Leu Ile Asn Asn Asn Trp Gly Leu
145                 150                 155                 160

Arg Pro Lys Ala Met Arg Val Lys Ile Phe Asn Ile Gln Val Lys Glu
                165                 170                 175

Val Thr Thr Ser Asn Gly Glu Thr Thr Val Ala Asn Asn Leu Thr Ser
            180                 185                 190

Thr Val Gln Ile Phe Ala Asp Ser Ser Tyr Glu Leu Pro Tyr Val Met
            195                 200                 205

Asp Ala Gly Gln Glu Gly Ser Leu Pro Pro Phe Pro Asn Asp Val Phe
210                 215                 220

Met Val Pro Gln Tyr Gly Tyr Cys Gly Ile Val Thr Gly Glu Asn Gln
225                 230                 235                 240

Asn Gln Thr Asp Arg Asn Ala Phe Tyr Cys Leu Glu Tyr Phe Pro Ser
                245                 250                 255

Gln Met Leu Arg Thr Gly Asn Asn Phe Glu Met Ala Tyr Asn Phe Glu
            260                 265                 270

Lys Val Pro Phe His Ser Met Tyr Ala His Ser Gln Ser Leu Asp Arg
            275                 280                 285

Leu Met Asn Pro Leu Leu Asp Gln Tyr Leu Trp His Leu Gln Ser Thr
            290                 295                 300

Thr Ser Gly Glu Thr Leu Asn Gln Gly Asn Ala Ala Thr Thr Phe Gly
305                 310                 315                 320

Lys Ile Arg Ser Gly Asp Phe Ala Phe Tyr Arg Lys Asn Trp Leu Pro
                325                 330                 335

Gly Pro Cys Val Lys Gln Gln Arg Phe Ser Lys Thr Ala Ser Gln Asn
            340                 345                 350

Tyr Lys Ile Pro Ala Ser Gly Gly Asn Ala Leu Leu Lys Tyr Asp Thr
            355                 360                 365

His Tyr Thr Leu Asn Asn Arg Trp Ser Asn Ile Ala Pro Gly Pro Pro
            370                 375                 380

Met Ala Thr Ala Gly Pro Ser Asp Gly Asp Phe Ser Asn Ala Gln Leu
385                 390                 395                 400

Ile Phe Pro Gly Pro Ser Val Thr Gly Asn Thr Thr Thr Ser Ala Asn
```

```
            405                 410                 415
Asn Leu Leu Phe Thr Ser Glu Glu Ile Ala Ala Thr Asn Pro Arg
        420                 425                 430

Asp Thr Asp Met Phe Gly Gln Ile Ala Asp Asn Gln Asn Ala Thr
        435                 440                 445

Thr Ala Pro Ile Thr Gly Asn Val Thr Ala Met Gly Val Leu Pro Gly
        450                 455                 460

Met Val Trp Gln Asn Arg Asp Ile Tyr Tyr Gln Gly Pro Ile Trp Ala
465                 470                 475                 480

Lys Ile Pro His Ala Asp Gly His Phe His Pro Ser Pro Leu Ile Gly
                485                 490                 495

Gly Phe Gly Leu Lys His Pro Pro Gln Ile Phe Ile Lys Asn Thr
            500                 505                 510

Pro Val Pro Ala Asn Pro Ala Thr Thr Phe Thr Ala Ala Arg Val Asp
            515                 520                 525

Ser Phe Ile Thr Gln Tyr Ser Thr Gly Gln Val Ala Val Gln Ile Glu
        530                 535                 540

Trp Glu Ile Glu Lys Glu Arg Ser Lys Arg Trp Asn Pro Glu Val Gln
545                 550                 555                 560

Phe Thr Ser Asn Tyr Gly Asn Gln Ser Ser Met Leu Trp Ala Pro Asp
                565                 570                 575

Thr Thr Gly Lys Tyr Thr Glu Pro Arg Val Ile Gly Ser Arg Tyr Leu
            580                 585                 590

Thr Asn His Leu
        595

<210> SEQ ID NO 54
<211> LENGTH: 605
<212> TYPE: PRT
<213> ORGANISM: Adeno-associated virus

<400> SEQUENCE: 54

Thr Ala Pro Gly Lys Lys Arg Pro Leu Glu Lys Thr Pro Asn Arg Pro
1               5                   10                  15

Thr Asn Pro Asp Ser Gly Lys Ala Pro Ala Lys Lys Gln Lys Asp
            20                  25                  30

Gly Glu Pro Ala Asp Ser Ala Arg Arg Thr Leu Asp Phe Glu Asp Ser
        35                  40                  45

Gly Ala Gly Asp Gly Pro Pro Glu Gly Ser Ser Ser Gly Glu Met Ser
    50                  55                  60

His Asp Ala Glu Met Arg Ala Ala Pro Gly Gly Asn Ala Val Glu Ala
65                  70                  75                  80

Gly Gln Gly Ala Asp Gly Val Gly Asn Ala Ser Gly Asp Trp His Cys
                85                  90                  95

Asp Ser Thr Trp Ser Glu Gly Arg Val Thr Thr Thr Ser Thr Arg Thr
            100                 105                 110

Trp Val Leu Pro Thr Tyr Asn Asn His Leu Tyr Leu Arg Ile Gly Thr
        115                 120                 125

Thr Ala Asn Ser Asn Thr Tyr Asn Gly Phe Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Leu Arg Pro Lys Ser Met Arg Val
                165                 170                 175
```

```
Lys Ile Phe Asn Ile Gln Val Lys Glu Val Thr Ser Asn Gly Glu
            180                 185                 190

Thr Thr Val Ala Asn Asn Leu Thr Ser Thr Val Gln Ile Phe Ala Asp
        195                 200                 205

Ser Thr Tyr Glu Leu Pro Tyr Val Met Asp Ala Gly Gln Glu Gly Ser
        210                 215                 220

Phe Pro Pro Phe Pro Asn Asp Val Phe Met Val Pro Gln Tyr Gly Tyr
225                 230                 235                 240

Cys Gly Val Val Thr Gly Lys Asn Gln Asn Gln Thr Asp Arg Asn Ala
                245                 250                 255

Phe Tyr Cys Leu Glu Tyr Phe Pro Ser Gln Met Leu Arg Thr Gly Asn
            260                 265                 270

Asn Phe Glu Val Ser Tyr Gln Phe Glu Lys Val Pro Phe His Ser Met
        275                 280                 285

Tyr Ala His Ser Gln Ser Leu Asp Arg Met Met Asn Pro Leu Leu Asp
        290                 295                 300

Gln Tyr Leu Trp His Leu Gln Ser Thr Thr Gly Asn Ser Leu Asn
305                 310                 315                 320

Gln Gly Thr Ala Thr Thr Tyr Gly Lys Ile Thr Thr Gly Asp Phe
            325                 330                 335

Ala Tyr Tyr Arg Lys Asn Trp Leu Pro Gly Ala Cys Ile Lys Gln Gln
            340                 345                 350

Lys Phe Ser Lys Asn Ala Asn Gln Asn Tyr Lys Ile Pro Ala Ser Gly
            355                 360                 365

Gly Asp Ala Leu Leu Lys Tyr Asp Thr His Thr Thr Leu Asn Gly Arg
370                 375                 380

Trp Ser Asn Met Ala Pro Gly Pro Pro Met Ala Thr Ala Gly Ala Gly
385                 390                 395                 400

Asp Ser Asp Phe Ser Asn Ser Gln Leu Ile Phe Ala Gly Pro Asn Pro
                405                 410                 415

Ser Gly Asn Thr Thr Thr Ser Ser Asn Asn Leu Leu Phe Thr Ser Glu
            420                 425                 430

Glu Glu Ile Ala Thr Thr Asn Pro Arg Asp Thr Asp Met Phe Gly Gln
            435                 440                 445

Ile Ala Asp Asn Asn Gln Asn Ala Thr Thr Ala Pro His Ile Ala Asn
450                 455                 460

Leu Asp Ala Met Gly Ile Val Pro Gly Met Val Trp Gln Asn Arg Asp
465                 470                 475                 480

Ile Tyr Tyr Gln Gly Pro Ile Trp Ala Lys Val Pro His Thr Asp Gly
                485                 490                 495

His Phe His Pro Ser Pro Leu Met Gly Gly Phe Gly Leu Lys His Pro
            500                 505                 510

Pro Pro Gln Ile Phe Ile Lys Asn Thr Pro Val Pro Ala Asn Pro Asn
        515                 520                 525

Thr Thr Phe Ser Ala Ala Arg Ile Asn Ser Phe Leu Thr Gln Tyr Ser
        530                 535                 540

Thr Gly Gln Val Ala Val Gln Ile Asp Trp Glu Ile Gln Lys Glu His
545                 550                 555                 560

Ser Lys Arg Trp Asn Pro Glu Val Gln Phe Thr Ser Asn Tyr Gly Thr
                565                 570                 575

Gln Asn Ser Met Leu Trp Ala Pro Asp Asn Ala Gly Asn Tyr His Glu
            580                 585                 590

Leu Arg Ala Ile Gly Ser Arg Phe Leu Thr His His Leu
```

<210> SEQ ID NO 55
<211> LENGTH: 2211
<212> TYPE: DNA
<213> ORGANISM: Adeno-associated virus

<400> SEQUENCE: 55

| | | | | | |
|---|---|---|---|---|---|
| atggctgccg | atggttatct | tccagattgg | ctcgaggaca | acctctctga | gggcattcgc | 60 |
| gagtggtggg | acttgaaacc | tggagccccg | aagcccaaag | ccaaccagca | aaagcaggac | 120 |
| gacggccggg | tctggtgct | tcctggctac | aagtacctcg | acccttcaa | cggactcgac | 180 |
| aaggggagc | ccgtcaacgc | ggcggacgca | gcggccctcg | agcacgacaa | ggcctacgac | 240 |
| cagcagctca | aagcgggtga | caatccgtac | ctgcggtata | accacgccga | cgccgagttt | 300 |
| caggagcgtc | tgcaagaaga | tacgtctttt | gggggcaacc | tcgggcgagc | agtcttccag | 360 |
| gccaagaagc | gggttctcga | acctctcggt | ctggttgagg | aaggcgctaa | gacggctcct | 420 |
| ggaaagaaac | gtccggtaga | gcagtcgcca | aagagccag | actcctcctc | gggcatcggc | 480 |
| aagacaggcc | agcagcccgc | taaaaagaga | ctcaattttg | gtcagactgg | cgactcagag | 540 |
| tcagtccccg | atccacaacc | tctcggagaa | cctccagcaa | ccccgctgc | tgtgggacct | 600 |
| actacaatgg | cttcaggcgg | tggcgcacca | atggcagaca | ataacgaagg | cgccgacgga | 660 |
| gtgggtaatg | cctcaggaaa | ttggcattgc | gattccacat | ggctgggcga | cagagtcatc | 720 |
| accaccagca | cccgcacctg | ggccttgccc | acctacaata | accacctcta | caagcaaatc | 780 |
| tccagtgctt | caacggggc | cagcaacgac | aaccactact | tcggctacag | cacccccctgg | 840 |
| gggtattttg | atttcaacag | attccactgc | cacttttcac | cacgtgactg | gcagcgactc | 900 |
| atcaacaaca | attggggatt | ccggcccaag | agactcaact | tcaaactctt | caacatccaa | 960 |
| gtcaaggagg | tcacgacgaa | tgatggcgtc | acaaccatcg | ctaataacct | taccagcacg | 1020 |
| gttcaagtct | ctcggactc | ggagtaccag | cttccgtacg | tcctcggctc | tgcgcaccag | 1080 |
| ggctgcctcc | ctccgttccc | ggcggacgtg | ttcatgattc | cgcaatacgg | ctacctgacg | 1140 |
| ctcaacaatg | gcagccaagc | cgtgggacgt | tcatccttt | actgcctgga | atatttccct | 1200 |
| tctcagatgc | tgagaacggg | caacaacttt | accttcagct | acacctttga | ggaagtgcct | 1260 |
| ttccacagca | gctacgcgca | gcagccagag | ctggaccggc | tgatgaatcc | tctcatcgac | 1320 |
| caatacctgt | attacctgaa | cagaactcaa | aatcagtccg | gaagtgccca | aaacaaggac | 1380 |
| ttgctgttta | ccgtgggtc | tccagctggc | atgtctgttc | agcccaaaaa | ctggctacct | 1440 |
| ggaccctgtt | atcggcagca | gcgcgtttct | aaaacaaaaa | cagacaacaa | caacagcaat | 1500 |
| tttacctgga | ctggtgcttc | aaaatataac | ctcaatgggc | gtgaatccat | catcaaccct | 1560 |
| ggcactgcta | tggcctcaca | caaagacgac | gaagacaagt | tctttcccat | gagcggtgtc | 1620 |
| atgattttg | aaaagagag | cgccggagct | tcaaacactg | cattggacaa | tgtcatgatt | 1680 |
| acagacgaag | aggaaattaa | agccactaac | cctgtggcca | ccgaaagatt | tgggaccgtg | 1740 |
| gcagtcaatt | tccagagcag | cagcacagac | cctgcgaccg | gagatgtgca | tgctatggga | 1800 |
| gcattacctg | gcatggtgtg | gcaagataga | gacgtgtacc | tgcagggtcc | catttgggcc | 1860 |
| aaaattcctc | acacagatgg | acactttcac | ccgtctcctc | ttatgggcgg | ctttggactc | 1920 |
| aagaacccgc | ctcctcagat | cctcatcaaa | aacacgcctg | ttcctgcgaa | tcctccggcg | 1980 |
| gagttttcag | ctacaaagtt | tgcttcattc | atcacccaat | actccacagg | acaagtgagt | 2040 |
| gtggaaattg | aatgggagct | gcagaaagaa | aacagcaagc | gctggaatcc | cgaagtgcag | 2100 |

| | | | | |
|---|---|---|---|---|
| tacacatcca | attatgcaaa | atctgccaac | gttgatttta | ctgtggacaa caatggactt | 2160 |
| tatactgagc | ctcgccccat | tggcacccgt | taccttaccc | gtcccctgta a | 2211 |

<210> SEQ ID NO 56
<211> LENGTH: 1800
<212> TYPE: DNA
<213> ORGANISM: Adeno-associated virus

<400> SEQUENCE: 56

| | | | | | |
|---|---|---|---|---|---|
| acggctcctg | gaaagaaacg | tccggtagag | cagtcgccac | aagagccaga | ctcctcctcg | 60 |
| ggcatcggca | agacaggcca | gcagcccgct | aaaaagagac | tcaattttgg | tcagactggc | 120 |
| gactcagagt | cagtccccga | tccacaacct | ctcggagaac | ctccagcaac | cccgctgct | 180 |
| gtgggaccta | ctacaatggc | ttcaggcggt | ggcgcaccaa | tggcagacaa | taacgaaggc | 240 |
| gccgacggag | tgggtaatgc | ctcaggaaat | tggcattgcg | attccacatg | gctgggcgac | 300 |
| agagtcatca | ccaccagcac | ccgcacctgg | gccttgccca | cctacaataa | ccacctctac | 360 |
| aagcaaatct | ccagtgcttc | aacggggggcc | agcaacgaca | accactactt | cggctacagc | 420 |
| accccctggg | gtattttga | tttcaacaga | ttccactgcc | acttttcacc | acgtgactgg | 480 |
| cagcgactca | tcaacaacaa | ttggggattc | cggcccaaga | gactcaactt | caaactcttc | 540 |
| aacatccaag | tcaaggaggt | cacgacgaat | gatggcgtca | caaccatcgc | taataacctt | 600 |
| accagcacgg | ttcaagtctt | ctcggactcg | gagtaccagc | ttccgtacgt | cctcggctct | 660 |
| gcgcaccagg | gctgcctccc | tccgttcccg | gcggacgtgt | tcatgattcc | gcaatacggc | 720 |
| tacctgacgc | tcaacaatgg | cagccaagcc | gtgggacgtt | catccttta | ctgcctggaa | 780 |
| tatttccctt | ctcagatgct | gagaacgggc | aacaacttta | ccttcagcta | cacctttgag | 840 |
| gaagtgcctt | tccacagcag | ctacgcgcac | agccagagcc | tggaccggct | gatgaatcct | 900 |
| ctcatcgacc | aataccctgta | ttacctgaac | agaactcaaa | atcagtccgg | aagtgcccaa | 960 |
| aacaaggact | tgctgtttag | ccgtgggtct | ccagctggca | tgtctgttca | gcccaaaaac | 1020 |
| tggctacctg | gaccctgtta | tcggcagcag | cgcgtttcta | aaacaaaaac | agacaacaac | 1080 |
| aacagcaatt | ttacctggac | tggtgcttca | aaatataacc | tcaatgggcg | tgaatccatc | 1140 |
| atcaaccctg | gcactgctat | ggcctcacac | aaagacgacg | aagacaagtt | ctttcccatg | 1200 |
| agcggtgtca | tgattttggg | aaaagagagc | gccggagctt | caaacactgc | attggacaat | 1260 |
| gtcatgatta | cagacgaaga | ggaaattaaa | gccactaacc | ctgtggccac | cgaaagattt | 1320 |
| gggaccgtgg | cagtcaattt | ccagagcagc | agcacagacc | ctgcgaccgg | agatgtgcat | 1380 |
| gctatgggag | cattacctgg | catggtgtgg | caagatagag | acgtgtacct | gcagggtccc | 1440 |
| atttgggcca | aaattcctca | cacagatgga | cactttcacc | cgtctcctct | tatgggcggc | 1500 |
| tttggactca | agaacccgcc | tcctcagatc | ctcatcaaaa | acacgcctgt | tcctgcgaat | 1560 |
| cctccggcgg | agttttcagc | tacaaagttt | gcttcattca | tcacccaata | ctccacagga | 1620 |
| caagtgagtg | tggaaattga | atgggagctg | cagaaagaaa | acagcaagcg | ctggaatccc | 1680 |
| gaagtgcagt | acacatccaa | ttatgcaaaa | tctgccaacg | ttgattttac | tgtggacaac | 1740 |
| aatggacttt | atactgagcc | tcgccccatt | ggcacccgtt | accttacccg | tcccctgtaa | 1800 |

<210> SEQ ID NO 57
<211> LENGTH: 2208
<212> TYPE: DNA
<213> ORGANISM: Adeno-associated virus

<400> SEQUENCE: 57

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg accccagcc tctcggacag ccaccagcag cccctctgg tctgggaact      600
aatacgatgg ctacaggcag tggcgcacca atgcagaca taacgaggg cgccgacgga      660
gtgggtaatt cctcgggaaa ttggcattgc gattccacat ggatgggcga cagagtcatc     720
accaccagca cccgaacctg ggccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca aagactcatc     900
aacaacaact ggggattccg acccaagaga ctcaacttca gctctttaa cattcaagtc      960
aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcacctg     1140
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt ttcctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attcacacac cggacggaca ttttcacccc tctcccctca tgggtggatt cggacttaaa    1920
caccctcctc cacagattct catcaagaac acccccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gcccattgg caccagatac ctgactcgta atctgtaa                  2208
```

<210> SEQ ID NO 58
<211> LENGTH: 1797

<212> TYPE: DNA
<213> ORGANISM: Adeno-associated virus

<400> SEQUENCE: 58

```
acggctccgg gaaaaaagag gccggtagag cactctcctg tggagccaga ctcctcctcg      60
ggaaccggaa aggcgggcca gcagcctgca agaaaaagat tgaattttgg tcagactgga     120
gacgcagact cagtacctga cccccagcct ctcggacagc caccagcagc ccctctggt      180
ctgggaacta atacgatggc tacaggcagt ggcgcaccaa tggcagacaa taacgagggc     240
gccgacggag tgggtaattc ctcgggaaat tggcattgcg attccacatg gatgggcgac     300
agagtcatca ccaccagcac ccgaacctgg gccctgccca cctacaacaa ccacctctac     360
aaacaaattt ccagccaatc aggagcctcg aacgacaatc actactttgg ctacagcacc     420
ccttgggggt attttgactt caacagattc cactgccact tttcaccacg tgactggcaa     480
agactcatca acaacaactg gggattccga cccaagagac tcaacttcaa gctctttaac     540
attcaagtca aagaggtcac gcagaatgac ggtacgacga cgattgccaa taaccttacc     600
agcacggttc aggtgtttac tgactcggag taccagctcc cgtacgtcct cggctcggcg     660
catcaaggat gcctcccgcc gttcccagca gacgtcttca tggtgccaca gtatggatac     720
ctcacccctga acaacgggag tcaggcagta ggacgctctt cattttactg cctggagtac     780
tttccttctc agatgctgcg taccggaaac aactttacct tcagctacac ttttgaggac     840
gttcctttcc acagcagcta cgctcacagc cagagtctgg accgtctcat gaatcctctc     900
atcgaccagt acctgtatta cttgagcaga acaaacactc caagtggaac caccacgcag     960
tcaaggcttc agtttctca ggccggagcg agtgacattc gggaccagtc taggaactgg    1020
cttcctggac cctgttaccg ccagcagcga gtatcaaaga catctgcgga taacaacaac    1080
agtgaatact cgtggactgg agctaccaag taccacctca atggcagaga ctctctggtg    1140
aatccgggcc cggccatggc aagccacaag gacgatgaag aaaagttttt tcctcagagc    1200
ggggttctca tctttgggaa gcaaggctca gagaaaacaa atgtggacat tgaaaaggtc    1260
atgattacag acgaagagga aatcaggaca accaatcccg tggctacgga gcagtatggt    1320
tctgtatcta ccaacctcca gagaggcaac agacaagcag ctaccgcaga tgtcaacaca    1380
caaggcgttc ttccaggcat ggtctggcag gacagagatg tgtaccttca ggggcccatc    1440
tgggcaaaga ttccacacac ggacggacat tttcacccct ctccctcat gggtggattc    1500
ggacttaaaac accctcctcc acagattctc atcaagaaca ccccggtacc tgcgaatcct    1560
tcgaccacct tcagtgcggc aaagtttgct tccttcatca cacagtactc cacgggacag    1620
gtcagcgtgg agatcgagtg ggagctgcag aaggaaaaca gcaaacgctg gaatcccgaa    1680
attcagtaca cttccaacta caacaagtct gttaatgtgg actttactgt ggacactaat    1740
ggcgtgtatt cagagcctcg ccccattggc accagatacc tgactcgtaa tctgtaa      1797
```

<210> SEQ ID NO 59
<211> LENGTH: 2211
<212> TYPE: DNA
<213> ORGANISM: Adeno-associated virus

<400> SEQUENCE: 59

```
atggctgctg acggttatct tccagattgg ctcgaggaca accttctga aggcattcgt      60
gagtggtggg ctctgaaacc tggagtccct caacccaaag cgaaccaaca acaccaggac     120
aaccgtcggg gtcttgtgct tccgggttac aaataccctcg acccggtaa cggactcgac     180
```

```
aaaggagagc cggtcaacga ggcggacgcg gcagccctcg aacacgacaa agcttacgac      240
cagcagctca aggccggtga caacccgtac ctcaagtaca accacgccga cgccgagttt      300
caggagcgtc ttcaagaaga tacgtctttt gggggcaacc ttggcagagc agtcttccag      360
gccaaaaaga ggatccttga gcctcttggt ctggttgagg aagcagctaa aacggctcct      420
ggaaagaagg gggctgtaga tcagtctcct caggaaccgg actcatcatc tggtgttggc      480
aaatcgggca acagcctgc cagaaaaaga ctaaatttcg gtcagactgg agactcagag      540
tcagtcccag accctcaacc tctcggagaa ccaccagcag cccccacaag tttgggatct      600
aatacaatgg cttcaggcgg tggcgcacca atggcagaca ataacgaggg tgccgatgga      660
gtgggtaatt cctcaggaaa ttggcattgc gattcccaat ggctgggcga cagagtcatc      720
accaccagca ccagaacctg ggccctgccc acttacaaca accatctcta caagcaaatc      780
tccagccaat caggagcttc aaacgacaac cactactttg gctacagcac cccttggggg      840
tattttgact ttaacagatt ccactgccca ttctcaccac gtgactggca gcgactcatt      900
aacaacaact ggggattccg gcccaagaaa ctcagcttca gctcttcaa catccaagtt      960 agaggggtca cgcagaacga tggcacgacg actattgcca ataaccttac cagcacggtt     1020
caagtgttta cggactcgga gtatcagctc ccgtacgtgc tcgggtcggc gcaccaaggc     1080
tgtctcccgc cgtttccagc ggacgtcttc atggtccctc agtatggata cctcacctg      1140 aacaacggaa gtcaagcggt gggacgctca tcctttact gcctggagta cttcccttcg     1200
cagatgctaa ggactggaaa taacttccaa ttcagctata ccttcgagga tgtacctttt     1260
cacagcagct acgctcacag ccagagtttg gatcgcttga tgaatcctct tattgatcag     1320
tatctgtact acctgaacag aacgcaagga acaacctctg gaacaaccaa ccaatcacgg     1380
ctgcttttta gccaggctgg gcctcagtct atgtctttgc aggccagaaa ttggctacct     1440
gggccctgct accggcaaca gagactttca aagactgcta cgacaacaa caacagtaac     1500 tttccttgga cagcggccag caaatatcat ctcaatggcc gcgactcgct ggtgaatcca     1560
ggaccagcta tggccagtca caggacgat gaagaaaat ttttccctat gcacggcaat     1620
ctaatatttg gcaaagaagg gacaacggca agtaacgcag aattagataa tgtaatgatt     1680
acggatgaag aagagattcg taccaccaat cctgtggcaa cagagcagta tggaactgtg     1740
gcaaataact gcagagctc aaatacagct cccacgactg aactgtcaa tcatcagggg      1800 gccttacctg gcatggtgtg gcaagatcgt gacgtgtacc ttcaaggacc tatctgggca     1860
aagattcctc acacggatgg acactttcat ccttctcctc tgatgggagg ctttggactg     1920
aaacatccgc ctcctcaaat catgatcaaa aatactccgg taccggcaaa tcctccgacg     1980
actttcagcc cggccaagtt tgcttcattt atcactcagt actccactgg acaggtcagc     2040
gtggaaattg agtgggagct acagaaagaa acagcaaac gttggaatcc agagattcag     2100
tacacttcca actacaacaa gtctgttaat gtggactta ctgtagacac taatggtgtt     2160
tatagtgaac ctcgccctat tggaacccgg tatctcacac gaaacttgtg a             2211
```

<210> SEQ ID NO 60
<211> LENGTH: 1800
<212> TYPE: DNA
<213> ORGANISM: Adeno-associated virus

<400> SEQUENCE: 60

```
acggctcctg gaaagaaggg ggctgtagat cagtctcctc aggaaccgga ctcatcatct       60
ggtgttggca aatcgggcaa acagcctgcc agaaaaagac taaatttcgg tcagactgga      120
```

```
gactcagagt cagtcccaga ccctcaacct ctcggagaac caccagcagc ccccacaagt      180
ttgggatcta atacaatggc ttcaggcggt ggcgcaccaa tggcagacaa taacgagggt      240
gccgatggag tgggtaattc ctcaggaaat tggcattgcg attcccaatg gctgggcgac      300
agagtcatca ccaccagcac cagaacctgg gccctgccca cttacaacaa ccatctctac      360
aagcaaatct ccagccaatc aggagcttca aacgacaacc actactttgg ctacagcacc      420
ccttgggggt attttgactt taacagattc cactgccact tctcaccacg tgactggcag      480
cgactcatta acaacaactg gggattccgg cccaagaaac tcagcttcaa gctcttcaac      540
atccaagtta gaggggtcac gcagaacgat ggcacgacga ctattgccaa taaccttacc      600
agcacggttc aagtgtttac ggactcggag tatcagctcc cgtacgtgct cgggtcggcg      660
caccaaggct gtctcccgcc gtttccagcg gacgtcttca tggtcccctca gtatggatac      720 ctcacccctga caacggaagt caagcggtg ggacgctcat cctttactg cctggagtac      780 ttcccttcgc agatgctaag gactggaaat aacttccaat tcagctatac cttcgaggat      840
gtaccttttc acagcagcta cgctcacagc cagagtttgg atcgcttgat gaatcctctt      900
attgatcagt atctgtacta cctgaacaga acgcaaggaa caacctctgg aacaaccaac      960
caatcacggc tgcttttag ccaggctggg cctcagtcta tgtctttgca ggccagaaat     1020
tggctacctg ggccctgcta ccggcaacag agactttcaa agactgctaa cgacaacaac     1080
aacagtaact ttccttggac agcggccagc aaatatcatc tcaatggccg cgactcgctg     1140
gtgaatccag accagctat ggccagtcac aaggacgatg aagaaaaatt tttccctatg     1200
cacggcaatc taatatttgg caaagaaggg acaacggcaa gtaacgcaga attagataat     1260
gtaatgatta cggatgaaga agagattcgt accaccaatc ctgtggcaac agagcagtat     1320
ggaactgtgg caaataactt gcagagctca aatacagctc ccacgactgg aactgtcaat     1380 catcagggggg ccttacctgg catggtgtgg caagatcgtg acgtgtacct tcaaggacct     1440
atctgggcaa agattcctca cacggatgga cactttcatc cttctcctct gatgggaggc     1500
tttggactga acatccgcc tcctcaaatc atgatcaaaa atactccggt accggcaaat     1560
cctccgacga ctttcagccc ggccaagttt gcttcattta tcactcagta ctccactgga     1620
caggtcagcg tggaaattga gtgggagcta cagaaagaaa acagcaaacg ttggaatcca     1680
gagattcagt acacttccaa ctacaacaag tctgttaatg tggactttac tgtagacact     1740
aatggtgttt atagtgaacc tcgcccctatt ggaacccggt atctcacacg aaacttgtga     1800
```

<210> SEQ ID NO 61
<211> LENGTH: 2205
<212> TYPE: DNA
<213> ORGANISM: Adeno-associated virus

<400> SEQUENCE: 61

```
atgactgacg gttaccttcc agattggcta gaggacaacc tctctgaagg cgttcgagag       60
tggtgggcgc tgcaacctgg agcccctaaa cccaaggcaa atcaacaaca tcaggacaac      120
gctcggggtc ttgtgcttcc gggttacaaa tacctcggac ccggcaacgg actcgacaag      180
ggggaacccg tcaacgcagc ggacgcggca gccctcgagc acgacaaggc ctacgaccag      240
cagctcaagg ccggtgacaa cccctacctc aagtacaacc acgccgacgc ggagttccag      300
cagcggcttc agggcgacac atcgtttggg ggcaacctcg gcagagcagt cttccaggcc      360
aaaaagaggg ttcttgaacc tcttggtctg gttgagcaag cgggtgagac ggctcctgga      420
```

| | |
|---|---|
| aagaagagac cgttgattga atcccccag cagcccgact cctccacggg tatcggcaaa | 480 |
| aaaggcaagc agccggctaa aaagaagctc gttttcgaag acgaaactgg agcaggcgac | 540 |
| ggaccccctg agggatcaac ttccggagcc atgtctgatg acagtgagat gcgtgcagca | 600 |
| gctggcggag ctgcagtcga gggcggacaa ggtgccgatg gagtgggtaa tgcctcgggt | 660 |
| gattggcatt gcgattccac ctggtctgag ggccacgtca cgaccaccag caccagaacc | 720 |
| tgggtcttgc ccacctacaa caaccacctc tacaagcgac tcggagagag cctgcagtcc | 780 |
| aacacctaca acggattctc cacccctgg ggatactttg acttcaaccg cttccactgc | 840 |
| cacttctcac cacgtgactg gcagcgactc atcaacaaca actggggcat gcgacccaaa | 900 |
| gccatgcggg tcaaaatctt caacatccag gtcaaggagg tcacgacgtc gaacggcgag | 960 |
| acaacggtgg ctaataacct taccagcacg gttcagatct ttgcggactc gtcgtacgaa | 1020 |
| ctgccgtacg tgatggatgc gggtcaagag ggcagcctgc ctccttttcc caacgacgtc | 1080 |
| tttatggtgc cccagtacgg ctactgtgga ctggtgaccg caacacttc gcagcaacag | 1140 |
| actgacagaa atgccttcta ctgcctggag tactttcctt cgcagatgct gcggactggc | 1200 |
| aacaactttg aaattacgta cagttttgag aaggtgcctt ccactcgat gtacgcgcac | 1260 |
| agccagagcc tggaccggct gatgaaccct ctcatcgacc agtacctgtg gggactgcaa | 1320 |
| tcgaccacca ccggaaccac cctgaatgcc gggactgcca ccaccaactt taccaagctg | 1380 |
| cggcctacca acttttccaa ctttaaaaag aactggctgc ccgggccttc aatcaagcag | 1440 |
| cagggcttct caaagactgc caatcaaaac tacaagatcc ctgccaccgg gtcagacagt | 1500 |
| ctcatcaaat acgagacgca cagcactctg acggaagat ggagtgccct gaccccggga | 1560 |
| cctccaatgg ccacggctgg acctgcggac agcaagttca gcaacagcca gctcatcttt | 1620 |
| gcggggccta acagaacgg caacacgcc accgtacccg ggactctgat cttcacctct | 1680 |
| gaggaggagc tggcagccac caacgccacc gatacggaca tgtggggcaa cctacctggc | 1740 |
| ggtgaccaga gcaacagcaa cctgccgacc gtggacagac tgacagcctt gggagccgtg | 1800 |
| cctggaatgg tctggcaaaa cagagacatt tactaccagg gtcccatttg gccaagatt | 1860 |
| cctcataccg atggacactt tcaccccctca ccgctgattg gtgggtttgg gctgaaacac | 1920 |
| ccgcctcctc aaatttttat caagaacacc ccggtacctg cgaatcctgc aacgaccttc | 1980 |
| agctctactc cggtaaactc cttcattact cagtacagca ctggccaggt gtcggtgcag | 2040 |
| attgactggg agatccagaa ggagcggtcc aaacgctgga accccgaggt ccagtttacc | 2100 |
| tccaactacg gacagcaaaa ctctctgttg tgggctcccg atgcggctgg gaaatacact | 2160 |
| gagcctaggg ctatcggtac ccgctacctc acccaccacc tgtaa | 2205 |

<210> SEQ ID NO 62
<211> LENGTH: 1797
<212> TYPE: DNA
<213> ORGANISM: Adeno-associated virus

<400> SEQUENCE: 62

| | |
|---|---|
| acggctcctg gaaagaagag accgttgatt gaatccccc agcagcccga ctcctccacg | 60 |
| ggtatcggca aaaaggcaa gcagccggct aaaaagaagc tcgttttcga agacgaaact | 120 |
| ggagcaggcg acggaccccc tgagggatca acttccggag ccatgtctga tgacagtgag | 180 |
| atgcgtgcag cagctggcgg agctgcagtc gagggcggac aaggtgccga tggagtgggt | 240 |
| aatgcctcgg gtgattggca ttgcgattcc acctggtctg agggcacgt cacgaccacc | 300 |
| agcaccagaa cctgggtctt gcccacctac aacaaccacc tctacaagcg actcggagag | 360 |

```
agcctgcagt ccaacaccta caacggattc tccaccccct ggggatactt tgacttcaac      420
cgcttccact gccacttctc accacgtgac tggcagcgac tcatcaacaa caactggggc      480
atgcgaccca aagccatgcg ggtcaaaatc ttcaacatcc aggtcaagga ggtcacgacg      540
tcgaacggcg agacaacggt ggctaataac cttaccagca cggttcagat ctttgcggac      600
tcgtcgtacg aactgccgta cgtgatggat gcgggtcaag agggcagcct gcctcctttt      660
cccaacgacg tctttatggt gccccagtac ggctactgtg gactggtgac cggcaacact      720
tcgcagcaac agactgacag aaatgccttc tactgcctgg agtactttcc ttcgcagatg      780
ctgcggactg caacaacttt gaaattacg tacagttttg agaaggtgcc tttccactcg      840
atgtacgcgc acagccagag cctggaccgg ctgatgaacc ctctcatcga ccagtacctg      900
tggggactgc aatcgaccac caccggaacc accctgaatg ccgggactgc caccaccaac      960
tttaccaagc tgcggcctac caacttttcc aactttaaaa agaactggct gcccgggcct     1020
tcaatcaagc agcagggctt ctcaaagact gccaatcaaa actacaagat ccctgccacc     1080
gggtcagaca gtctcatcaa atacgagacg cacagcactc tggacggaag atggagtgcc     1140 ctgaccccg gacctccaat ggccacggct ggacctgcgg acagcaagtt cagcaacagc     1200
cagctcatct ttgcggggcc taaacagaac ggcaacacgg ccaccgtacc cgggactctg     1260
atcttcacct ctgaggagga gctggcagcc accaacgcca ccgatacgga catgtgggc      1320 aacctacctg gcggtgacca gagcaacagc aacctgccga ccgtggacag actgacagcc     1380
ttgggagccg tgcctggaat ggtctggcaa aacagagaca tttactacca gggtcccatt     1440
tgggccaaga ttcctcatac cgatggacac tttcaccct caccgctgat ggtgggttt       1500 gggctgaaac acccgcctcc tcaaattttt atcaagaaca ccccggtacc tgcgaatcct     1560
gcaacgacct tcagctctac tccggtaaac tccttcatta ctcagtacag cactggccag     1620
gtgtcggtgc agattgactg ggagatccag aaggagcggt ccaaacgctg aaccccgag      1680 gtccagttta cctccaacta cggacagcaa aactctctgt tgtgggctcc cgatgcggct     1740
gggaaataca ctgagcctag ggctatcggt acccgctacc tcacccacca cctgtaa       1797

<210> SEQ ID NO 63
<211> LENGTH: 2175
<212> TYPE: DNA
<213> ORGANISM: Adeno-associated virus

<400> SEQUENCE: 63 atgtctttg ttgatcaccc tccagattgg ttggaagaag ttggtgaagg tcttcgcgag        60 ttttgggcc ttgaagcggg cccaccgaaa ccaaaaccca atcagcagca tcaagatcaa       120
gcccgtggtc ttgtgctgcc tggttataac tatctcggac ccggaaacgg tctcgatcga      180
ggagagcctg tcaacagggc agacgaggtc gcgcgagagc acgacatctc gtacaacgag      240
cagcttgagg cgggagacaa cccctacctc aagtacaacc acgcggacgc cgagtttcag      300
gagaagctcg ccgacgacac atccttcggg ggaaacctcg gaaaggcagt ctttcaggcc      360
aagaaaaggg ttctcgaacc ttttggcctg gttgagagg gtgctaagac ggcccctacc      420
ggaaagcgga tagacgacca cttttccaaaa gaaagaagg ctcggaccga agaggactcc      480
aagccttcca cctcgtcaga cgccgaagct ggacccagcg atcccagca gctgcaaatc      540 ccagcccaac cagcctcaag tttggagct gatacaatgt ctgcggggag tggcggccca      600
ttgggcgaca ataaccaagg tgccgatgga gtgggcaatg cctcgggaga ttggcattgc      660
```

```
gattccacgt ggatggggga cagagtcgtc accaagtcca cccgaacctg ggtgctgccc      720
agctacaaca accaccagta ccgagagatc aaaagcggct ccgtcgacgg aagcaacgcc      780
aacgcctact ttggatacag cacccctgg gggtactttg actttaaccg cttccacagc       840
cactggagcc cccgagactg gcaaagactc atcaacaact actggggctt cagaccccgg      900
tccctcagag tcaaaatctt caacattcaa gtcaagagg tcacggtgca ggactccacc       960
accaccatcg ccaacaacct cacctccacc gtccaagtgt ttacggacga cgactaccag     1020 ctgcctacg tcgtcggcaa cgggaccgag ggatgcctgc cggccttccc tccgcaggtc      1080
tttacgctgc cgcagtacgg ttacgcgacg ctgaaccgcg acaacacaga aaatcccacc     1140
gagaggagca gcttcttctg cctagagtac tttcccagca agatgctgag aacgggcaac     1200
aactttgagt ttacctacaa ctttgaggag gtgcccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatgagct cgagggcgcg     1500 agttaccagg tgccccgca gccgaacggc atgaccaaca cctccaggg cagcaacacc      1560 tatgccctgg agaacactat gatcttcaac agccagccgg cgaacccggg caccaccgcc     1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca cgtgtggat ggagagggac      1800 gtgtacctcc aaggacccat ctgggccaag atcccagaga cggggcgca ctttcacccc     1860 tctccggcca tgggcggatt cggactcaaa caccccaccgc ccatgatgct catcaagaac    1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgacccca gtttgtggac    2100 tttgccccgg acagcaccgg ggaatacaga accaccagac tatcggaac ccgatacctt     2160 accccgacccc tttaa                                                    2175
```

<210> SEQ ID NO 64
<211> LENGTH: 1767
<212> TYPE: DNA
<213> ORGANISM: Adeno-associated virus

<400> SEQUENCE: 64

```
acggcccta ccggaaagcg gatagacgac cactttccaa aaagaaagaa ggctcggacc       60
gaagaggact ccaagccttc cacctcgtca gacgccgaag ctggaccag cggatcccag      120 cagctgcaaa tccagcccca accagcctca agtttgggag ctgatacaat gtctgcggga    180
ggtggcggcc cattgggcga caataaccaa ggtgccgatg agtgggcaa tgcctcggga    240 gattggcatt gcgattccac gtggatgggg gacagagtcg tcaccaagtc caccgaacc     300 tgggtgctgc ccagctacaa caaccaccag taccgagaga tcaaaagcgg ctccgtcgac    360
ggaagcaacg ccaacgccta cttggatac agccaccccct gggggtactt tgactttaac    420
cgcttccaca gccactggag cccccgagac tggcaaagac tcatcaacaa ctactgggc     480 ttcagacccc ggtccctcag agtcaaaatc ttcaacattc aagtcaaga ggtcacggtg     540 caggactcca ccaccaccat cgccaacaac ctcacctcca ccgtccaagt gtttacggac    600
```

```
gacgactacc agctgcccta cgtcgtcggc aacgggaccg agggatgcct gccggccttc      660
cctccgcagg tctttacgct gccgcagtac ggttacgcga cgctgaaccg cgacaacaca      720
gaaaatccca ccgagaggag cagcttcttc tgcctagagt actttcccag caagatgctg      780
agaacgggca acaactttga gtttacctac aactttgagg aggtgccctt ccactccagc      840
ttcgctccca gtcagaacct gttcaagctg gccaacccgc tggtggacca gtacttgtac      900
cgcttcgtga gcacaaataa cactggcgga gtccagttca acaagaacct ggccgggaga      960
tacgccaaca cctacaaaaa ctggttcccg gggcccatgg gccgaaccca gggctggaac     1020
ctgggctccg gggtcaaccg cgccagtgtc agcgccttcg ccacgaccaa taggatggag     1080
ctcgagggcg cgagttacca ggtgcccccg cagccgaacg gcatgaccaa caacctccag     1140
ggcagcaaca cctatgccct ggagaacact atgatcttca acagccagcc ggcgaacccg     1200
ggcaccaccg ccacgtacct cgagggcaac atgctcatca ccagcgagag cgagacgcag     1260
ccggtgaacc gcgtggcgta caacgtcggc gggcagatgg ccaccaacaa ccagagctcc     1320
accactgccc ccgcgaccgg cacgtacaac ctccaggaaa tcgtgccggg cagcgtgtgg     1380
atggagaggg acgtgtacct ccaaggaccc atctgggcca agatcccaga cacggggcg      1440 cactttcacc cctctccggc catgggcgga ttcggactca acacccacc gcccatgatg     1500 ctcatcaaga acacgcctgt gccggaaat atcaccagct ctcggacgt gcccgtcagc      1560 agcttcatca cccagtacag caccgggcag gtcaccgtgg agatggagtg ggagctcaag     1620
aaggaaaact ccaagaggtg gaacccagag atccagtaca caaacaacta caacgacccc     1680
cagtttgtgg actttgcccc ggacagcacc ggggaataca aaccaccag acctatcgga     1740 acccgatacc ttacccgacc cctttaa                                          1767

<210> SEQ ID NO 65
<211> LENGTH: 2211
<212> TYPE: DNA
<213> ORGANISM: Adeno-associated virus

<400> SEQUENCE: 65
atggctgccg atggttatct tccagattgg ctcgaggaca acctctctga gggcattcgc       60
gagtggtggg acttgaaacc tggagccccg aaacccaaag ccaaccagca aaagcaggac      120
gacggccggg gtctggtgct tcctggctac aagtacctcg acccttcaa cggactcgac       180 aaggggagc cgtcaacgc ggcggatgca gcggccctcg agcacgacaa ggcctacgac       240
cagcagctca aagcgggtga caatccgtac ctgcggtata accacgccga cgccgagttt      300
caggagcgtc tgcaagaaga tacgtctttt ggggggcaacc tcgggcgagc agtcttccag      360
gccaagaaga gggttctcga accttttggt ctggttgagg aaggtgctaa gacggctcct      420
ggaaagaaac gtccggtaga gcagtcgcca caagagccag actcctcctc gggcattggc      480
aagacaggcc agcagcccgc taaaaagaga ctcaattttg gtcagactgg cgactcagag      540
tcagtccccg acccacaacc tctcggagaa cctccagcaa ccccgctgc tgtgggacct      600 actacaatgg cttcaggcgg tggcgcacca atggcagaca ataacgaagg cgccgacgga      660
gtgggtaatg cctcaggaaa ttggcattgc gattccacat ggctgggcga cagagtcatc      720
accaccagca cccgaacatg gccttgccc acctataaca accacctcta caagcaaatc      780
tccagtgctt caacggggc cagcaacgac aaccactact cggctacag cacccctgg      840 gggtattttg atttcaacag attccactgc catttctcac cacgtgactg cagcgactc      900
```

| | |
|---|---|
| atcaacaaca attggggatt ccggcccaag agactcaact tcaagctctt caacatccaa | 960 |
| gtcaaggagg tcacgacgaa tgatggcgtc acgaccatcg ctaataacct taccagcacg | 1020 |
| gttcaagtct tctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |
| ctcaacaatg gcagccaggc agtgggacgg tcatccttt actgcctgga atatttccca | 1200 |
| tcgcagatgc tgagaacggg caataacttt accttcagct acaccttcga ggacgtgcct | 1260 |
| ttccacagca gctacgcgca cagccagagc ctggaccggc tgatgaatcc tctcatcgac | 1320 |
| cagtacctgt attacctgaa cagaactcag aatcagtccg gaagtgccca aaacaaggac | 1380 |
| ttgctgttta gccggggggtc tccagctggc atgtctgttc agcccaaaaa ctggctacct | 1440 |
| ggaccctgtt accggcagca gcgcgtttct aaaacaaaaa cagacaacaa caacagcaac | 1500 |
| tttacctgga ctggtgcttc aaaatataac cttaatgggc gtgaatctat aatcaaccct | 1560 |
| ggcactgcta tggcctcaca caaagacgac aaagacaagt tctttcccat gagcggtgtc | 1620 |
| atgattttg gaaaggagag cgccggagct tcaaacactg cattggacaa tgtcatgatc | 1680 |
| acagacgaag aggaaatcaa agccactaac cccgtggcca ccgaaagatt tgggactgtg | 1740 |
| gcagtcaatc tccagagcag cagcacagac cctgcgaccg gagatgtgca tgttatggga | 1800 |
| gccttacctg gaatggtgtg gcaagacaga gacgtatacc tgcagggtcc tatttgggcc | 1860 |
| aaaattcctc acacggatgg acactttcac ccgtctcctc tcatgggcgg ctttggactt | 1920 |
| aagcacccgc ctcctcagat cctcatcaaa acacgcctg ttcctgcgaa tcctccggca | 1980 |
| gagttttcgg ctacaaagtt tgcttcattc atcacccagt attccacagg acaagtgagc | 2040 |
| gtggagattg aatgggagct gcagaaagaa aacagcaaac gctggaatcc cgaagtgcag | 2100 |
| tatacatcta actatgcaaa atctgccaac gttgatttca ctgtggacaa caatggactt | 2160 |
| tatactgagc ctcgccccat tggcacccgt tacctcaccc gtcccctgta a | 2211 |

<210> SEQ ID NO 66
<211> LENGTH: 1800
<212> TYPE: DNA
<213> ORGANISM: Adeno-associated virus

<400> SEQUENCE: 66

| | |
|---|---|
| acggctcctg gaaagaaacg tccggtagag cagtcgccac aagagccaga ctcctcctcg | 60 |
| ggcattggca agacaggcca gcagcccgct aaaaagagac tcaattttgg tcagactggc | 120 |
| gactcagagt cagtccccga cccacaacct ctcggagaac ctccagcaac cccgctgct | 180 |
| gtgggaccta ctacaatggc ttcaggcggt ggcgcaccaa tggcagacaa taacgaaggc | 240 |
| gccgacggag tgggtaatgc ctcaggaaat tggcattgcg attccacatg gctgggcgac | 300 |
| agagtcatca ccaccagcac ccgaacatgg gccttgccca cctataacaa ccacctctac | 360 |
| aagcaaatct ccagtgcttc aacgggggcc agcaacgaca ccactactt cggctacagc | 420 |
| accccctggg ggtattttga tttcaacaga ttccactgcc atttctcacc acgtgactgg | 480 |
| cagcgactca tcaacaacaa ttgggggatt cggcccaaga gactcaactt caagctcttc | 540 |
| aacatccaag tcaaggaggt cacgacgaat gatggcgtca cgaccatcgc taataacctt | 600 |
| accagcacgg ttcaagtctt ctcggactcg agtaccagt tgccgtacgt cctcggctct | 660 |
| gcgcaccagg ctgcctccc tccgttcccg gcggacgtgt tcatgattcc gcagtacggc | 720 |
| tacctaacgc tcaacaatgg cagccaggca gtgggacggt catcccttta ctgcctggaa | 780 |
| tatttcccat cgcagatgct gagaacgggc aataacttta ccttcagcta caccttcgag | 840 |

```
gacgtgcctt tccacagcag ctacgcgcac agccagagcc tggaccggct gatgaatcct    900
ctcatcgacc agtacctgta ttacctgaac agaactcaga atcagtccgg aagtgcccaa    960
aacaaggact tgctgtttag ccgggggtct ccagctggca tgtctgttca gcccaaaaac   1020
tggctacctg gaccctgtta ccggcagcag cgcgtttcta aaacaaaaac agacaacaac   1080
aacagcaact ttacctggac tggtgcttca aaatataacc ttaatgggcg tgaatctata   1140
atcaaccctg cactgctat ggcctcacac aaagacgaca agacaagtt ctttcccatg    1200 agcggtgtca tgattttgg aaaggagagc gccggagctt caaacactgc attggacaat    1260
gtcatgatca cagacgaaga ggaaatcaaa gccactaacc ccgtggccac cgaaagattt    1320
gggactgtgg cagtcaatct ccagagcagc agcacagacc ctgcgaccgg agatgtgcat    1380
gttatgggag ccttacctgg aatggtgtgg caagacagag acgtatacct gcagggtcct    1440
atttgggcca aaattcctca cacggatgga cactttcacc cgtctcctct catgggcggc    1500
tttggactta agcacccgcc tcctcagatc ctcatcaaaa acacgcctgt tcctgcgaat    1560
cctccggcag agttttcggc tacaaagttt gcttcattca tcacccagta ttccacagga   1620
caagtgagcg tggagattga atgggagctg cagaaagaaa acagcaaacg ctggaatccc   1680
gaagtgcagt atacatctaa ctatgcaaaa tctgccaacg ttgatttcac tgtggacaac   1740
aatggacttt atactgagcc tcgccccatt ggcacccgtt acctcacccg tcccctgtaa   1800

<210> SEQ ID NO 67
<211> LENGTH: 2214
<212> TYPE: DNA
<213> ORGANISM: Adeno-associated virus

<400> SEQUENCE: 67
atggctgccg atggttatct tccagattgg ctcgaggaca acctctctga gggcattcgc     60
gagtggtggg acctgaaacc tggagccccg aaacccaaag ccaaccagca aaagcaggac    120
aacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca agcgggtga caatccgtac ctgcggtata accacgccga cgccgagttt    300
caggagcgtc tgcaagaaga tacgtcattt ggggcaacc tcgggcgagc agtcttccag    360
gccaagaagc gggttctcga acctctcggt ctggttgagg aaggcgctaa gacggctcct    420
gcaaagaaga ccggtagag ccgtcacct cagcgttccc ccgactcctc cacgggcatc    480
ggcaagaaag gccagcagcc cgccagaaag agactcaatt tcggtcagac tggcgactca    540
gagtcagtcc ccgaccctca acctctcgga gaacctccag cagcgccctc tagtgtggga   600
tctggtacag tggctgcagg cggtggcgca ccaatggcag acaataacga aggtgccgac   660
ggagtgggta atgcctcagg aaattggcat tgcgattcca tggctgggc gacagagtc    720 attaccacca gcacccgaac ctgggccctg cccacctaca acaaccacct ctacaagcaa    780
atctccagtg aaactgcagg tagtaccaac gacaacacct acttcggcta cagcaccccc    840
tgggggtatt ttgactttaa cagattccac tgccacttct caccacgtga ctggcagcga    900
ctcatcaaca caactgggg attccggccc aagaagctgc ggttcaagct cttcaacatc    960
caggtcaagg aggtcacgac gaatgacggc gttacgacca tcgctaataa ccttaccagc   1020
acgattcagg tattctcgga ctcggaatac cagctgccgt acgtcctcgg ctctgcgcac   1080
cagggctgcc tgcctccgtt cccggcggac gtcttcatga ttcctcagta cggctacctg   1140
```

```
actctcaaca atggcagtca gtctgtggga cgttcctcct tctactgcct ggagtacttc    1200
ccctctcaga tgctgagaac gggcaacaac tttgagttca gctacagctt cgaggacgtg    1260
cctttccaca gcagctacgc acacagccag agcctggacc ggctgatgaa tcccctcatc    1320
gaccagtact tgtactacct ggccagaaca cagagtaacc caggaggcac agctggcaat    1380
cgggaactgc agttttacca gggcgggcct tcaactatgg ccgaacaagc caagaattgg    1440
ttacctggac cttgcttccg gcaacaaaga gtctccaaaa cgctggatca aaacaacaac    1500
agcaactttg cttggactgg tgccaccaaa tatcacctga cggcagaaa ctcgttggtt    1560 aatcccggcg tcgccatggc aactcacaag gacgacgagg accgcttttt cccatccagc    1620
ggagtcctga ttttttggaaa aactggagca actaacaaaa ctacattgga aaatgtgtta    1680
atgacaaatg aagaagaaat tcgtcctact aatcctgtag ccacgaaga atacgggata    1740 gtcagcagca acttacaagc ggctaatact gcagcccaga cacaagttgt caacaaccag    1800
ggagccttac ctggcatggt ctggcagaac cgggacgtgt acctgcaggg tcccatctgg    1860
gccaagattc ctcacacgga tggcaacttt caccccgtctc ctttgatggg cggcttttgga    1920 cttaaacatc cgcctcctca gatcctgatc aagaacactc ccgttcccgc taatcctccg    1980
gaggtgttta ctcctgccaa gtttgcttcg ttcatcacac agtacagcac cggacaagtc    2040
agcgtggaaa tcgagtggga gctgcagaag gaaaacagca gcgctggaaa cccggagatt    2100
cagtacacct ccaactttga aaagcagact ggtgtggact tgccgttga cagccagggt    2160 gtttactctg agcctcgccc tattggcact cgttacctca cccgtaatct gtaa          2214

<210> SEQ ID NO 68
<211> LENGTH: 1803
<212> TYPE: DNA
<213> ORGANISM: Adeno-associated virus

<400> SEQUENCE: 68
acggctcctg caaagaagag accggtagag ccgtcacctc agcgttcccc cgactcctcc      60
acgggcatcg gcaagaaagg ccagcagccc gccagaaaga gactcaattt cggtcagact     120
ggcgactcag agtcagtccc cgaccctcaa cctctcggag aacctccagc agcgccctct     180
agtgtgggat ctggtacagt ggctgcaggc ggtggcgcac caatggcaga caataacgaa     240
ggtgccgacg gagtgggtaa tgcctcagga aattggcatt gcgattccac atggctgggc     300
gacagagtca ttaccaccag cacccgaacc tgggccctgc ccacctacaa caaccacctc     360
tacaagcaaa tctccagtga aactgcaggt agtaccaacg acaacaccta cttcggctac     420 agcacccct gggggtattt tgactttaac agattccact gccacttctc accacgtgac     480 tgcagcgac tcatcaacaa caactgggga ttccggccca agaagctgcg gttcaagctc     540
ttcaacatcc aggtcaagga ggtcacgacg aatgacggcg ttacgaccat cgctaataac     600
cttaccagca cgattcaggt attctcggac tcggaatacc agctgccgta cgtcctcggc     660
tctgcgcacc agggctgcct gcctccgttc ccggcggacg tcttcatgat tcctcagtac     720
ggctacctga ctctcaacaa tggcagtcag tctgtgggac gttcctcctt ctactgcctg     780
gagtacttcc cctctcagat gctgagaacg gcaacaact ttgagttcag ctacagcttc     840
gaggacgtgc ctttccacag cagctacgca cacagccaga gcctggaccg gctgatgaat     900
cccctcatcg accagtactt gtactacctg ccagaacac agagtaaccc aggaggcaca     960
gctggcaatc gggaactgca gttttaccag ggcgggcctt caactatggc cgaacaagcc    1020
aagaattggt tacctggacc ttgcttccgg caacaaagag tctccaaaac gctggatcaa    1080
```

| | |
|---|---|
| aacaacaaca gcaactttgc ttggactggt gccaccaaat atcacctgaa cggcagaaac | 1140 |
| tcgttggtta atcccggcgt cgccatggca actcacaagg acgacgagga ccgcttttc | 1200 |
| ccatccagcg gagtcctgat ttttggaaaa actggagcaa ctaacaaaac tacattggaa | 1260 |
| aatgtgttaa tgacaaatga agaagaaatt cgtcctacta atcctgtagc cacggaagaa | 1320 |
| tacgggatag tcagcagcaa cttacaagcg gctaatactg cagcccagac acaagttgtc | 1380 |
| aacaaccagg gagccttacc tggcatggtc tggcagaacc gggacgtgta cctgcagggt | 1440 |
| cccatctggg ccaagattcc tcacacggat ggcaactttc accgtctcc tttgatgggc | 1500 |
| ggctttggac ttaaacatcc gcctcctcag atcctgatca gaacactcc cgttcccgct | 1560 |
| aatcctccgg aggtgtttac tcctgccaag tttgcttcgt tcatcacaca gtacagcacc | 1620 |
| ggacaagtca gcgtggaaat cgagtgggag ctgcagaagg aaaacagcaa gcgctggaac | 1680 |
| ccggagattc agtacacctc caactttgaa aagcagactg tgtggactt tgccgttgac | 1740 |
| agccagggtg tttactctga gcctcgccct attggcactc gttacctcac ccgtaatctg | 1800 |
| taa | 1803 |

```
<210> SEQ ID NO 69
<211> LENGTH: 2217
<212> TYPE: DNA
<213> ORGANISM: Adeno-associated virus

<400> SEQUENCE: 69
```

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg accccttcaa cggactcgac | 180 |
| aaggggagc ccgtcaacgc ggcggacgca gcggccctcg agcacgacaa ggcctacgac | 240 |
| cagcagctgc aggcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaga gaccggtaga gccatcaccc cagcgttctc cagactcctc tacgggcatc | 480 |
| ggcaagaaag ccaacagcc cgccagaaaa agactcaatt ttggtcagac tggcgactca | 540 |
| gagtcagttc cagaccctca acctctcgga gaacctccag cagcgccctc tggtgtggga | 600 |
| cctaatacaa tggctgcagg cggtggcgca ccaatggcag acaataacga aggcgccgac | 660 |
| ggagtgggta gttcctcggg aaattggcat tgcgattcca catggctggg cgacagagtc | 720 |
| atcaccacca gcacccgaac ctgggccctg cccacctaca acaaccacct ctacaagcaa | 780 |
| atctccaacg gacatcggg aggagccacc aacgacaaca cctacttcgg ctacagcacc | 840 |
| ccctgggggt attttgactt taacagattc cactgccact tttcaccacg tgactggcag | 900 |
| cgactcatca caacaactg gggattccgg cccaagagac tcagcttcaa gctcttcaac | 960 |
| atccaggtca aggaggtcac gcagaatgaa ggcaccaaga ccatcgccaa taacctcacc | 1020 |
| agcaccatcc aggtgtttac ggactcggag taccagctgc cgtacgttct cggctctgcc | 1080 |
| caccagggct gcctgcctcc gttcccggcg acgtgttca tgattcccca gtacggctac | 1140 |
| ctaacactca acaacggtag tcaggccgtg gacgctcct ccttctactg cctggaatac | 1200 |
| tttccttcgc agatgctgag aaccggcaac aacttccagt ttacttacac cttcgaggac | 1260 |
| gtgccttttc acagcagcta cgcccacagc cagagcttgg accggctgat gaatcctctg | 1320 |

| | |
|---|---|
| attgaccagt acctgtacta cttgtctcgg actcaaacaa caggaggcac ggcaaatacg | 1380 |
| cagactctgg gcttcagcca aggtgggcct aatacaatgg ccaatcaggc aaagaactgg | 1440 |
| ctgccaggac cctgttaccg ccaacaacgc gtctcaacga caaccgggca aacaacaat | 1500 |
| agcaactttg cctggactgc tgggaccaaa taccatctga atggaagaaa ttcattggct | 1560 |
| aatcctggca tcgctatggc aacacacaaa gacgacgagg agcgttttttt tcccagtaac | 1620 |
| gggatcctga tttttggcaa acaaaatgct gccagagaca atgcggatta cagcgatgtc | 1680 |
| atgctcacca gcgaggaaga aatcaaaacc actaaccctg tggctacaga ggaatacggt | 1740 |
| atcgtggcag ataacttgca gcagcaaaac acggctcctc aaattggaac tgtcaacagc | 1800 |
| caggggggcct acccggtat ggtctggcag aaccgggacg tgtacctgca gggtcccatc | 1860 |
| tgggccaaga ttcctcacac ggacggcaac ttccacccgt ctccgctgat gggcggcttt | 1920 |
| ggcctgaaac atcctccgcc tcagatcctg atcaagaaca cgcctgtacc tgcggatcct | 1980 |
| ccgaccacct tcaaccagtc aaagctgaac tctttcatca cgcaatacag caccggacag | 2040 |
| gtcagcgtgg aaattgaatg ggagctgcag aaggaaaaca gcaagcgctg gaaccccgag | 2100 |
| atccagtaca cctccaacta ctacaaatct acaagtgtgg actttgctgt taatacagaa | 2160 |
| ggcgtgtact ctgaaccccg ccccattggc acccgttacc tcacccgtaa tctgtaa | 2217 |

<210> SEQ ID NO 70
<211> LENGTH: 1806
<212> TYPE: DNA
<213> ORGANISM: Adeno-associated virus

<400> SEQUENCE: 70

| | |
|---|---|
| acggctcctg gaaagaagag accggtagag ccatcacccc agcgttctcc agactcctct | 60 |
| acgggcatcg gcaagaaagg ccaacagccc gccagaaaaa gactcaattt tggtcagact | 120 |
| ggcgactcag agtcagttcc agaccctcaa cctctcggag aacctccagc agcgccctct | 180 |
| ggtgtgggac ctaatacaat ggctgcaggc ggtggcgcac caatggcaga caataacgaa | 240 |
| ggcgccgacg gagtgggtag ttcctcggga aattggcatt gcgattccac atggctgggc | 300 |
| gacagagtca tcaccaccag cacccgaacc tgggccctgc ccacctacaa caaccacctc | 360 |
| tacaagcaaa tctccaacgg gacatcggga ggagccacca cgacaacac ctacttcggc | 420 |
| tacagcaccc cctgggggta ttttgacttt aacagattcc actgccactt ttcaccacgt | 480 |
| gactggcagc gactcatcaa caacaactgg ggattccggc caagagact cagcttcaag | 540 |
| ctcttcaaca tccaggtcaa ggaggtcacg cagaatgaag caccaagac catcgccaat | 600 |
| aacctcacca gcaccatcca ggtgtttacg gactcggagt accagctgcc gtacgttctc | 660 |
| ggctctgccc accagggctg cctgcctccg ttcccggcgg acgtgttcat gattccccag | 720 |
| tacggctacc taacactcaa caacgggagt caggccgtgg gacgctcctc cttctactgc | 780 |
| ctggaatact ttccttcgca gatgctgaga accggcaaca cttccagtt tacttacacc | 840 |
| ttcgaggacg tgccttttca cagcagctac gcccacagcc agagcttgga ccggctgatg | 900 |
| aatcctctga ttgaccagta cctgtactac ttgtctcgga ctcaaacaac aggaggcacg | 960 |
| gcaaatacgc agactctggg cttcagccaa ggtgggccta atacaatggc caatcaggca | 1020 |
| aagaactggc tgccaggacc ctgttaccgc caacaacgcg tctcaacgac aaccgggcaa | 1080 |
| aacaacaata gcaactttgc ctggactgct gggaccaaat accatctgaa tggaagaaat | 1140 |
| tcattggcta atcctggcat cgctatggca acacacaaag acgacgagga gcgttttttt | 1200 |
| cccagtaacg ggatcctgat ttttggcaaa caaaatgctg ccagagacaa tgcggattac | 1260 |

```
agcgatgtca tgctcaccag cgaggaagaa atcaaaacca ctaaccctgt ggctacagag    1320
gaatacggta tcgtggcaga taacttgcag cagcaaaaca cggctcctca aattggaact    1380
gtcaacagcc aggggggcctt acccggtatg gtctggcaga accgggacgt gtacctgcag    1440
ggtcccatct gggccaagat tcctcacacg gacggcaact tccacccgtc tccgctgatg    1500
ggcggctttg gcctgaaaca tcctccgcct cagatcctga tcaagaacac gcctgtacct    1560
gcggatcctc cgaccacctt caaccagtca agctgaact ctttcatcac gcaatacagc      1620
accggacagg tcagcgtgga aattgaatgg gagctgcaga aggaaaacag caagcgctgg    1680
aaccccgaga tccagtacac ctccaactac tacaaatcta caagtgtgga ctttgctgtt    1740
aatacagaag gcgtgtactc tgaaccccgc cccattggca cccgttacct cacccgtaat    1800
ctgtaa                                                                1806

<210> SEQ ID NO 71
<211> LENGTH: 2211
<212> TYPE: DNA
<213> ORGANISM: Adeno-associated virus

<400> SEQUENCE: 71
atggctgccg atggttatct tccagattgg ctcgaggaca accttagtga aggaattcgc     60
gagtggtggg cttgaaaccc tggagccct caacccaagg caaatcaaca acatcaagac     120
aacgctcgag gtcttgtgct tccgggttac aaataccttg acccggcaa cggactcgac     180 aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctcgc gggtattggc    480 aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca taacgaagg tgccgatgga    660 gtgggtagtt cctcgggaaa ttggcattgc gattcccaat ggctggggga cagagtcatc    720
accaccagca cccgaacctg ggccctgccc acctacaaca tcacctcta caagcaaatc    780 tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg tcggctcac    1080 gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
```

```
tttgcttggc ctggagcttc ttcttgggct ctcaatggac gtaatagctt gatgaatcct   1560
ggacctgcta tggccagcca caaagaagga gaggaccgtt tctttccttt gtctggatct   1620 ttaattttg gcaaacaagg aactggaaga caacgtgg atgcggacaa agtcatgata     1680
accaacgaag aagaaattaa actactaac ccggtagcaa cggagtccta tggacaagtg    1740
gccacaaacc accagagtgc caagcacag cgcagaccg gctgggttca aaaccaagga    1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211

<210> SEQ ID NO 72
<211> LENGTH: 1800
<212> TYPE: DNA
<213> ORGANISM: Adeno-associated virus

<400> SEQUENCE: 72
acggctcctg gaaagaagag gcctgtagag cagtctcctc aggaaccgga ctcctccgcg     60
ggtattggca aatcgggtgc acagcccgct aaaaagagac tcaatttcgg tcagactggc    120
gacacagagt cagtcccaga ccctcaacca atcggagaac ctcccgcagc cccctcaggt    180
gtgggatctc ttacaatggc ttcaggtggt ggcgcaccag tggcagacaa taacgaaggt    240
gccgatggag tgggtagttc ctcgggaaat tggcattgcg attcccaatg ctgggggac    300 agagtcatca ccaccagcac ccgaacctgg gccctgccca cctacaacaa tcacctctac    360
aagcaaatct ccaacagcac atctggagga tcttcaaatg acaacgccta cttcggctac    420
agcaccccct gggggtattt tgacttcaac agattccact gccacttctc accacgtgac    480
tggcagcgac tcatcaacaa caactgggga ttccggccta gcgactcaa cttcaagctc    540 ttcaacattc aggtcaaaga ggttacggac aacaatggag tcaagaccat cgccaataac    600
cttaccagca cggtccaggt cttcacggac tcagactatc agctcccgta cgtgctcggg    660
tcggctcacg agggctgcct cccgccgttc ccagcggacg ttttcatgat tcctcagtac    720
gggtatctga cgcttaatga tggaagccag gccgtgggtc gttcgtcctt ttactgcctg    780
gaatatttcc cgtcgcaaat gctaagaacg ggtaacaact tccagttcag ctacgagttt    840
gagaacgtac ctttccatag cagctacgct cacagccaaa gcctggaccg actaatgaat    900
ccactcatcg accaatactt gtactatctc tcaaagacta ttaacggttc tggacagaat    960
caacaaacgc taaaattcag tgtggccgga cccagcaaca tggctgtcca gggaagaaac   1020
tacatacctg gacccagcta ccgacaacaa cgtgtctcaa ccactgtgac tcaaaacaac   1080
aacagcgaat ttgcttggcc tggagcttct tctttgggctc tcaatggacg taatagcttg   1140
atgaatcctg gacctgctat ggccagccac aaagaaggag aggaccgttt ctttcctttg   1200
tctggatctt taattttgg caaacaagga actggaagag acaacgtgga tgcggacaaa   1260
gtcatgataa ccaacgaaga agaaattaaa actactaacc cggtagcaac ggagtcctat   1320
ggacaagtgg ccacaaacca ccagagtgcc aagcacagg cgcagaccgg ctgggttcaa   1380
aaccaaggaa tacttccggg tatggtttgg caggacagag atgtgtacct gcaaggaccc   1440
```

```
atttgggcca aaattcctca cacggacggc aactttcacc cttctccgct gatgggaggg    1500
tttggaatga agcacccgcc tcctcagatc ctcatcaaaa acacacctgt acctgcggat    1560
cctccaacgg ccttcaacaa ggacaagctg aactctttca tcacccagta ttctactggc    1620
caagtcagcg tggagatcga gtgggagctg cagaaggaaa acagcaagcg ctggaacccg    1680
gagatccagt acacttccaa ctattacaag tctaataatg ttgaatttgc tgttaatact    1740
gaaggtgtat atagtgaacc ccgcccccatt ggcaccagat acctgactcg taatctgtaa    1800
```

<210> SEQ ID NO 73
<211> LENGTH: 2217
<212> TYPE: DNA
<213> ORGANISM: Adeno-associated virus

<400> SEQUENCE: 73

```
atggctgctg acggttatct tccagattgg ctcgaggaca acctctctga gggcattcgc      60
gagtggtggg acctgaaacc tggagccccc aagcccaagg ccaaccagca gaagcaggac     120
gacggccggg gtctggtgct tcctggctac aagtacctcg acccttcaa cggactcgac     180
aaggggagc ccgtcaacgc ggcggacgca gcggccctcg agcacgacaa ggcctacgac     240
cagcagctca agcgggtga caatccgtac ctgcggtata ccacgccga cgccgagttt     300
caggagcgtc tgcaagaaga tacgtctttt gggggcaacc tcgggcgagc agtcttccag     360
gccaagaagc gggttctcga acctctcggt ctggttgagg aagctgctaa gacggctcct     420
ggaaagaaga accggtaga accgtcacct cagcgttccc ccgactcctc cacgggcatc     480
ggcaagaaag ccagcagcc cgctaaaaag agactgaact ttgggcagac tggcgagtca     540
gagtcagtcc ccgaccctca accaatcgga gaaccaccag caggccctc tggtctggga     600
tctggtacaa tggctgcagg cggtggcgct ccaatggcag acaataacga aggcgccgac     660
ggagtgggta gttcctcagg aaattggcat tgcgattcca catggctggg cgacagagtc     720
atcaccacca gcacccgaac ctgggccctg cccacctaca acaaccacct ctacaagcaa     780
atctccaacg gacatcgggg aggaagcacc aacgacaaca cctacttcgg ctacagcacc     840
ccctgggggt attttgactt caacagattc cactgccact tctcaccacg tgactggcag     900
cgactcatca caacaactg gggattccgg ccaaaaagac tcagcttcaa gctcttcaac     960
atccaggtca aggaggtcac gcagaatgaa ggcaccaaga ccatcgccaa taaccttacc    1020
agcacgattc aggtattta ggactcggaa taccagctgc cgtacgtcct cggctccgcg    1080
caccagggct gcctgcctcc gttcccggcg gatgtcttca tgattcccca gtacggctac    1140
ctgacactga acaatggaag tcaagccgta ggccgttcct ccttctactg cctggaatat    1200
tttccatctc aaatgctgcg aactggaaac aattttgaat tcagctacac cttcgaggac    1260
gtgcctttcc acagcagcta cgcacacagc cagagcttgg accgactgat gaatcctctc    1320
attgaccagt acctgtacta cttatccaga actcagtcca caggaggaac tcaaggtacc    1380
cagcaattgt tattttctca agctgggcct gcaaacatgt cggctcaggc caagaactgg    1440
ctgcctggac cttgctaccg gcagcagcga gtctccacga cactgtcgca aacaacaac    1500
agcaactttg cttggactgg tgccaccaaa tatcacctga cggaagaga ctctctggtg    1560
aatcccggtg tcgccatggc aacccacaag gacgacgagg aacgcttctt cccgtcgagc    1620
ggagtcctga tgtttggaaa acagggtgct ggaagagaca atgtggacta cagcagcgtt    1680
atgctaacaa gcgaagaaga aattaaaacc actaaccctg tagccacaga acaatacggc    1740
```

```
gtggtggctg acaacttgca gcaagccaat acagggccta ttgtgggaaa tgtcaacagc      1800
caaggagcct tacctggcat ggtctggcag aaccgagacg tgtacctgca gggtcccatc      1860
tgggccaaga ttcctcacac ggacggcaac tttcacccgt ctcctctgat gggcggcttt      1920
ggacttaaac acccgcctcc acagatcctg atcaagaaca cgccggtacc tgcggatcct      1980
ccaacaacgt tcagccaggc gaaattggct tccttcatca cgcagtacag caccggacag      2040
gtcagcgtgg aaatcgagtg ggagctgcag aaggagaaca gcaaacgctg gaacccagag      2100
attcagtaca cttcaaacta ctacaaatct acaaatgtgg actttgctgt caatacagag      2160
ggaacttatt ctgagcctcg ccccattggt actcgttatc tgacacgtaa tctgtaa        2217
```

<210> SEQ ID NO 74  
<211> LENGTH: 1806  
<212> TYPE: DNA  
<213> ORGANISM: Adeno-associated virus

<400> SEQUENCE: 74

```
acggctcctg gaaagaagag accggtagaa ccgtcacctc agcgttcccc cgactcctcc        60
acgggcatcg gcaagaaagg ccagcagccc gctaaaaaga gactgaactt tgggcagact       120
ggcgagtcag agtcagtccc cgaccctcaa ccaatcggag aaccaccagc aggcccctct       180
ggtctgggat ctggtacaat ggctgcaggc ggtggcgctc caatggcaga caataacgaa       240
ggcgccgacg gagtgggtag ttcctcagga aattggcatt gcgattccac atggctgggc       300
gacagagtca tcaccaccag cacccgaacc tgggccctgc ccacctacaa caaccacctc       360
tacaagcaaa tctccaacgg gacatcggga ggaagcacca cgacaacac  ctacttcggc       420
tacagcaccc cctgggggta ttttgacttc aacagattcc actgccactt ctcaccacgt       480
gactggcagc gactcatcaa caacaactgg ggattccggc aaaaagact  cagcttcaag       540
ctcttcaaca tccaggtcaa ggaggtcacg cagaatgaag gcaccaagac catcgccaat       600
aaccttacca gcacgattca ggtatttacg gactcggaat accagctgcc gtacgtcctc       660
ggctccgcgc accagggctg cctgcctccg ttcccggcgg atgtcttcat gattccccag       720
tacggctacc tgacactgaa caatggaagt caagccgtag ccgttcctc  cttctactgc       780
ctggaatatt ttccatctca aatgctgcga actggaaaca attttgaatt cagctacacc       840
ttcgaggacg tgccttttca cagcagctac gcacacagcc agagcttgga ccgactgatg       900
aatcctctca ttgaccagta cctgtactac ttatccagaa ctcagtccac aggaggaact       960
caaggtaccc agcaattgtt attttctcaa gctgggcctg caaacatgtc ggctcaggcc      1020
aagaactggc tgcctggacc ttgctaccgg cagcagcgag tctccacgac actgtcgcaa      1080
aacaacaaca gcaactttgc ttggactggt gccaccaaat atcacctgaa cggaagagac      1140
tctctggtga atcccggtgt cgccatggca acccacaagg acgacgagga acgcttcttc      1200
ccgtcgagcg gagtcctgat gtttggaaaa cagggtgctg aagagacaa  tgtggactac      1260
agcagcgtta tgctaacaag cgaagaagaa attaaaacca ctaaccctgt agccacagaa      1320
caatacggcg tggtggctga acttgcag caagccaata cagggcctat tgtgggaaat      1380
gtcaacagcc aaggagcctt acctggcatg gtctggcaga accgagacgt gtacctgcag      1440
ggtcccatct gggccaagat tcctcacacg gacggcaact tcacccgtc  tcctctgatg      1500
ggcggctttg gacttaaaca cccgcctcca cagatcctga tcaagaacac gccggtacct      1560
gcggatcctc caacaacgtt cagccaggcg aaattggctt ccttcatcac gcagtacagc      1620
accggacagg tcagcgtgga aatcgagtgg gagctgcaga aggagaacag caaacgctgg      1680
```

| | |
|---|---|
| aacccagaga ttcagtacac ttcaaactac tacaaatcta caaatgtgga ctttgctgtc | 1740 |
| aatacagagg gaacttattc tgagcctcgc cccattggta ctcgttatct gacacgtaat | 1800 |
| ctgtaa | 1806 |

<210> SEQ ID NO 75
<211> LENGTH: 2202
<212> TYPE: DNA
<213> ORGANISM: Adeno-associated virus

<400> SEQUENCE: 75

| | |
|---|---|
| atggctgctg acggttatct tccagattgg ctcgaggaca acctctctga gggcattcgc | 60 |
| gagtggtggg acctgaaacc tggagccccg aagcccaagg ccaaccagca gaagcaggac | 120 |
| gacggccggg gtctggtgct tcctggctac aagtacctcg acccttcaa cggactcgac | 180 |
| aagggggagc ccgtcaacgc ggcggacgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt ggggggcaacc tcgggcgagc agtcttccag | 360 |
| gccaagaaga gggtactcga acctctgggc ctggttgaag aaggtgctaa aacggctcct | 420 |
| ggaaagaaga gaccgttaga gtcaccacaa gagcccgact cctcctcggg catcggcaaa | 480 |
| aaaggcaaac aaccagccag aaagaggctc aactttgaag aggacactgg agccggagac | 540 |
| ggaccccctg aaggatcaga taccagcgcc atgtcttcag acattgaaat gcgtgcagca | 600 |
| ccggcggaa atgctgtcga tgcgggacaa ggttccgatg gagtgggtaa tgcctcgggt | 660 |
| gattggcatt gcgattccac ctggtctgag ggcaaggtca acaacctc gaccagaacc | 720 |
| tgggtcttgc ccacctacaa caaccacttg tacctgcgtc tcggaacaac atcaagcagc | 780 |
| aacacctaca cggattctc cacccctgg ggatattttg acttcaacag attccactgt | 840 |
| cacttctcac cacgtgactg gcaaagactc atcaacaaca ctggggact acgaccaaaa | 900 |
| gccatgcgcg ttaaaatctt caatatccaa gttaaggagg tcacaacgtc gaacggcgag | 960 |
| actacggtcg ctaataacct taccagcacg gttcagatat ttgcggactc gtcgtatgag | 1020 |
| ctcccgtacg tgatggacgc tggacaagag gggagcctgc ctccttccc caatgacgtg | 1080 |
| ttcatggtgc tcaatatgg ctactgtggc atcgtgactg gcgagaatca gaaccaaacg | 1140 |
| gacagaaacg ctttctactg cctggagtat tttccttcgc aaatgttgag aactggcaac | 1200 |
| aactttgaaa tggcttacaa ctttgagaag gtgccgttcc actcaatgta tgctcacagc | 1260 |
| cagagcctgg acagactgat gaatcccctc ctggaccagt acctgtggca cttacagtcg | 1320 |
| actacctctg gagagactct gaatcaaggc aatgcagcaa ccacatttgg aaaaatcagg | 1380 |
| agtggagact ttgcctttta cagaaagaac tggctgcctg gccttgtgt taaacagcag | 1440 |
| agattctcaa aaactgccag tcaaaattac aagattcctg ccagcggggg caacgctctg | 1500 |
| ttaaagtatg acacccacta taccttaaac aaccgctgga gcaacatcgc gcccggacct | 1560 |
| ccaatggcca cagccggacc ttcggatggg gacttcagta acgcccagct tatattccct | 1620 |
| ggaccatctg ttaccggaaa tacaacaact tcagccaaca atctgttgtt tacatcagaa | 1680 |
| gaagaaattg ctgccaccaa cccaagagac acggacatgt ttggccagat tgctgacaat | 1740 |
| aatcagaatg ctacaactgc tcccataacc ggcaacgtga ctgctatggg agtgctgcct | 1800 |
| ggcatggtgt ggcaaacag agacatttac taccaagggc caatttggc caagatccca | 1860 |
| cacgcggacg gacattttca tccttcaccg ctgattggtg ggtttggact gaaacacccg | 1920 |

| cctcccaga tattcatcaa gaacactccc gtacctgcca atcctgcgac aaccttcact | 1980 |
| gcagccagag tggactcttt catcacacaa tacagcaccg gccaggtcgc tgttcagatt | 2040 |
| gaatgggaaa ttgaaaagga acgctccaaa cgctggaatc ctgaagtgca gtttacttca | 2100 |
| aactatggga accagtcttc tatgttgtgg gctcctgata aactgggaa gtatacagag | 2160 |
| ccgcgggtta ttggctctcg ttatttgact aatcatttgt aa | 2202 |

```
<210> SEQ ID NO 76
<211> LENGTH: 1791
<212> TYPE: DNA
<213> ORGANISM: Adeno-associated virus

<400> SEQUENCE: 76
```

| acggctcctg gaaagaagag accgttagag tcaccacaag agcccgactc ctcctcgggc | 60 |
| atcggcaaaa aaggcaaaca accagccaga aagaggctca actttgaaga ggacactgga | 120 |
| gccggagacg gacccctga aggatcagat accagcgcca tgtcttcaga cattgaaatg | 180 |
| cgtgcagcac cgggcggaaa tgctgtcgat gcgggacaag gttccgatgg agtgggtaat | 240 |
| gcctcgggtg attggcattg cgattccacc tggtctgagg gcaaggtcac aacaacctcg | 300 |
| accagaacct gggtcttgcc cacctacaac aaccacttgt acctgcgtct cggaacaaca | 360 |
| tcaagcagca acacctacaa cggattctcc accccctggg gatattttga cttcaacaga | 420 |
| ttccactgtc acttctcacc acgtgactgg caaagactca tcaacaacaa ctggggacta | 480 |
| cgaccaaaag ccatgcgcgt taaaatcttc aatatccaag ttaaggaggt cacaacgtcg | 540 |
| aacggcgaga ctacggtcgc taataacctt accagcacgg ttcagatatt tgcggactcg | 600 |
| tcgtatgagc tcccgtacgt gatggacgct ggacaagagg ggagcctgcc tccttttcccc | 660 |
| aatgacgtgt tcatggtgcc tcaatatggc tactgtggca tcgtgactgg cgagaatcag | 720 |
| aaccaaacgg acagaaacgc tttctactgc ctggagtatt ttccttcgca aatgttgaga | 780 |
| actggcaaca acttttgaaat ggcttacaac tttgagaagg tgccgttcca ctcaatgtat | 840 |
| gctcacagcc agagcctgga cagactgatg aatcccctcc tggaccagta cctgtggcac | 900 |
| ttacagtcga ctacctctgg agagactctg aatcaaggca atgcagcaac acatttgga | 960 |
| aaaatcagga gtggagactt tgcctttta cagaaagaact ggctgcctgg gccttgtgtt | 1020 |
| aaacagcaga gattctcaaa aactgccagt caaaattaca agattcctgc cagcgggggc | 1080 |
| aacgctctgt aaagtatga cacccactat accttaaaca accgctggag caacatcgcg | 1140 |
| cccgacctc caatggccac agccggacct tcggatgggg acttcagtaa cgcccagctt | 1200 |
| atattccctg gaccatctgt taccggaaat acaacaactt cagccaacaa tctgttgttt | 1260 |
| acatcagaag aagaaattgc tgccaccaac ccaagagaca cggacatgtt tggccagatt | 1320 |
| gctgacaata atcagaatgc tacaactgct cccataaccg gcaacgtgac tgctatggga | 1380 |
| gtgctgcctg gcatggtgtg gcaaaacaga gacatttact accaagggcc aatttgggcc | 1440 |
| aagatcccac acgcggacgg acattttcat ccttcaccgc tgattggtgg gtttggactg | 1500 |
| aaacacccgc ctcccagat attcatcaag aacactcccg tacctgccaa tcctgcgaca | 1560 |
| accttcactg cagccagagt ggactctttc atcacacaat acagcaccgg ccaggtcgct | 1620 |
| gttcagattg aatgggaaat tgaaaaggaa cgctccaaac gctggaatcc tgaagtgcag | 1680 |
| tttacttcaa actatgggaa ccagtcttct atgttgtggg ctcctgatac aactgggaag | 1740 |
| tatacagagc cgcgggttat tggctctcgt tatttgacta atcatttgta a | 1791 |

<210> SEQ ID NO 77
<211> LENGTH: 2229
<212> TYPE: DNA
<213> ORGANISM: Adeno-associated virus

<400> SEQUENCE: 77

| | | | | | |
|---|---|---|---|---|---|
| atggctgctg | acggttatct | tccagattgg | ctcgaggaca | acctctctga | aggcattcgc | 60 |
| gagtggtggg | cgctgaaacc | tggagctcca | aacccaagg | ccaaccaaca | gcatcaggac | 120 |
| aacgcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | ggcctacgac | 240 |
| aagcagctcg | agcaggggga | caacccgtat | ctcaagtaca | accacgccga | cgccgagttc | 300 |
| cagcagcgct | tggcgaccga | cacctctttt | gggggcaacc | tcgggcgagc | agtcttccag | 360 |
| gccaaaaaga | ggattctcga | gcctctgggt | ctggttgaag | agggcgttaa | aacggctcct | 420 |
| ggaaagaaac | gcccattaga | aaagactcca | aatcggccga | ccaacccgga | ctctgggaag | 480 |
| gcccccgcca | agaaaaagca | aaaagacggc | gaaccagccg | actctgctag | aaggacactc | 540 |
| gactttgaag | actctggagc | aggagacgga | cccctgagg | gatcatcttc | cggagaaatg | 600 |
| tctcatgatg | ctgagatgcg | tgcggcgcca | ggcggaaatg | ctgtcgaggc | gggacaaggt | 660 |
| gccgatggag | tgggtaatgc | ctccggtgat | tggcattgcg | attccacctg | gtcagagggc | 720 |
| cgagtcacca | ccaccagcac | ccgaacctgg | gtcctaccca | cgtacaacaa | ccacctgtac | 780 |
| ctgcgaatcg | gaacaacggc | caacagcaac | acctacaacg | gattctccac | ccctgggga | 840 |
| tactttgact | taaccgctt | ccactgccac | ttttccccac | gcgactggca | gcgactcatc | 900 |
| aacaacaact | ggggactcag | gccgaaatcg | atgcgtgtta | aaatcttcaa | catacaggtc | 960 |
| aaggaggtca | cgacgtcaaa | cggcgagact | acggtcgcta | taaccttac | cagcacggtt | 1020 |
| cagatctttg | cggattcgac | gtatgaactc | ccatacgtga | tggacgccgg | tcaggagggg | 1080 |
| agctttcctc | cgtttcccaa | cgacgtcttt | atggttcccc | aatacggata | ctgcggagtt | 1140 |
| gtcactggaa | aaaccagaa | ccagacagac | agaaatgcct | tttactgcct | ggaatacttt | 1200 |
| ccatcccaaa | tgctaagaac | tggcaacaat | tttgaagtca | gttaccaatt | tgaaaaagtt | 1260 |
| cctttccatt | caatgtacgc | gcacagccag | agcctggaca | gaatgatgaa | tcctttactg | 1320 |
| gatcagtacc | tgtggcatct | gcaatcgacc | actaccggaa | attcccttaa | tcaaggaaca | 1380 |
| gctaccacca | cgtacgggaa | aattaccact | ggagactttg | cctactacag | gaaaaactgg | 1440 |
| ttgcctggag | cctgcattaa | caacaaaaaa | ttttcaaaga | atgccaatca | aaactacaag | 1500 |
| attcccgcca | gcggggaga | cgcccttta | aagtatgaca | cgcataccac | tctaaatggg | 1560 |
| cgatggagta | acatggctcc | tggacctcca | atggcaaccg | caggtgccgg | ggactcggat | 1620 |
| tttagcaaca | gccagctgat | ctttgccgga | cccaatccga | gcgtaacac | gaccacatct | 1680 |
| tcaaacaatt | tgttgtttac | ctcagaagag | gagattgcca | aacaaaaccc | acgagacacg | 1740 |
| gacatgtttg | gacagattgc | agataataat | caaaatgcca | ccaccgcccc | tcacatcgct | 1800 |
| aacctggacg | ctatgggaat | tgttccggga | atggtctggc | aaaacagaga | catctactac | 1860 |
| cagggcccta | tttgggccaa | ggtccctcac | acggacggac | actttcaccc | ttcgccgctg | 1920 |
| atgggaggat | ttggactgaa | acaccccgcct | ccacagattt | tcatcaaaaa | cacccccgta | 1980 |
| cccgccaatc | ccaatactac | ctttagcgct | gcaaggatta | ttctttttct | gacgcagtac | 2040 |
| agcaccggac | aagttgccgt | tcagatcgac | tgggaaattc | agaaggagca | ttccaaacgc | 2100 |
| tggaatcccg | aagttcaatt | tacttcaaac | tacggcactc | aaaattctat | gctgtgggct | 2160 |

```
cccgacaatg ctggcaacta ccacgaactc cgggctattg ggtcccgttt cctcacccac     2220
cacttgtaa                                                             2229

<210> SEQ ID NO 78
<211> LENGTH: 1818
<212> TYPE: DNA
<213> ORGANISM: Adeno-associated virus

<400> SEQUENCE: 78
acggctcctg gaaagaaacg cccattagaa aagactccaa atcggccgac caacccggac       60
tctgggaagg ccccggccaa gaaaaagcaa aaagacggcg aaccagccga ctctgctaga      120
aggacactcg actttgaaga ctctggagca ggagacggac cccctgaggg atcatcttcc      180
ggagaaatgt ctcatgatgc tgagatgcgt gcggcgccag gcggaaatgc tgtcgaggcg      240
ggacaaggtg ccgatggagt gggtaatgcc tccggtgatt ggcattgcga ttccacctgg      300
tcagagggcc gagtcaccac caccagcacc cgaacctggg tcctaccac gtacaacaac      360 cacctgtacc tgcgaatcgg aacaacggcc aacagcaaca cctacaacgg attctccacc      420
ccctggggat actttgactt taaccgcttc cactgccact tttccccacg cgactggcag      480
cgactcatca caacaactg gggactcagg ccgaaatcga tgcgtgttaa aatcttcaac      540
atacaggtca aggaggtcac gacgtcaaac ggcgagacta cggtcgctaa taaccttacc      600
agcacggttc agatctttgc ggattcgacg tatgaactcc catacgtgat ggacgccggt      660
caggagggga gctttcctcc gtttcccaac gacgtcttta tggttcccca atacggatac      720
tgcggagttg tcactggaaa aaaccagaac cagacagaca gaaatgcctt ttactgcctg      780
gaatactttc catcccaaat gctaagaact ggcaacaatt ttgaagtcag ttaccaattt      840
gaaaaagttc ctttccattc aatgtacgcg cacagccaga gcctggacag aatgatgaat      900
cctttactgg atcagtacct gtggcatctg caatcgacca ctaccggaaa ttcccttaat      960
caaggaacag ctaccaccac gtacgggaaa attaccactg gagactttgc ctactacagg     1020
aaaaactggt tgcctggagc ctgcattaaa caacaaaaat tttcaaagaa tgccaatcaa     1080
aactacaaga ttcccgccag cggggagac gcccttttaa agtatgacac gcataccact     1140
ctaaatgggc gatggagtaa catggctcct ggacctccaa tggcaaccgc aggtgccggg     1200
gactcggatt ttagcaacag ccagctgatc tttgccggac ccaatccgag cggtaacacg     1260
accacatctt caaacaattt gttgtttacc tcagaagagg agattgccac aacaaaccca     1320
cgagacacgg acatgtttgg acagattgca gataataatc aaaatgccac caccgccct     1380 cacatcgcta acctggacgc tatgggaatt gttcccggaa tggtctggca aaacagagac     1440
atctactacc agggccctat ttgggccaag gtccctcaca cggacggaca ctttcaccct     1500
tcgccgctga tgggaggatt tggactgaaa cacccgcctc acagattttt catcaaaaac     1560
acccccgtac ccgccaatcc caatactacc tttagcgctg caaggattaa ttctttttctg     1620 acgcagtaca gcaccggaca agttgccgtt cagatcgact gggaaattca gaaggagcat     1680
tccaaacgct ggaatcccga agttcaattt acttcaaact acggcactca aaattctatg     1740
ctgtgggctc ccgacaatgc tggcaactac cacgaactcc gggctattgg gtcccgtttc     1800
ctcacccacc acttgtaa                                                  1818
```